(12) United States Patent
Chaplin et al.

(10) Patent No.: US 8,198,302 B2
(45) Date of Patent: *Jun. 12, 2012

(54) COMPOSITIONS AND METHODS WITH ENHANCED THERAPEUTIC ACTIVITY

(75) Inventors: David J. Chaplin, Watlington (GB); Klaus Edvardsen, Lund (SE); Kevin G. Pinney, Woodway, TX (US); Joseph Anthony Prezioso, Boston, MA (US); Mark Wood, Milton, MA (US)

(73) Assignees: OXiGENE, Inc., South San Francisco, CA (US); Baylor University, Waco, TX (US)

( * ) Notice: Subject to any disclaimer, the term of this patent is extended or adjusted under 35 U.S.C. 154(b) by 1606 days.

This patent is subject to a terminal disclaimer.

(21) Appl. No.: 10/790,662

(22) Filed: Mar. 1, 2004

(65) Prior Publication Data

US 2004/0242696 A1    Dec. 2, 2004

(51) Int. Cl.
    A61K 31/445    (2006.01)
(52) U.S. Cl. ........................................... 514/317
(58) Field of Classification Search .................. 514/317
    See application file for complete search history.

(56) References Cited

U.S. PATENT DOCUMENTS

| | | | |
|---|---|---|---|
| 5,079,257 A | 1/1992 | Speckamp et al. | 514/312 |
| 5,409,953 A * | 4/1995 | Pettit et al. | 514/464 |
| 5,430,062 A | 7/1995 | Cushman et al. | 514/646 |
| 5,525,632 A | 6/1996 | Obsumi et al. | 514/646 |
| 5,567,786 A | 10/1996 | Tseng et al. | 526/264 |
| 5,674,906 A | 10/1997 | Hatanaka et al. | 514/626 |
| 6,423,753 B1 | 7/2002 | Dougherty | 514/719 |
| 6,919,324 B2 * | 7/2005 | Chaplin et al. | 514/114 |
| 2003/0129223 A1 * | 7/2003 | Wartchow et al. | 424/450 |

FOREIGN PATENT DOCUMENTS

| | | |
|---|---|---|
| WO | WO 92/16486 | 10/1992 |
| WO | 98/39323 | 9/1998 |
| WO | WO 99/02166 | 1/1999 |
| WO | WO 00/40529 | 7/2000 |
| WO | WO 00/66528 | 11/2000 |
| WO | WO 01/32210 A2 | 5/2001 |
| WO | WO 01/81355 A1 | 11/2001 |
| WO | WO 02/02110 A1 | 1/2002 |
| WO | WO 02/04434 A1 | 1/2002 |
| WO | WO 02/08213 A1 | 1/2002 |

(Continued)

OTHER PUBLICATIONS

Gutierrez, P. L., "The role of NAD(P)H oxidoreductase (DT-diaphorase) in the bioactivation of quinone-containing antitumor agents: a review", Free Radic. Biol. Med., 29(3-4):263-275 (2000), especially p. 262, $2^{nd}$ paragraph.*

(Continued)

Primary Examiner — San-Ming Hui
(74) Attorney, Agent, or Firm — Karen E. Flick

(57) ABSTRACT

Novel quinone and catechol compositions, compositions containing prodrugs of quinone and catechol compositions, and methods of use for the treatment of solid tumor cancers and other vascular proliferative disorders. The disclosure particularly relates to the discovery of dual activity agents capable of generating both a vascular targeting effect and direct tumor cell cytotoxicity in order to achieve an enhanced anti-tumor response in a patient.

8 Claims, 7 Drawing Sheets

FOREIGN PATENT DOCUMENTS

| | | |
|---|---|---|
| WO | WO 02/12227 A2 | 2/2002 |
| WO | WO 02/14329 A1 | 2/2002 |
| WO | WO 02/49994 A2 | 6/2002 |
| WO | WO 02/50007 A2 | 6/2002 |
| WO | WO 03/035008 A2 | 5/2003 |
| WO | WO 03/040077 A1 | 5/2003 |

OTHER PUBLICATIONS

Chawla, S., Effect of Deoxyarbutin and its second-generation derivatives on melanocyte viability and function, Division of Research and Advanced Studies of the University of Cincinnati (2006), printed pp. 1-216, especially p. 80).*

Blum et al., Biochemistry, 2000;39;15705-15712.*

Amaro, et al., "Metabolic activation of PCBs to Quinones: reactivity toward nitrogen and sulfur nucleophiles and influence of superoxide dismutase", Chem. Res. Toxicol., 9:623-629 (1996).

Begleiter, A., "Clinical applications of quinone-containing alkylating agents", Frontiers in Biosci., 5:e153-171 (2000).

Bolton, J. L., "Quinoids, quinoid radicals, and phenoxyl radicals formed from estrogens and antiestrogens", Toxicology, 177:55-65 (2002).

Bui, et al., "Direct biocatalytic synthesis of functionalized catechols: a green alternative to traditional methods with high effective mass yield", Green Chem., 2:263-265 (2000).

Bui, et al., "Direct biooxidation of arenas to corresponding catechols with E. coli JM109 (pDTG602). Application to synthesis of combretastatins A-1 and B-1", Tetrahedron Lett., 43:2839-2841 (2002).

Fan, et al., "4-hydroxylated metabolites of antiestrogens, tamoxifen and toremifene are metabolized to unusually stable quinone methides", Chem. Res. Toxicol., 13(1):45-52 (2000).

Faig, et al., "Structure-based development of anticancer drugs: complexes of NAD(P)H:quinone oxidoreductase 1 with chemotherapeutic quinones", Structure, 9(8):659-667 (2001).

Flowers-Geary, et al., "Cytotoxicity and mutagenicity of polycyclic aromatic hydrocarbon ortho-quinones produced by dihydrodiol dehydrogenase", Chem. Biol. Interact., 99(1-3):55-72 (1996).

Gastpar, et al., "Methoxy-substituted 3-formyl-2-phenylindoles inhibit tubulin polymerization", J. Med. Chem., 41: 4965-4972 (1998).

Gutierrez, P. L., "The metabolism of quinone-containing alkylating agents: free radical production and measurement", Frontiers in Biosci., 5:d629-638 (2000).

Gutierrez, P. L., "The role of NAD(P)H oxidoreductase (DT-diaphorase) in the bioactivation of quinone-containing antitumor agents: a review", Free Radic. Biol. Med., 29(3-4):263-275 (2000).

Ham, et al., "Mechanism of cell cycle arrest by menadione", Bull. Korean Chem. Soc., 21(12):1173-1174 (2000).

Hill, et al., "Preclinical evaluation of the antitumor activity of the novel vascular targeting agent Oxi 4503", Anticancer Res., 22:1453-1458 (2002).

Holwell, et al., "Anti-tumor and Anti-vascular effects of the novel tubulin-binding agent Combretastatin A-1 Phosphate", Anticancer Res., 22:3933-3940 (2002).

Holwell, et al., "Combretastatin A-1 Phosphate a novel tubulin binding agent with in vivo anti-vascular effects in experimental tumors", Anticancer Res., 22:707-712 (2002).

Li, et al., "Discovery and development of antimitotic agents that inhibit tubulin polymerisation for the treatment of cancer", Expert Opin. Ther. Patents, 12(11):1663-1702 (2002).

Pang, et al., "Simultaneous determination of etoposide and its catechol metabolite in the plasma of pediatric patients by liquid chromatography/tandem mass spectrometry", J. Mass Spectrom., 36:771-781 (2001).

Pettit, et al., "Antineoplastic agents 429: Syntheses of the combretastatin A-1 and combretastatin B-1 prodrugs", Anti-Cancer Drug Design, 15:203-26 (2000).

Pettit, et al., "Antineoplastic agents 440: Asymmetric synthesis and evaluation of the Combretastatin A-1 probes (1S,2S)- and (1R,2R)-1,2-dihydroxy-1-(2',3'-dihydroxy-4'-methoxyphenyl)-2-(3", 4",5"-trimethoxyphenyl)-ethane", J. Nat. Prod., 63:969-674 (2000).

Pettit, et al., "Antineoplastic agents 389: New syntheses of the combretastatin A-4 prodrug", Anti-Cancer Drug Design, 13:183-191 (1998).

Singh, et al., "Isolation, structure, and synthesis of combretastatin C-1", J. Org. Chem., 54:4105-4114 (1989).

Sridhar, et al., "Amino acid adducts of PAH o-quinones: model studies with naphthalene-1,2-dione", Tetrahedron, 57:407-412 (2001).

Wardman, P., "Electron transfer and oxidative stress as key factors in the design of drugs selectively active in hypoxia", Curr. Med. Chem., 8(7): 739-761 (2001).

Workman, P., "Enzyme-directed bioreductive drug development revisited: a commentary on recent progress and future prospects with emphasis on quinone anticancer agents and quinone metabolizing enzymes, particularly DT-diaphorase", Oncol. Res., 6(10-11):461-475 (1994).

Yao, et al., "Synthesis and reactivity of potential toxic metabolites of tamoxifen analogues: droloxifene and toremifene o-quinones", Chem. Res. Toxicol., 14(12):1643-1653 (2001).

Zhang, et al., "Synthesis and reactivity of a potential carcinogenic metabolite of tamoxifen: 3,4-dihydroxytamoxifen-o-quinone", Chem. Res. Toxicol., 13(1):53-62 (2000).

Griggs et al., "Potent anti-metastatic activity of combretastatin." International Journal of Oncology, 19, (2001), pp. 821-825.

Griggs et al., "Inhibition of Proliferative Retinopathy by the Anti-Vascular Agent Combretastatin-A4." American Journal of Pathology, vol. 160, No. 3, (Mar. 2002), pp. 1097-1103.

Ronjiani et al., "Activity of the vascular Targeting Agent Combretastatin A-4 Disodium Phosphate in a Xenograft Model of AIDS-Associated Kaposi's Sarcoma." Taylor & Francis, (2002), pp. 98-105.

Barcher et al., "D-24851, a Novel Synthetic Microtubule Inhibitor, Exerts Curative Antitumoral Activity in Vivo, Shows Efficacy toward Multidrug-resistant Tumor Cells, and Lacks Neurotoxicity." Cancer, vol. 61, ( Jan. 1, 2001), pp. 392-399.

Combeau et al., "RPR112378 and RPR115781: Two Representatives of a New Family of Microtubule Assembly Inhibitors." Molecular Pharmacology, vol. 57, (2000), pp. 553-563.

Hammond et al., "Studies to show that with podophyllotoxin the early replicative stages of herpes simplex virus type 1 depend upon functional cytoplasmic microtubules." J. Med. Microbiol., vol. 45, (1996), pp. 167-172.

Kanoh et al., "(-)-Phenylahistin Arrest Cells in Mitosis by Inhibiting Tubulin Polymerization." The Journal of Antibiotics, vol. 52, No. 2, (Feb. 1999), pp. 134-141.

Leoni et al., "Indanocine, a Microtubule-Binding Indanone and a Selective Inducer of Apoptosis in Multidrug-Resistant Cancer Cells." J. Natl. Cancer Inst., vol. 92, (2000), pp. 217-224.

Wu-Wong et al., "Identification and Characterization of A-105972, an Antineoplastic Agent." Cancer Research, 2001, vol. 61, pp. 1486-1492.

Kanoh et al., "(-)-Phenylahistin Arrests Cells in Mitosis by Inhibiting Tubulin Polymerization." The Journal of Antibiotics, Feb. 1999, vol. 52, No. 2, pp. 134-141.

* cited by examiner

COMPOSITIONS AND METHODS WITH ENHANCED THERAPEUTIC ACTIVITY

RELATED APPLICATIONS

This application claims the benefit of priority under 35 U.S.C. 119(e) to copending U.S. Provisional Application Nos. 60/467,486 filed May 2, 2003, and 60/450,565 filed Feb. 28, 2003, the entire contents of which are incorporated herein by reference.

FIELD OF THE INVENTION

This invention relates to novel quinone and catechol compositions, compositions containing prodrugs of quinone and catechol compositions, and methods of use for the treatment of solid tumor cancers and other vascular proliferative disorders. In particular, the invention relates to dual activity agents capable of generating both a vascular targeting effect and direct tumor cell cytotoxicity in order to achieve an enhanced anti-tumor response in a patient.

BACKGROUND OF THE INVENTION

Cancer is a leading cause of death in the industrialized world and despite years of research, many types of cancer lack an effective therapeutic treatment. This is especially true for cancers that are characterized by the presence of large, solid tumors, since it is difficult to deliver an effective dose of a chemotherapeutic agent to the interior of a large tumor mass with a significant degree of selectivity. Moreover, due to the genetic instability of tumor cells, a tumor tissue can rapidly acquire resistance to standard therapeutic regimens.

In order to develop into a large solid tumor mass, however, tumor foci must first establish a network of blood vessels in order to obtain the nutrients and oxygen that are required for continued growth. The tumor vascular network has received enormous interest as a therapeutic target for antineoplastic therapy because of its accessibility to blood-borne chemotherapeutics and the relatively small number of blood vessels that are critical for the survival and continued growth of the much larger tumor mass. Disruption in the function of a single tumor blood vessel can result in an avalanche of ischaemic tumor cell death and necrosis of thousands of cancer cells that depend on it for blood supply. In addition, the accessibility of the tumor vasculature to blood-borne anticancer agents and the relatively stable genome of normal, host vascular tissue can alleviate some of the problems such as bioavailability and acquired drug resistance that are associated with conventional, anti-tumor based therapies.

Much of the research in anti-vascular cancer therapy has focused on understanding the process of new blood vessel formation, known as angiogenesis, and identifying anti-angiogenic agents that inhibit the formation of new blood vessels. Angiogenesis is characterized by the proliferation of tumor endothelial cells that form new vasculature to support the growth of a tumor. This growth is stimulated by certain growth factors produced by the tumor itself. One of these growth factors, Vascular Endothelial Growth Factor ("VEGF"), is relatively specific towards endothelial cells, by virtue of the restricted and up-regulated expression of its cognate receptor. Various anti-angiogenic strategies have been developed to inhibit this signaling process at one or more steps in the biochemical pathway in order to prevent the growth and establishment of the tumor vasculature. However, anti-angiogenic therapies act slowly and must be chronically administered over a period of months to years in order to produce a desired effect.

Vascular Targeting Agents ("VTAs"), also known as Vascular Damaging Agents, are a novel class of antineoplastic drugs that exert their effects on solid tumors by selectively occluding, damaging, or destroying the existing tumor vasculature. This disruption of the tumor vasculature occurs rapidly, within minutes to hours following VTA administration, and manifests as a selective reduction in the flow to at least a portion of a tumor region or loss in the number of functional tumor blood vessels in at least a portion of a tumor region, leading eventually to tumor cell death by induction of hypoxia and nutrient depletion. The selectivity of the agent is evidenced by the fact that there are few adverse effects on the function of blood vessels in normal tissues. Thus, the anti-vascular mechanism of VTA action is quite divorced from that of anti-angiogenic agents that do not disrupt existing tumor vasculature but in contrast inhibit molecular signals which induce the formation of tumor neovasculature.

Combretastatin A-4 Disodium Phosphate Prodrug ("CA4P") is the lead drug of a group of VTAs currently in clinical trials as a VTA. This compound was initially isolated as Combretastatin A-4 ("CA-4") from the stem wood of the African tree *Combretum caffrum* (Combretaceae). CA4P has the following structure:

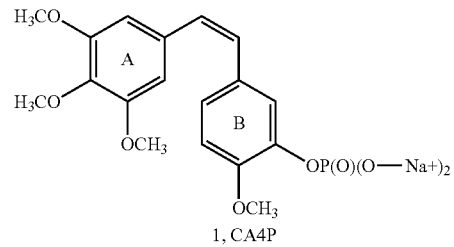

1, CA4P

As described in U.S. Pat. No. 4,996,237, the entire disclosure of which is incorporated herein in entirety, CA-4 was synthesized and found to have potent tubulin binding activity. Moreover, CA-4 was found to be a potent inhibitor of microtubule assembly in tumor endothelium. However, due to the insolubility of CA-4 in human plasma, CA4P was developed (U.S. Pat. No. 5,561,122, the entire disclosure of which is incorporated by reference). When administered to the bloodstream of a patient, the CA4P is cleaved to the active, tubulin-binding CA-4 by endogenous nonspecific phosphatases. It is thought that CA-4 selectively destabilizes the microtubule cytoskeleton of tumor endothelial cells, causing a profound alteration in the shape of the cell which ultimately leads to occlusion of the tumor blood vessel and shutdown of blood flow to the tumor (Galbraith et al, *Anticancer Research*, 2001, 21:93-102; Kanthou and Tozer, *Blood*, 2002, 99(6): 2060-2069).

While in vivo studies have confirmed that vascular damaging effects of VTAs on tumor tissue far exceed their effects on normal tissues (Chaplin, et al., *Anticancer Research*, 1999, 19(1A): 189-196), only in a few cases has a tumor regression or complete tumor response been observed when these agents are used alone as a single agent therapy or monotherapy. The lack of traditional tumor response has been attributed to the rapid recolonization of the necrotic tumor core by a viable rim of tumor cells at the periphery of the tumor capable of receiving oxygen and nutrients from the surrounding normal tissue to resist the effects of blood flow shutdown (Chaplin, et al., Anticancer Research, 1999, 19(1A):189-196). While this viable rim is resistant to VTA therapy, it remains highly susceptible to conventional radiation, chemotherapy and antibody-based therapeutics, and many studies have demonstrated effective tumor regression when VTAs are used in combination with one of these therapies (Li and Rojiani, Int. J. Radiat. Oncol. Biol. Phys., 1998, 42(4): 899-903; Grosios et al., Anticancer Research, 2000, 20(1A): 229-233; Pedley et al., Cancer Research, 2001, 61(12): 4716-4722; WO 02/056692).

Despite the effectiveness when used in combination with VTA therapy, conventional therapies must be administered in repeat daily doses following initial VTA administration in order to achieve prolonged tumor regression. Most conventional therapies are highly cytotoxic, and the patient must cope with prolonged side effects (emesis, hair loss, myelosuppression, etc.) due to chronic administration. VTA therapies lack many of these toxic effects. There is therefore an urgent need in the art for a VTA compound which can be used effectively as a single agent and has the capacity to destroy tumor cells in all regions of the tumor, including the periphery.

SUMMARY OF THE INVENTION

In a first aspect, the invention provides compositions that selectively reduce blood flow to a tumor region and form a ROS in vivo. The compositions include an anticancer agent having a quinone, quinone prodrug, catechol or catechol prodrug moiety. In an embodiment the composition is not combretastatin A-1 or a salt, ester or prodrug thereof.

In a preferred embodiment, invention provides compounds of formula I:

I:

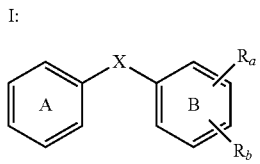

wherein Ring A is optionally substituted with one to five substituents including a $C_1$, $C_2$, $C_3$, $C_4$ or $C_5$ (preferably $C_1$) branched or straight-chain lower alkoxy, cycloalkoxy, heterocycloalkoxy, aryloxy, or lower alkanoyloxy; a halogen or trihaloalkyl; a $C_1$, $C_2$, $C_3$, $C_4$ or $C_5$ (preferably $C_1$) branched or straight chain lower alkyl, allyl, allyloxy, vinyl, or vinyloxy; an OH, or a $C_1$, $C_2$, $C_3$, $C_4$ or $C_5$ (preferably $C_1$) primary, secondary, or tertiary alcohol; $NH_2$ or an amino, lower alkylamino, arylamino, aralkylamino, cycloalkylamino, heterocycloamino, aroylamino, aralkanoylamino, amido, lower alkylamido, arylamido, aralkylamido, cycloalkylamido, heterocycloamido, aroylamido, aralkanoylamido; or oxo, lower alkanoyl, thiol, sulfonyl, sulfonamide, nitro, nitrosyl, cyano, carboxy, carbamyl, aryl, or heterocyclo.

Ring B may include at least one structure denoted by $R_a$ and $R_b$, which represent an ortho-quinone moiety (—(C=O)—(C=O)—), ortho-catechol moiety (—(C—OH)—(C—OH)—) or ortho-catechol pro-drug moiety (—(C—O-Prodrug moiety)-(C—O-Prodrug moeity)-); and the remaining carbons of Ring B may be optionally substituted with one to five substituents including a $C_1$, $C_2$, $C_3$, $C_4$ or $C_5$ (preferably $C_1$) branched or straight-chain lower alkoxy, cycloalkoxy, heterocycloalkoxy, aryloxy, or lower alkanoyloxy; a halogen or trihaloalkyl; a $C_1$, $C_2$, $C_3$, $C_4$ or $C_5$ (preferably $C_1$) branched or straight chain lower alkyl, allyl, allyloxy, vinyl, or vinyloxy; OH or a $C_1$, $C_2$, $C_3$, $C_4$ or $C_5$ (preferably $C_1$) primary, secondary, or tertiary alcohol; $NH_2$ or an amino, lower alkylamino, arylamino, aralkylamino, cycloalkylamino, heterocycloamino, aroylamino, aralkanoylamino, amido, lower alkylamido, arylamido, aralkylamido, cycloalkylamido, heterocycloamido, aroylamido, aralkanoylamido; or oxo, lower alkanoyl, thiol, sulfonyl, sulfonamide, nitro, nitrosyl, cyano, carboxy, carbamyl, aryl, or heterocyclo.

Bridge X may be alkene (—$CR_9$=$CR_{10}$—), alkane (—$CR_9$—$CR_{11}R_{12}$), alkyne, amide (—$NR_9$—CO—), amine (—NH—, —$NR_8$—, or —$CR_9$—N—), carbonyl (—CO—), ether (—$CR_8$—O—), sulfonamide (—$NR_8$—$SO_2$—), sulfonate (—O—$SO_2$—), aryl (including optionally substituted aromatic heterocycles such as furans or benzo[b]furans, furanones, thiophenes or benzo[b]thiophenes, dioxazoles, imidazoles, indoles, indanes, indenes, lactams, naphthalenes, oxazoles, oxazolines, oxazolones, oxadiazolines, pyrazoles, thiazoles, thiophenes, triazoles, or tetrazoles), oxo (—O— or —$OR_8$—), thio (—S—), cycloalkyl, propanone (—(C=O)—$CR_8$=$CR_9$—), sulfonamide (—$NR_8$—(S=O)$_2$—), or sulfonate (—O—(S=O)$_2$—), wherein $R_8$, $R_9$, $R_{10}$, or $R_{11}$ are alternatively H, alkyl, amino, amido, cyano, hydroxyl, or carboxy. In an embodiment the compound is not combretastatin A1 or a salt, ester, or prodrug thereof.

In a second aspect, the present invention provides quinone compounds with enhanced therapeutic activity. In a preferred embodiment the quinone is an ortho-quinone. In a more preferred embodiment, the quinone is an anticancer agent; In a further preferred embodiment, the quinone is a tubulin binding agent. In a still further preferred embodiment, the quinone is a stilbene compound of one of the following general structures:

Ia:

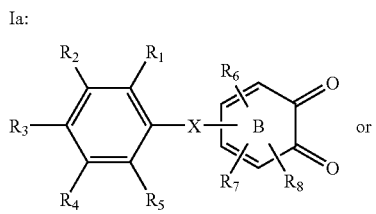

or

Ib:

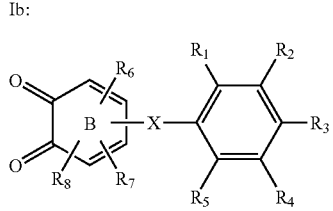

wherein at least one of $R_1$, $R_2$, $R_3$, $R_4$, $R_5$, $R_6$, $R_7$, or $R_8$ are the same or different and may be a $C_1$, $C_2$, $C_3$, $C_4$ or $C_5$ (preferably $C_1$) branched or straight-chain lower alkoxy, cycloalkoxy, heterocycloalkoxy, aryloxy, lower or alkanoyloxy; a halogen or trihaloalkyl; a $C_1$, $C_2$, $C_3$, $C_4$ or $C_5$ (preferably $C_1$) branched or straight chain lower alkyl, allyl, allyloxy, vinyl, or vinyloxy; OH, or a $C_1$, $C_2$, $C_3$, $C_4$ or $C_5$ (preferably $C_1$) primary, secondary, or tertiary alcohol; $NH_2$, or an amino, lower alkylamino, arylamino, aralkylamino, cycloalkylamino, heterocycloamino, aroylamino, aralkanoylamino, amido, lower alkylamido, arylamido, aralkylamido, cycloalkylamido, heterocycloamido, aroylamido, or aralkanoylamido; oxo, lower alkanoyl, thiol, sulfonyl, sulfonamide, nitro, nitrosyl, cyano, carboxy, carbamyl, aryl, or heterocyclo; and the remaining $R_1$, $R_2$, $R_3$, $R_4$, $R_5$, $R_6$, $R_7$ are H.

X may be alkene (—$CR_9$=$CR_{10}$—), alkane (—$CR_9$—$CR_{11}R_{12}$), alkyne, amide (—$NR_9$—CO—), amine (—NH—, —$NR_8$—, or —$CR_9$—N—), carbonyl (—CO—), ether (—$CR_8$—O—), sulfonamide (—$HR_8$—$SO_2$—), sulfonate (—O—$SO_2$—), aryl (including optionally substituted aromatic heterocycles such as furans or benzo[b]furans, furanones, thiophenes or benzo[b]thiophenes, dioxazoles, imidazoles, indoles, indanes, indenes, lactams, naphthalenes, oxazoles, oxazolines, oxazolones, oxadiazolines, pyrazoles, thiazoles, thiophenes, triazoles, or tetrazoles), oxo (—O— or —$OR_8$—), thio (—S—), cycloalkyl, propanone (—(C=O)—$CR_8$=$CR_9$—), sulfonamide (—$NR_8$—(S=O)$_2$—), or sulfonate (—O—(S=O)$_2$—), wherein $R_8$, $R_9$, $R_{10}$, or $R_{11}$ may alternatively be H, alkyl, amino, amido, cyano, hydroxyl, or carboxy.

In a preferred embodiment the X forms a covalent linkage between Ring A and B comprised of two contiguous atoms of the same or different element. In a more preferred embodiment, X is an ethylene group (—CH=CH—), Rings A and B are in a cis (Z) isomeric configuration, and $R_2$, $R_3$, and $R_4$ are all methoxy.

In another embodiment, the quinone is a bioreductive agent which is reductively activated in the body to form a catechol capable of participating in a Redox Cycling reaction to form one or more Reactive Oxygen Species ("ROS").

In a third aspect, the present invention provides catechol compounds with enhanced therapeutic activity. In a preferred embodiment the catechol is an ortho-catechol. In a more preferred embodiment, the catechol is an anticancer agent. In a further preferred embodiment, the catechol is a tubulin binding agent. In a still further preferred embodiment the catechol is a stilbene of the following general structures:

Ia:

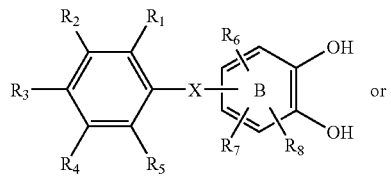

or

Ib:

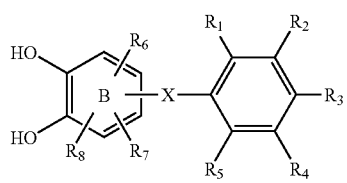

wherein at least one of $R_1$, $R_2$, $R_3$, $R_4$, $R_5$, $R_6$, $R_7$, or $R_8$ are the same or different and may be a $C_1$, $C_2$, $C_3$, $C_4$, $C_5$ (preferably $C_1$) branched or straight-chain lower alkoxy, cycloalkoxy, heterocycloalkoxy, aryloxy, or lower alkanoyloxy; a halogen or trihaloalkyl; a $C_1$, $C_2$, $C_3$, $C_4$, $C_5$ (preferably $C_1$) branched or straight chain lower alkyl, allyl, allyloxy, vinyl, or vinyloxy; OH, or a $C_1$, $C_2$, $C_3$, $C_4$, $C_5$ (preferably $C_1$) primary, secondary, or tertiary alcohol; $NH_2$, amino, lower alkylamino, arylamino, aralkylamino, cycloalkylamino, heterocycloamino, aroylamino, aralkanoylamino, amido, lower alkylamido, arylamido, aralkylamido, cycloalkylamido, heterocycloamido, aroylamido, or aralkanoylamido; oxo, lower alkanoyl, thiol, sulfonyl, sulfonamide, nitro, nitrosyl, cyano, carboxy, carbamyl, aryl, or heterocyclo; and the remaining $R_1$, $R_2$, $R_3$, $R_4$, $R_5$, $R_6$, $R_7$ may be H.

X may be alkene (—$CR_9$=$CR_{10}$—), alkane (—$CR_9$—$CR_{11}R_{12}$), alkyne, amide (—$NR_9$—CO—), amine (—NH—, —NR8—, or —$CR_9$—N—), carbonyl (—CO—), ether (—$CR_8$—O—), sulfonamide (—$NR_8$—$SO_2$—), sulfonate (—O—$SO_2$—), aryl (including optionally substituted aromatic heterocycles such as furans or benzo[b]furans, furanones, thiophenes or benzo[b]thiophenes, dioxazoles, imidazoles, indoles, indanes, indenes, lactams, naphthalenes, oxazoles, oxazolines, oxazolones, oxadiazolines, pyrazoles, thiazoles, thiophenes, triazoles, or tetrazoles), oxo (—O— or —$OR_8$—), amine (—NH— or —$NR_8$—), thio (—S—), cycloalkyl, propanone (—(C=O)—$CR_8$=$CR_9$), sulfonamide (—$NR_8$—(S=O)$_2$—), or sulfonate (—O—(S=O)$_2$—), wherein $R_8$, $R_9$, $R_{10}$, or $R_{11}$ may alternatively be H, alkyl, amino, amido, cyano, hydroxyl, or carboxy.

In a preferred embodiment X forms a covalent linkage between Ring A and B, wherein X includes two contiguous atoms of the same or different element. In a more preferred embodiment, X is an ethylene group (—CH=CH—), Rings A and B are in a cis (Z) iomeric configuration, and $R_2$, $R_3$, and $R_4$ are all methoxy.

In another preferred embodiment, the catechol has the structure (V):

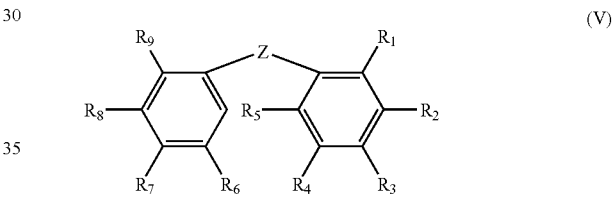

(V)

wherein Z may be an ethylene (—CH=CH—) bridge in the cis (Z) isomeric configuration; and $R_1$ and $R_2$ may be OH or a prodrug form thereof. At least one of $R_3$, $R_4$, $R_5$, $R_6$, $R_7$, $R_8$, and $R_9$ may be a $C_1$, $C_2$, $C_3$, $C_4$ or $C_5$ (preferably $C_1$) branched or straight-chain lower alkoxy, cycloalkoxy, heterocycloalkoxy, aryloxy, or lower alkanoyloxy; a halogen or trihaloalkyl; a $C_1$, $C_2$, $C_3$, $C_4$ or $C_5$ (preferably $C_1$) branched or straight chain lower alkyl, allyl, allyloxy, vinyl, or vinyloxy; OH, or a $C_1$, $C_2$, $C_3$, $C_4$ or $C_5$ (preferably $C_1$) primary, secondary, or tertiary alcohol; $NH_2$, amino, lower alkylamino, arylamino, aralkylamino, cycloalkylamino, heterocycloamino, aroylamino, aralkanoylamino, amido, lower alkylamido, arylamido, aralkylamido, cycloalkylamido, heterocycloamido, aroylamido, or aralkanoylamido; or oxo, lower alkanoyl, thiol, sulfonyl, sulfonamide, nitro, nitrosyl, cyano, carboxy, carbamyl, aryl, heterocyclo. The remaining $R_3$, $R_4$, $R_5$, $R_6$, $R_7$, $R_8$, and $R_9$ are may be hydrogen.

In another embodiment, the catechol is a biooxidative agent which is oxidative activated in the body to form a quinone which can participate in a redox cycling reaction and form one or more Reactive Oxygen Species.

In a fourth aspect, the present invention provides prodrug compounds of the aforementioned catechols and quinone compositions.

In a fifth aspect, the invention provides a method of inhibiting the proliferation of tumor cells in a patient bearing a solid tumor comprising administering to the patient an effective amount of a catechol or quinone compositon or a prodrug thereof.

In a preferred embodiment, the catechol or quinone composition is capable of forming Reactive Oxygen Species ("ROS") in a locality of the tumor, thereby directly inhibiting the proliferation of tumor cells.

In a sixth aspect, the invention provides a method of reducing bood flow in a patient suffering from a vascular proliferative disorder comprising administering to the patient an effective amount of a catechol compositon or a prodrug thereof.

In a preferred embodiment the reduction in blood flow causes the occlusion, destruction, or damage of proliferating vasculature in the patient.

In a more preferred embodiment, the effect of reduced blood flow is reversible so that blood flow is restored following cessation of compound administration.

In a seventh aspect, the invention provides a method of generating an enhanced anti-tumor effect in a patient bearing a solid tumor comprising the administration of an effective amount of a catechol or prodrug thereof which is capable of both inhibiting the proliferation of tumor cells and reducing the flow of blood to at least a portion of the tumor.

In yet another aspect, the invention provides the use of a catechol composition or a prodrug composition thereof, for use as an antimicrotubule agent.

DETAILED DESCRIPTION OF THE INVENTION

Definitions

Figure 1A:
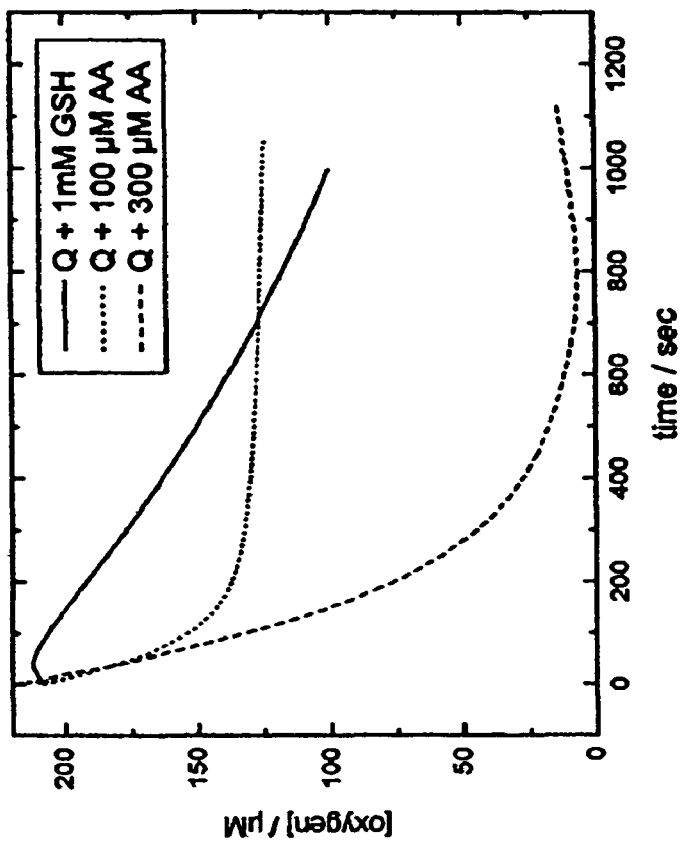
FIG. 1A illustrates the loss of absorbance of Combretastatin A-1 ortho-quinone on mixing with a reducing agent.

As used herein, the following terms in quotations shall have the indicated meanings, whether in plural or singular form.

"Alkyl" when used alone or in combination with other groups, includes lower alkyl containing from 1 to 8 carbon atoms and may be straight chained or branched. An alkyl group includes optionally substituted straight, branched or cyclic saturated hydrocarbon groups. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include, but are not limited to one or more of the following groups: halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—HHCOOR— or —OCONHR—), urea (—HHCONHR—) or thiol (—SH). Alkyl groups as defined may also comprise one or more carbon-carbon double bonds or one or more carbon-carbon triple bonds.

Preferred alkyl groups contain 1-8 carbon atoms; more preferred alkyl groups contain 1-6 carbon atoms. Alkylene as used herein includes a bridging alkyl group of the formula $C_nH_{2n}$. Examples include $CH_2$, —$CH_2CH_2$—, —$CH_2CH_2CH_2$— and the like.

As used herein the term "cycloalkyl" is a species of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

"Aryl" refers to groups with aromaticity, including 5- and 6-membered single-ring aromatic groups that may include from zero to four heteroatoms, as well as multicyclic systems with at least one aromatic ring. Examples of aryl groups include benzene, phenyl, heterocyclic groups (pyrrole, furan, thiophene, thiazole, isothiazole, imidazole, indole, morpholine, triazole, thiene, tetrazole, pyrazole, oxadiozole, oxazole, isooxazole, piperidine, pyridine, pyrazine, pyridazine, and pyrimidine, and the like), bicyclic heterocyclic groups (benzothiazole, benzothiene, quinoline, isoquinoline, benzaimidazole, benzopyrane, indolizine, benzofuran, chromine, courmain, cinnoline, quinoxaline, indazole, pyrrolopyridine, furopyridine, naphthalene, dihydroisoindoline, dihydroquinazoline, benzisothiazole, benzopyrazole, dihydrobenzofurane, dihydrobenzothiene, dihydronaphthalene, dihydrobenzopyrane, phthalazine, purine, and the like), and polycyclic groups (anthracene, phenanthrene, chrysene, and the like). The aromatic ring can be substituted at one or more ring positions with such substituents as described above, as for example, halogen, hydroxyl, alkoxy, etc. The preferred aryl group of the present invention is a benzene ring.

"Cancer", "Neoplastic Disease", and "Tumor" shall be used interchangeably and shall refer to the abnormal presence of cells which exhibit relatively autonomous growth, so that they exhibit an aberrant growth phenotype characterized by a significant loss of cell proliferation control. Cancerous cells can be benign or malignant. In various embodiments, the cancer affects cells of the bladder, blood, brain, breast, colon, digestive tract, lung, ovaries, pancreas, prostate gland, thyroid, or skin.

a) solid carcinomas, including cancers of the lung (such as small cell lung cancer, non-small cell lung cancer, and lung adenocarcinoma), colon (including colorectal cancer), ovaries, prostrate, testes, cervix, genitourinary tract, bladder (including accelerated and metastatic bladder cancer), liver, larynx, esophagus, stomach, breast, kidney, gall bladder, thyroid, pancreas (including exocrine pancreatic carcinoma), and skin (including squamous cell carcinoma);

b) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;
c) hematopoietic tumors of myeloid lineage, including acute and chronic myelogenous leukemias, myelodysplastic syndrome, and promyelocytic leukemia;
d) tumors of mesenchymal origin, including fibrosarcoma, osteosarcoma and rhabdomyosarcoma;
e) tumors of the central and peripheral nervous system, including astrocytoma, neuroblastoma, glioma and schwannomas; and
f) other tumors, including melanoma, seminoma, teratocarcinoma, osteosarcoma, xenoderoma pigmentosum, keratoactanthoma, thyroid follicular cancer, medullary thyroid cancer, anaplastic thyroid cancer, teratocarcinoma, and Kaposi's sarcoma.

"Antiproliferative" refers to the ability of the compounds of the present invention to directly inhibit tumor cells from multiplying. In general, the antiproliferative activity of the compositions of the invention fall into two classes, anti-proliferative cytotoxic and anti-proliferative cytostatic. Cytotoxic agents prevent tumor cells from multiplying by: (1) directly interfering with the ability of tumor cells to replicate DNA or undergo mitotic cell division and (2) inducing cell death and/or apoptosis in the cancer cells. Anti-proliferative cytostatic or quiescent agents act via modulating, interfering or inhibiting the processes of cellular signal transduction which regulate cell proliferation in order to slow the rate of cell division or tumor growth so that the cells become non-proliferative or so that their behavior approximates that of non-proliferative cells.

"Catechol" is any group of optionally substituted compounds with aryl functionality and containing at least two OH groups the ortho position or para position on the Aryl ring, wherein a conjugated system is formed with at least one C=C bond. The preferred catechol of the present invention is an ortho-benzocatechol.

"Effective Amount" shall be an amount of drug which generates a significant anti-tumor effect including but not limited to, inhibition of tumor growth, tumor growth delay, tumor regression, tumor shrinkage, increased time to regrowth of tumor on cessation of treatment, and slowing of disease progression. It is expected that when a method of treatment of the present invention is administered to a patient in need of treatment for cancer, said method of treatment will produce an effect, as measured by, for example, one or more of: the extent of the anti-tumor effect, the response rate, the time to disease progression, and the survival rate.

"Halogen" or "Halo" refers to chlorine, bromine, fluorine or iodine.

"Lower alkoxy" refers to —O-alkyl groups, wherein alkyl is as defined hereinabove. The alkoxy group is bonded to the main chain, aryl or heteroaryl group through the oxygen bridge. The alkoxy group may be straight chained or branched; although the straight-chain is preferred. Examples include methoxy, ethyloxy, propoxy, butyloxy, t-butyloxy, i-propoxy, and the like. Preferred alkoxy groups contain 1-4 carbon atoms, especially preferred alkoxy groups contain 1-3 carbon atoms. The most preferred alkoxy group is methoxy.

"Lower alkylamino" refers to a group wherein one alkyl group is bonded to an amino nitrogen, i.e., NH(alkyl). The NH is the bridge connecting the alkyl group to the aryl or heteroaryl. Examples include NHMe, NHEt, NHPr, and the like.

"Proliferating Vasculature" refers to either a tumor vasculature or non-malignant proliferating vasculature, otherwise known as neovasculature or immature vasculature, which supply blood to tumors or normal tissues for the provision of oxygen and nutrients. Proliferating vasculature exhibits structural and functional features that distinguishes it from normal vasculature, including irregular vessel diameter, leakiness, vessel tortuosity, thin vessel wall thickness, heterogeneous blood flow distribution, high interstitial fluid pressure, procoagulant status, or small numbers of supportive cells.

"Quinone" is any group of optionally substituted aromatic polyketone compounds derived from a compound with an Aryl moeity. At least two C=O groups are in the ortho or para position on the Aryl ring, and form a conjugated system with at least one C=C bond. The preferred quinone of the present invention is an ortho-benzoquinone. quinones synthesized in a number of ways by oxidation of a phenolic precursor such as ortho-catechol. The oxidant reagents used in the reaction can include Jones reagent (Chromate salts), Fremy's salt ($(KSO_3)_2$ NO), and the like. The preferred oxidant is o-iodoxybenzoic acid.

"Salt" is a pharmaceutically acceptable salt, i.e., substantially non-toxic and with the desired pharmacokinetic properties, palatability, and solubility, and can include acid addition salts including amino acids, hydrochlorides, hydrobromides, phosphates, sulphates, hydrogen sulphates, alkylsulphonates, arylsulphonates, acetates, ascorbates, benzoates, citrates, glycolates, maleates, nitrates, fumarates, stearates, salicylates, succinates, oxalates, lactates, and tartrates; alkali metal cations such as Na, K, Li, alkali earth metal salts such as Mg or Ca; or organic bases dicyclohexylamine, trbutylamine, pyridine, triethylamine, and as others disclosed in PCT International Application Nos. WO02/22626 or WO00/48606. The salts of the present invention can be synthesized by conventional chemical methods. Generally, the salts are prepared by reacting the free base or acid with stoichiometic amounts or with an excess of the desired salt-forming inorganic or oganic acid or base, in a suitable solvent or solvent combination.

"Tubulin Binding Agent" shall refer to a ligand of tubulin or a compound capable of binding α or β-tubulin monomers, αβ-tubulin heterodimers, or polymerized microtubules and interfering with the polymerization or depolymerization of microtubules. The exact nature of tubulin binding site interactions remain largely unknown, and they definitely vary between each class of Tubulin Binding Agent. Photoaffinity labeling and other binding site elucidation techniques have identified three key binding sites: 1) the Colchicine site (Floyd et al, Biochemistry, 1989; Staretz et al, J. Org. Chem., 1993; Williams et al, J. Biol. Chem., 1985; Wolff et al, Proc. Natl. Acad. Sci. U.S.A., 1991), 2) the Vinca Alkaloid site (Safa et al, Biochemistry, 1987), and 3) a site on the polymerized microtubule to which taxol binds (Rao et al, J. Natl. Cancer Inst., 1992; Lin et al, Biochemistry, 1989; Sawada et al, Bioconjugate Chem, 1993; Sawada et al, Biochem. Biophys. Res. Commun., 1991; Sawada et al, Biochem. Pharmacol., 1993). Tubulin binding agents contemplated by the present invention contain at least one aryl moiety where a catechol or quinone structure can be introduced in order to generate a "Dual activity" agent. Particularly preferred tubulin binding agents include:

a) Combretastatins or other stilbene analogs (Pettit et al, Can. J. Chem., 1982; Pettit et al, J. Org. Chem., 1985; Pettit et al, J. Nat. Prod., 1987; Lin et al, Biochemistry, 1989; Singh et al, J. Org. Chem., 1989; Cushman et al, J. Med. Chem., 1991; Getahun et al, J. Med. Chem., 1992;

Andres et al, Bioorg. Med. Chem. Lett., 1993; Mannila, Liebigs. Ann. Chem., 1993; Shirai et al, Bioorg. Med. Chem. Lett., 1994; Medarde et al., Bioorg. Med. Chem. Lett., 1995; Pettit et al, J. Med. Chem., 1995; Wood et al, Br. J. Cancer., 1995; Bedford et al, Bioorg. Med. Chem. Lett., 1996; Dorr et al, Invest. New Drugs, 1996; Jonnalagadda et al., Bioorg. Med. Chem. Lett., 1996; Shirai et al, Heterocycles, 1997; Aleksandrzak K, Anticancer Drugs, 1998; Chen et al, Biochem. Pharmacol., 1998; Ducki et al, Bioorg. Med. Chem. Lett., 1998; Hatanaka et al, Bioorg. Med. Chem. Lett., 1998; Medarde, Eur. J. Med. Chem., 1998; Medina et al, Bioorg. Med. Chem. Lett., 1998; Ohsumi et al, Bioorg. Med. Chem. Lett., 1998; Ohsumi et al., J. Med. Chem., 1998; Pettit G R et al., J. Med. Chem., 1998; Shirai et al, Bioorg. Med. Chem. Lett., 1998; Banwell et al, Aust. J. Chem., 1999; Medarde et al, Bioorg. Med. Chem. Lett., 1999; Shan et al, PNAS, 1999; Combeau et al, Mol. Pharmacol, 2000; Pettit et al, J. Med Chem, 2000; Pettit et al, Anticancer Drug Design, 2000; Pinney et al, Bioorg. Med. Chem. Lett., 2000; Flynn et al., Bioorg. Med. Chem. Lett., 2001; Gwaltney et al, Bioorg. Med. Chem. Lett., 2001; Lawrence et al, 2001; Nguyen-Hai et al, Bioorg. Med. Chem. Lett., 2001; Xia et al, J. Med. Chem., 2001; Tahir et al., Cancer Res., 2001; Wu-Wong et al., Cancer Res., 2001; Janik et al, Bioorg. Med. Chem. Lett., 2002; Kim et al, Bioorg Med Chem Lett., 2002; Li et al, Bioorg. Med. Chem. Lett., 2002; Nam et al, Bioorg. Med. Chem. Lett., 2002; Wang et al, J. Med. Chem. 2002; Hsieh et al, Biooorg. Med. Chem. Lett., 2003; Hadimani et al., Bioorg. Med. Chem. Lett., 2003; Mu et al, J. Med. Chem, 2003; Nam, Curr. Med. Chem., 2003; Pettit et al, J. Med. Chem., 2003; WO 02/50007, WO 02/22626, WO 02/14329, WO 01/81355, WO 01/12579, WO 01/09103, WO 01/81288, WO 01/84929, WO 00/48591, WO 00/48590, WO 00/73264, WO 00/06556, WO 00/35865, WO 00/48590, WO 99/51246, WO 99/34788, WO 99/35150, WO 99/48495, WO 92/16486, U.S. Pat. Nos. 6,433,012, 6,201,001, 6,150,407, 6,169,104, 5,731,353, 5,674,906, 5,569,786, 5,561,122, 5,430,062, 5,409,953, 5,525,632, 4,996,237 and 4,940,726 and U.S. patent application Ser. No. 10/281,528);

b) 2,3-substituted Benzo[b]thiophenes (Pinney et al, Bioorg. Med. Chem. Lett., 1999; Chen et al, J. Org. Chem., 2000; U.S. Pat. Nos. 5,886,025; 6,162,930; and 6,350,777; WO 98/39323);

c) 2,3-disubstituted Benzo[b]furans (WO 98/39323, WO 02/060872);

d) Disubstituted Indoles (Gastpar R, J. Med. Chem., 1998; Bacher et al, Cancer Res., 2001; Flynn et al, Bioorg. Med. Chem. Lett, 2001; WO 99/51224, WO 01/19794, WO 01/92224, WO 01/22954; WO 02/060872, WO 02/12228, WO 02/22576, and U.S. Pat. No. 6,232,327);

e) 2-Aroylindoles (Mahboobi et al, J. Med. Chem., 2001; Gastpar et al., J. Med. Chem., 1998; WO 01/82909)

f) 2,3-disubstituted Dihydronaphthalenes (WO 01/68654, WO 02/060872);

g) Benzamidazoles (WO 00/41669);

h) Chalcones (Lawrence et al, Anti-Cancer Drug Des, 2000; WO 02/47604)

i) Colchicine, Allocolchicine, Thiocolcichine, Halichondrin B, and Colchicine derivatives (WO 99/02166, WO 00/40529, WO 02/04434, WO 02/08213, U.S. Pat. Nos. 5,423,753. 6,423,753) in particular the N-acetyl colchinol prodrug, ZD-6126;

j) Curacin A and its derivatives (Gerwick et al, J. Org. Chem., 1994, Blokhin et al, Mol. Pharmacol., 1995; Verdier-Pinard, Arch. Biochem. Biophys., 1999; WO 02/06267);

k) Dolastatins such as Dolastatin-10, Dolastatin-15, and their analogs (Pettit et al, J. Am. Chem. Soc., 1987; Bai et al, Mol. Pharmacol, 1995; Pettit et al, Anti-Cancer Drug Des., 1998; Poncet, Curr. Pharm. Design, 1999; WO 99/35164; WO 01/40268; U.S. Pat. No. 5,985,837);

m) Epothilones such as Epothilones A, B, C, D and Desoxyepothilones A and B (WO 99/02514, U.S. Pat. No. 6,262,094, Nicolau et al., Nature, 1997);

n) Inadones (Leoni et al., J. Natl. Cancer Inst., 2000; U.S. Pat. No. 6,162,810);

o) Lavendustin A and its derivatives (Mu F et al, J. Med. Chem., 2003);

p) 2-Methoxyestradiol and its derivatives (Fotsis et al, Nature, 1994; Schumacher et al, Clin. Cancer Res., 1999; Cushman et al, J. Med. Chem., 1997; Verdier-Pinard et al, Mol. Pharmacol, 2000; Wang et al, J. Med. Chem., 2000; WO 95/04535, WO 01/30803, WO 00/26229, WO 02/42319 and U.S. Pat. Nos. 6,528,676, 6,271,220, 5,892,069, 5,661,143, and 5,504,074);

q) Monotetrahydrofurans ("COBRAs"; Uckun, Bioorg. Med. Chem. Lett., 2000; U.S. Pat. No. 6,329,420);

r) Phenylhistin and its derivatives (Kanoh et al, J. Antibiot., 1999; Kano et al, Bioorg. Med. Chem., 1999; U.S. Pat. No. 6,358,957);

s) Podophyllotoxins such as Epidophyllotoxin (Hammonds et al, J. Med. Microbiol, 1996; Coretese et al, J. Biol. Chem., 1977);

t) Rhizoxins (Nakada et al, Tetrahedron Lett., 1993; Boger et al, J. Org. Chem., 1992; Rao, et al, Tetrahedron Lett., 1992; Kobayashi et al, Pure Appl. Chem., 1992; Kobayashi et al, Indian J. Chem., 1993; Rao et al, Tetrahedron Lett., 1993);

u) 2-strylquinazolin-4(3H)-ones ("SQOs", Jiang et al, J. Med. Chem., 1990);

v) Spongistatin and Synthetic spiroketal pyrans ("SPIKETs"; Pettit et al, J. Org. Chem., 1993; Uckun et al, Bioorgn. Med. Chem. Lett., 2000; U.S. Pat. No. 6,335,364, WO 00/00514);

w) Taxanes such as Paclitaxel (Taxol®), Docetaxel (Taxotere®), and Paclitaxel derivatives (U.S. Pat. No. 5,646,176, WIPO Publication No. WO 94/14787, Kingston, J. Nat. Prod., 1990; Schiff et al, Nature, 1979; Swindell et al, J. Cell Biol., 1981);

x) Vinca Alkaloids such as Vinblastine, Vincristine, Vindesine, Vinflunine, Vinorelbine (Navelbine®) (Owellen et al, Cancer Res., 1976; Lavielle et al, J. Med. Chem., 1991; Holwell et al, Br. J. Cancer., 2001); or y) Welwistatin (Zhang et al, Molecular Pharmacology, 1996).

Many tubulin binding agents have been known to disrupt tumor vasculature but differ in that they also manifest substantial normal tissue toxicity at their maximum tolerated dose. In contrast, genuine VTAs retain their selective tumor vascular shutdown activity at a fraction of their maximum tolerated dose, with minimal effects on normal tumor vasculature. Although tubulin binding agents in general can mediate effects on tumor blood flow, doses that are effective are often also toxic to other normal tissues and not particularly toxic to tumors (Br. J. Cancer 74(Suppl. 27):586-88, 1996). For example, the vascular effects that are observed with colchicines and vinca alkaloids are only evident at doses approximating or surpassing the maximum tolerable dose to the patient (Baguley et al., Eur. J. Cancer., 27(4): 482-487; Hill et al., Eur. J. Cancer, 29A(9): 1320-1324.)

"Tumor microvessel" refers to the endothelium, artery or blood vessel, also known as tumor neovasculature, feeding any type of tumor, whether it be malignant, benign, actively growing, or in remission.

Compositions:

All stereoisomers of the compounds of the instant invention are contemplated, either in admixture or in pure or substantially pure form. The definition of the compounds according to the invention embraces all possible stereoisomers and their mixtures. It particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be noted that any heteroatom with unsatisfied valences is assumed to have the hydrogen atom to satisfy the valences.

When a group is referred to as being "Optionally substituted", it may be substituted with one to five, preferably one to three, substituents such as halogen, alkyl, hydroxyl, lower alkoxy, Amino, Lower alkylamino, cycloalkoxy, heterocycloalkoxy, oxo, lower alkanoyl, aryloxy, lower alkanoyloxy, arylamino, aralkylamino, cycloalkylamino, heterocycloamino, aroylamino, aralkanoylamino, thiol, sulfonyl, sulfonamide, nitro, nitrosyl, cyano, carboxy, carbamyl, aryl, heterocyclo, and the like.

a) Quinones

The quinones of the present invention were found to participate in a Redox Cycling Reaction and stimulate oxidative stress in tumor cells by the concomitant production of ROS that are directly toxic to tumor cells. In addition, the quinone and semiquinone molecules generated by the oxidation of the catechol may themselves cause tumor cell death by direct cytotoxic mechanisms including membrane damage, lipid peroxidation, and depolymerization of macromolecules. These highly reactive species of catechol can elicit their damage to tumor cells by binding to proteins, lipids, or nucleic acids.

A Redox Cycling Reaction or Oxidation-Reduction reaction is in equilibrium between reduction (increase in electrons) or oxidation (loss of electrons) as illustrated with the following reaction in which ortho-benzoquinone, formed by dephosphorylation of a prodrug, is reductively activated to form its corresponding ortho-catechol which in turn can be oxidized to regenerate the ortho-quinone.

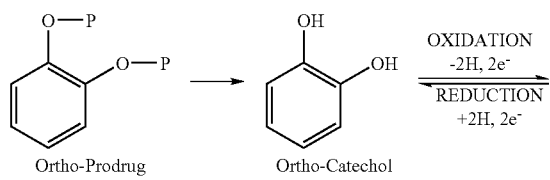

Ortho-Prodrug     Ortho-Catechol

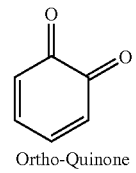

Ortho-Quinone

A reduction is facilitated by the oxidation of a reducing agent (electron donor) while oxidation is facilitated by the reduction of an oxidizing agent (electron acceptor).

The quinones of the present invention can be reduced or reductively activated by the presence of a reducing agent such as NADH, NADPH, Ascorbate, Glutathione or reducing enzymes such as the flavoenzyme DT-diaphorase which is highly expressed in many tumor cells.

Oxidative stress induced by the quinones of the present invention is due to the quinone itself or by the formation of Reactive Oxygen Species (ROS) which include Semiquinone radical anion ($Q^{*-}$), $$\text{catechol} + \text{Reducing Agent} \rightarrow Q^{*-} + H^+ + e^- \quad (1)$$

Superoxide radicals ($O_2^{*-}$), $$Q^{*-} + O_2 \rightarrow Q + O_2^{*-} \quad (2)$$

Hydrogen peroxide ($H_2O_2$),

$$2\,O_2^{*-} + 2\,H^+ \rightleftharpoons H_2O_2 \quad (3)$$

or hydroxyl radicals ($OH^{*-}$), if trace heavy metals are present to catalyze their formation from Hydrogen peroxide.

$$H_2O_2 + \text{Reduced Iron/Copper} \rightleftharpoons {}^{*-}OH + \text{Oxidized Iron/Copper} \quad (4)$$

ROS are directly cytotoxic to tumor cells because they react directly to form adducts with cell components including protein, lipid, and DNA. Alternatively, they can initiate the formation of lipid hydroperoxides which in turn act as mutagens by covalently modifying DNA. Hydroxyl anion radicals, for example, are some of the most powerful oxidants in biological systems and can mediate many destructive mechanisms on tumor cells, including membrane damage, lipid peroxidation, and depolymerization of macromolecules.

b) Catechols

Catechols of the present invention can be used to generate one or both of the following toxic effects. In the first toxic effect, the catechol compound is able to selectively target endothelial cells of tumor vasculature or other proliferating vasculature and reduce the flow of blood within the proliferating vasculature. The reduction in blood flow can result in damage or regression of the proliferating vasculature and/or inhibition of further vascular proliferation. When administered to an patient bearing a solid tumor, this first toxic effect can result in tumor hypoxia and nutrient deprivation. In the second toxic effect, the catechol is used as a cytotoxic agent which forms its corresponding quinone in vivo and is able to kill tumor cells directly by inducing oxidative stress. In a particularly preferred embodiment, the catechol is a "dual activity" agent capable of eleciting both the first and second toxic effect.

Catechols of the present invention can be activated to form corresponding quinones by the presence of an "oxidizing agent or equivalent", such as Oxygen or enzymes such as myeloperoxidases or tyrosinases, to form a catechol radical ($C^{*-}$). Formation of the catechol radical establishes a redox cycle in which the production of ROS is amplified multiple times. This is because two catechol radicals can generate an ortho quinone and regenerate the ortho-catechol which can react again to supply additional reactive catechol radicals. Reduction of the quinone by a reducing agent such as NADPH or the enzyme DT-Diaphorase (NADPH quinone-acceptor oxidoreductase), regenerates the original catechol and establishes a redox cycle, which amplifies the formation of ROS.

Catechols thought to be involved in the generation of ROS through redox cycling include:
1) Diols of Polycyclic Aromatic Hydrocarbons (PAH) such as Naphthalene diols, Benz[alpha]anthracene diols, Chrysene diols, Phenanthrene diols, Benz[a]pyrene diols (Sridhar, Tetrahedron, 2001; Flowers-Geary, Chem Biol Interact, 1996), including Menadione.
2) Catechol estrogens or antiestrogens such as 3,4 Dihydroxytamoxifen, Toremifine, Droloxifine, (Bolton, Toxicology, 2002; Chem Res. Toxicol, 2000).
3) Topoisomerase II inhibitors such as Etoposide catechol (Pang, J. of Mass Spec, 2001).

Figure 3:
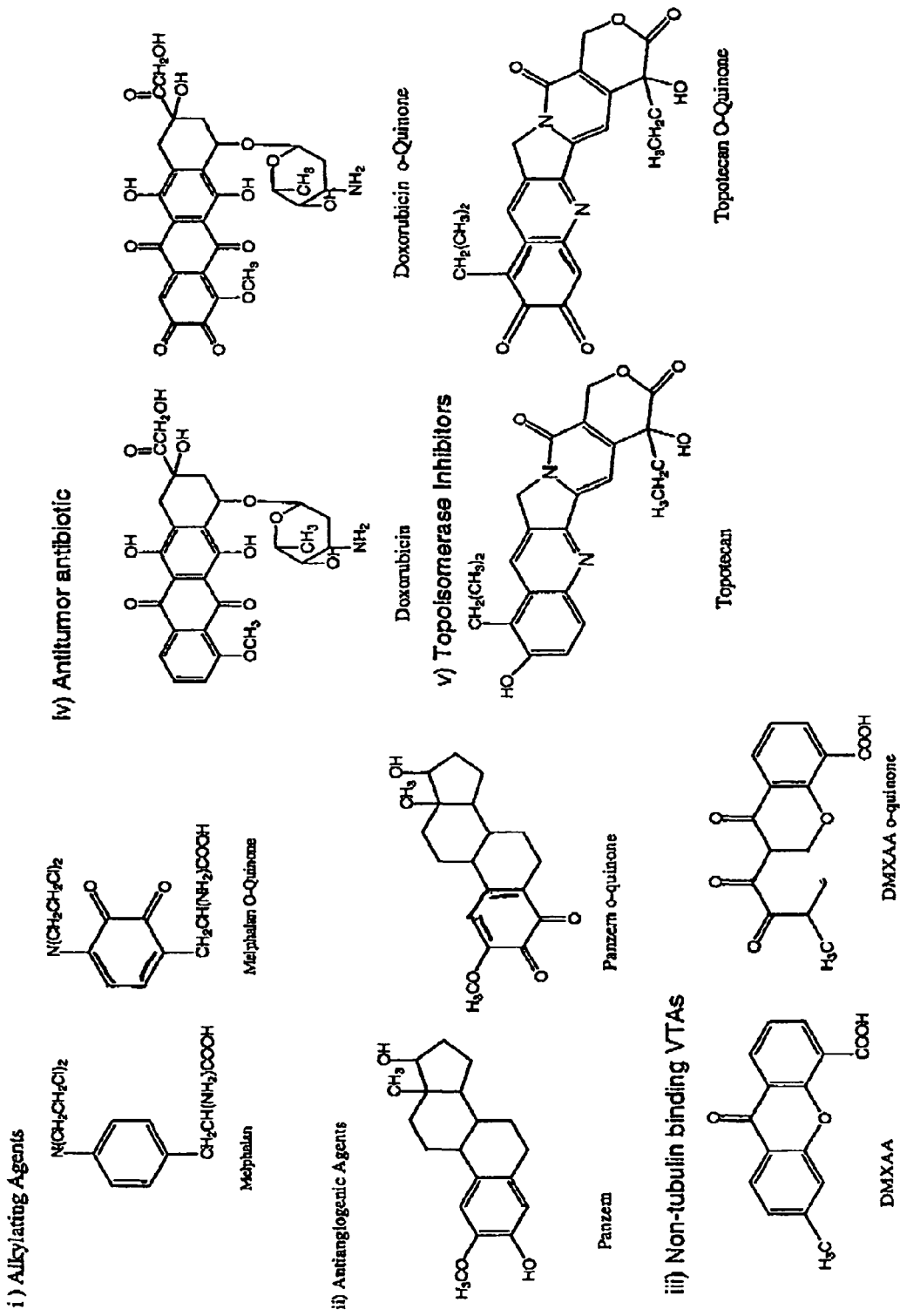
FIG. 3 illustrates exemplary catechols, their corresponding quinones, and prodrugs of these catechols.
Figure 4:
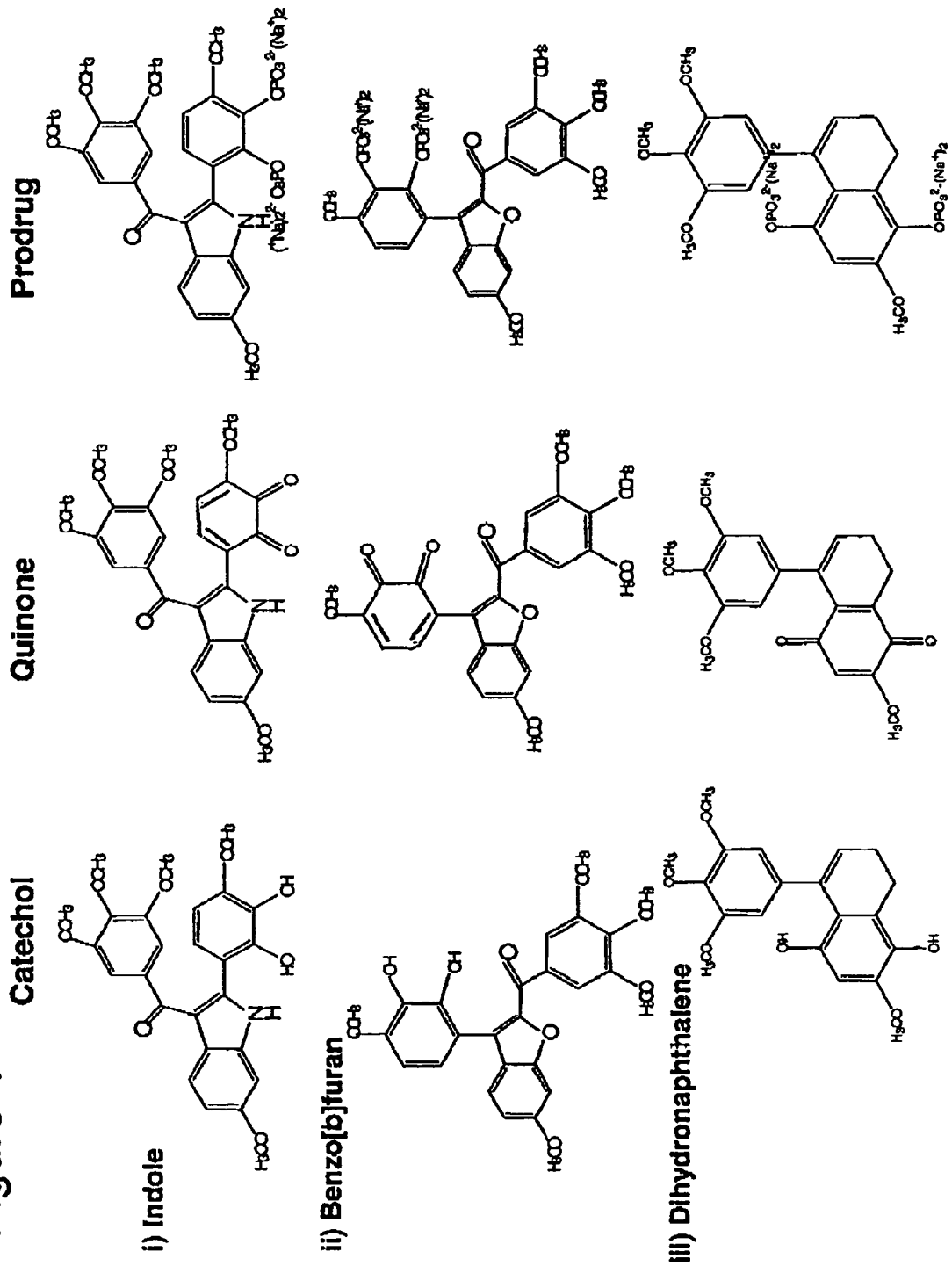
FIG. 4 illustrates exemplary Tubulin Binding Agents, their corresponding quinones and prodrugs of these catechols.

Anticancer agents for use in the present invention contain an aryl functionality and include the following compounds which are classified based on the mechanism of action:
1. Alkylating agents: compounds that donate an alkyl group to nucleotides. Alkylated DNA is unable to replicate itself and cell proliferation is stopped. Exemplary alkylating agents include Melphalan and Chlorambucil. The structure of Melphalan and its corresponding o-quinone are depicted in FIG. 3.
2. Antiangiogeneic agents: compounds that inhibit the formation of tumor vasculature. The structure of an exemplary Alkylating agent, and its corresponding o-quinone are depicted in FIG. 3.
3. Antitumor Antibiotics: compounds having antimicrobial and cytotoxic activity. Such compounds also may interfere with DNA by chemically inhibiting enzymes and mitosis or altering cellular membranes. Exemplary antitumor antibiotics include Dactinomycin, Daunorubicin, and Doxorubicin. The structure of Doxorubicin, and its corresponding o-quinone, are depicted in FIG. 3.
4. Topoisomerase Inhibitors: agents which interfere with topoisomerase activity thereby inhibiting DNA replication. Such agents include CPT-11 and Topotecan. The structure of Topotecan and its corresponding o-quinone is depicted in FIG. 3.
5. Hormonal Therapy: includes, but is not limited to antiestrogens. An exemplary antiestrogen is Tamoxifen.
6. Mitotic inhibitors: compounds that inhibit mitosis or inhibit enzymes that prevent protein synthesis needed for reproduction of the cell. Preferred mitotic inhibitors are tubulin binding agents. The structure of representative exemplary tubulin binding agents, and their corresponding o-quinones, are depicted in FIG. 4.

c) Prodrugs
i) Catechol Prodrugs. Prodrugs of the present invention are precursor forms of catechols that are metabolically converted in vivo to produce corresponding catechols. In an important specific sense, to which however the invention is in its broadest aspects not limited, the prodrug in the foregoing methods, compositions and procedures may be a Phosphate within the class of compounds having the general formula

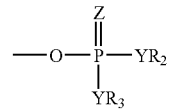

wherein
Y is O, NH, S, O⁻, NH⁻ or S⁻;
Z is O or S; and
each of $R^2$ and $R^3$ is an alkyl group, H, a monovalent or divalent metal cationic salt, or an ammonium cationic salt, and $R^2$ and $R^3$ may be the same or different.

Currently preferred prodrugs for the practice of the invention are those having the following formulae:

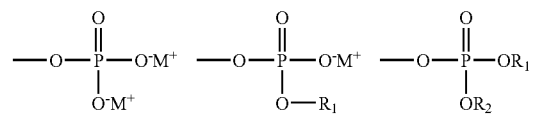

Other prodrugs contemplated for use in the present invention include Sulphates of the following general formula

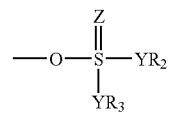

wherein
Y is O, NH, S, O⁻, NH⁻ or S⁻;
Z is O or S;
each of $R^2$ and $R^3$ is an alkyl group, H, a monovalent or divalent metal cationic salt, or an ammonium cationic salt, and $R^2$ and $R^3$ may be the same or different.

Prodrugs of catechols can also be activated to the corresponding catechol in vivo by the action of non-specific phosphatases, sulphatases or other metabolic enzymes. The corresponding catechol will be oxidative activated by an oxidizing agent or enzyme.

ii) Quinone Prodrugs. Since quinone drugs are highly unstable, conversion of a quinone to a corresponding prodrug form has the advantage of creating a stable molecule which is activated to regenerate the quinone in vivo by the action of non-specific phosphatases, sulphatases or other metabolic enzymes. Classes of drugs which contain the quinone moiety and which can be stabilized in phosphorylated prodrug form include:
1) Alkylating agents (Begleiter, Front. Biosci, 2000; Workman, Oncol. Res., 1994)—do not bind to DNA but intercalate into it resulting in changes in DNA replication. Anthracyclines such as Doxorubicin (Adriamycin), Mitomycin C, Porfiromycin, Diaziquone, Carbazilquinone, triaziquone, indoloquinone EO9, diaziridinyl-benzoquinone methyl DZQ, Anthracenediones, and Aziridines
2) DNA topoisomerase II inhibitors including Lapachones such as Beta-Lapachone (U.S. Pat. Nos. 5,969,163, 5,824,700, and 5,763,625)
3) Antibiotic compounds such as the Mitoxantrone, Actinomycin, Ansamycin benzoquinones and quinonoid derivatives including the Quinolones, Genistein, Bactacyclin, 4) Furanonapthoquinone derivatives and other naphthoquinones and naphtha-[2,3-d]-imidazole-4,9-dione compounds.

Therapeautic Treatments

The inventors have made the surprising discovery that certain catechol-containing compounds and their prodrugs have superior in vivo activity relative to CA4P and other monophenol containing compounds, both in terms of vascular toxicity and antitumor growth delay. For example, the inventors discovered that diphosphate analog of CA4P, Combretastatin A-1 diphosphate ("CA1P", 3), together with its corresponding catechol Combretastatin A-1 ("CA-1", 2) which have the following structures:

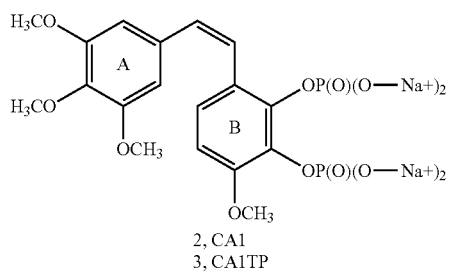

2, CA1
3, CA1TP are capable of generating an enhanced antitumor response by forming ROS in the locality of the tumor and/or selectively reducing the flow of blood to at least a portion of a tumor region, thereby both directly inhibiting the proliferation of tumor cells and selectively causing hypoxia and subsequent necrosis in a portion of the tumor tissue without substantial necrosis of non-tumor tissue in adjoining regions. It was observed that CA1P has the superior property of improved potency at several dosages. In addition, it was discovered that CA1P possesses the advantageous property of achieving significant tumor growth retardation when used as a single agent. This is particularly surprising when it is considered that CA1P has inferior antiproliferative activity against tumor cells in vitro, in comparison to CA4P. However, CA4P induces little growth retardation when administered in a single dose that is close to or at its maximum tolerated dose. This lack of single agent activity has been attributed to the survival of a rim of peripheral tumor cells adjacent to the more normal vasculature in the surrounding tissue. This viable rim of cells rapidly proliferates and contributes to the regrowth and revascularization of the tumor tissue in the core of the tumor. Therefore, CA4P has the disadvantage that it must be combined with another antitumor agent in order to achieve significant tumor regression.

An object of the present invention is a method of producing an anti-tumor effect in a patient bearing a solid tumor comprising the administration of an effective amount of a quinone, catechol, or Prodrug thereof. Anti-proliferative effects of a method of treatment of the present invention include but are not limited to: inhibition or delay of tumor cell growth or proliferation, or growth delay. These effects include tumor regression, tumor shrinkage, increased time to regrowth of tumor on cessation of treatment, and slowing of disease progression. It is expected that when a method of treatment of the present invention is administered to a patient in need of treatment for cancer, said method of treatment will produce an effect, as measured by, for example, one or more of: the extent of the anti-tumor effect, the response rate, the time to disease progression, and the survival rate.

In one embodiment, the compounds of the present invention may be used as antimicrotubule agents. Microtubules, cellular organelles present in all eukaryotic cells, are required for healthy, normal cellular activities. They are an essential component of the mitotic spindle needed for cell division, and are required for maintaining cell shape and other cellular activities such as motility, anchorage, transport between cellular organelles, extracellular secretory processes (Dustin, P. (1980) Sci. Am., 243: 66-76), as well as modulating the interactions of growth factors with cell surface receptors, and intracellular signal transduction. Furthermore, microtubules play a critical regulatory role in cell replication as both the c-mos oncogene and CDC-2-kinase, which regulate entry into mitosis, bind to and phosphorylate tubulin (Verde, F. et al. (1990) Nature, 343:233-238), and both the product of the tumor suppressor gene, p53, and the T-antigen of SV-40 bind tubulin in a ternary complex (Maxwell, S. A. et al. (1991) Cell Growth Differen., 2:115-127). Microtubules are not static, but are in dynamic equilibrium with their soluble protein subunits, the α- and β-tubulin heterodimers. Assembly under physiologic conditions requires guanosine triphosphate (GTP) and certain microtubule associated and organizing proteins as cofactors; on the other hand, high calcium and cold temperature cause depolymerization. Interference with this normal equilibrium between the microtubule and its subunits would therefore be expected to disrupt cell division and motility, as well as other activities dependent on microtubules.

When used as an anti-cancer agent, the compounds of the present invention can be formulated as a single composition or they may contain additional therapeutic agents, such as anti-cancer agents. Such therapeutic agents include, for example, a chemotherapeutic agent, an alkylating agent, a purine or pyrimidine analog, a vinca or vinca-like alkaloid, an etoposide or etoposide-like drug, an antibiotic, a corticosteroid, a nitrosourea, an antimetabolite, a platinum based cytotoxic drug, a hormonal antagonist, an anti-androgen, an anti-estrogen, or a derivative, modification or combination of these agents, and all other anti-cancer agents disclosed in this application.

In another aspect, the invention provides a method of treating a patient suffering from a vascular proliferative disorder comprising the administration of a quinone, catechol, or Prodrug in order selectively reduce the flow of blood in the proliferating vasculature of the patient. As used herein "Vascular proliferative disorders" includes any mammalian disease state in which the pathology of the disease is characterized by the presence of endothiulium, arteries, blood vessels, or neovasculature formed by undesirable and pathological angiogenesis that is associated with disease states. These include disease neoplastic and malignant disease states such as solid tumor cancer, as well as non-malignant disease states, including without limitation ocular diseases such as wet or age-related macular degeneration, diabetic retinopathy, retinopathy of prematurity, diabetic molecular edema, uveitis, and corneal neovascularization, and other disease states including psoriasis, rheumatoid arthritis, atheroma, restenosis, Kaposi's sarcoma, haemangioma, and, in general, inflammatory diseases characterized by vascular proliferation.

The catechol, quinone compounds of the present invention and their Prodrugs may be used as dual activity agents in order to generate an enhanced response in vascular proliferative disorders.

Therapeautic Administration

Pharmaceutical compositions of the invention are formulated to be compatible with its intended route of administration. Pharmaceutical compositions may be prepared from the active ingredients or their salts in combination with pharmaceutically acceptable carriers.

As with the use of other chemotherapeutic drugs, the individual patient will be monitored in a manner deemed appropriate by the treating physician. Dosages can also be reduced if severe neutropenia or severe peripheral neuropathy occurs, or if a grade 2 or higher level of mucositis is observed, using the Common Toxicity Criteria of the National Cancer Institute.

The compositions of the present invention may also be formulated for systemic administration. Examples of systemic routes of administration include parenteral, e.g., intravenous, intradermal, subcutaneous, oral (e.g., inhalation), transmucosal, and rectal administration. Solutions or suspensions used for parenteral or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a vascular targeting agent) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In addition to the vascular targeting agents described above, the invention also includes the use of pharmaceutical compositions and formulations comprising a vascular targeting agent in association with a pharmaceutically acceptable carrier, diluent, or excipient, such as for example, but not limited to, water, glucose, lactose, hydroxypropyl methylcellulose, as well as other pharmaceutically acceptable carriers, diluents or excipients generally known in the art.

It is intended that the systemic and non-systemic administration of VTAs and tubulin binding agents in accordance with the present invention will be formulated for administration to mammals, particularly humans. However, the invention is not limited in this respect and formulations may be prepared according to veterinary guidelines for administration to animals as well.

In order to facilitate a further understanding of the invention, the following examples are presented primarily for the purpose of illustrating more specific details thereof. The scope of the invention should not be deemed limited by the examples, but encompass the entire subject matter defined in the claims. It will be apparent to those skilled in the art that many modifications, both to the materials and methods, may be practiced without departing from the purpose and interest of the invention.

EXAMPLES

Example 1

Synthesis of Novel Quinones a) Synthesis of CA-1 Ortho-Quinone, 4

The ortho-quinone of CA1 was synthesized from CA4 using the mild oxidant iodoxybenzoic acid.

To a solution of Combretastatin A-4 (0.032 g, 0.100 mmol; OXiGENE, Inc.) was added Iodoxybenzoic acid (0.028 g, 0.099 mmol) in $D_7$ DMF (4 ml) with stirring by vortex for ½ hr. Completion of the reaction was indicated by the disappearance of the initial yellowish slurry and the appearance of a clear solution of a deep red color. $^1$H-NMR was performed immediately as the quinone product was highly unstable and degraded within a ½ hr following the initiation of the reaction, as indicated by TLC and NMR.

4, $^1$H NMR: in $D_7$DMF δ (PPM) 7.27 (d, 1H, J=12.0 Hz, Ph-H), 7.01 (d, 1H, J=10.1 Hz, bridge-H), 6.93 (s, 2H, Ar—H), 6.80 (d, 1H, J=12.0 Hz, —H), 6.38 (dd, 1H, J=10.1 Hz, 1.6 Hz, bridge-H), 4.03 (s, 6H, —OCH$_3$), 3.96 (s, 3H, —OCH$_3$), 3.55 (s, 3H, —OCH$_3$).

b) Synthesis of CA-1 Para-Quinone, 5

The Para quinone of CA1 was synthesized using the mild oxidant Fremy's Salt.

To a mixture of Aliquot 336 (0.18 ml, 1.25 equiv) and NaH$_2$PO$_4$H$_2$O (0.323 g, 2.34 mmol) in water (100 ml) was added a solution of Combretastatin A4 (0.1 mg, 0.316 mmol, OXIGENE, Inc.) in dichloromethane (7 ml). Fremy's salt (potassium nitrosodisulfonate, 0.212 g, 0.8 mmol) was added and the mixture was stirred for 30 min. The solution turned deep red. The dichloromethane layer was seperated, collected and the aqueous phase was extracted with dichloromethane. The combined organic phases were washed with water and brine and dried over sodium sulfate. Solvent evaporation followed by purification by chromatography (60:40 hexanes: EtOAc) afforded the quinone as a red crystalline solid.

In an alternative synthetic route, CA1 p-quinone was synthesized using the oxidant Phenylseleninic Anhydride.

To a solution of phenylseleninic anhydride (0.227 g, 0.633 mmol) in freshly distilled THF (10 ml) was added Combretastatin A-4 (0.201 g, 0.633 mmol) dropwise in THF (5 ml), and heated to 50° C. The reaction was followed by TLC for disappearance of phenol. The reaction turned yellowish to red in color. In 2 hr the reaction was completed and was worked up by adding NaHCO$_3$, extraction with EtOAc. The organic layer was washed with water and dried over sodium sulfate. The reaction mixture was dried to purify using preparative TLC. One of the isolated spots afforded the para-quinone which showed similar $^1$H-NMR spectrum as the quinone obtained using Fremy's salt.

5, $^1$H NMR: in D$_6$Acetone δ (PPM) 6.94 (d, 1H, J=12.6 Hz, bridge-H), 6.72 (s, 2H, Ar—H), 6.66 (m, 1H, Ar—H), 6.42 (dd, 1H, J=12.5 Hz, 1.3 Hz, bridge-H), 6.07 (s, 1H, Ar—H), 3.85 (s, 3H, —OCH$_3$), 3.75 (s, 6H, —OCH$_3$), 3.73 (s, 3H, —OCH$_3$).

c) Phenanthraquinone Synthesis, 6

The phenanthraquinone analog of CA1 was synthesized using the oxidant O-chloranil.

To a solution of Combretastatin A-1 (0.050 g, 0.15 mmol) in Et$_2$O (1 ml) was added O-chloranil (tetrachloro-1,2-benzoquinone, 0.037 g, 0.15 mmol) with stirring for ½ hr. The reaction turned dark red in color. Reaction was followed by TLC until no starting material was left. The dark colored solid product obtained in quantitative yield was filtered and washed with hexanes and small amounts of ice cold ether.

6, $^1$H NMR: in CDCl$_3$ δ (PPM) 8.43 (s, 1H, Ar—H), 7.93 (d, 1H, J=8.6 Hz, Ar—H), 7.53 (d, 1H, J=8.1 Hz, Ar—H), 7.26 (s, 1H, Ar—H), 6.91 (s, 1H, Ar—H), 4.02 (s, 3H, —OCH$_3$), 4.01 (s, 3H, —OCH$_3$) 3.98 (s, 3H, —OCH$_3$), 3.92 (s, 3H, —OCH$_3$).

$^{13}$C NMR: in CDCl$_3$δ (PPM) 178.92, 176.27, 155.46, 151.69, 151.10, 144.26, 136.64, 133.39, 127.33, 125.61, 124.88, 120.03, 114.19, 104.43, 61.74, 61.43, 56.05, 55.54.

Example 2

Synthesis of Novel Catechols

The following catechol compounds were prepared synthetically by a Wittig reaction between an appropriately substituted aldehyde and an appropriately substituted phosphorous ylide. The aldehyde portion and ylide portion can be readily switched as well to allow for the judicious incorporation of the requisite functional groups within the target stilbenes (see Scheme 1 and 2 for general synthetic protocols).

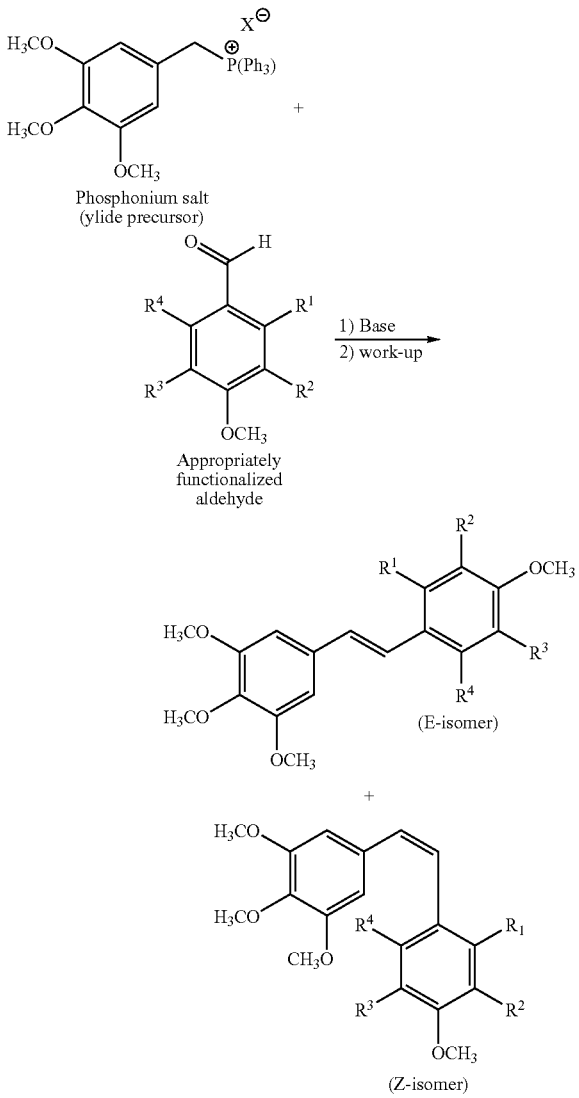

Scheme 1: General Synthetic Route to Stilbenoids - Part I

23

Scheme 2: General Synthetic Route to Stilbenoids - Part II

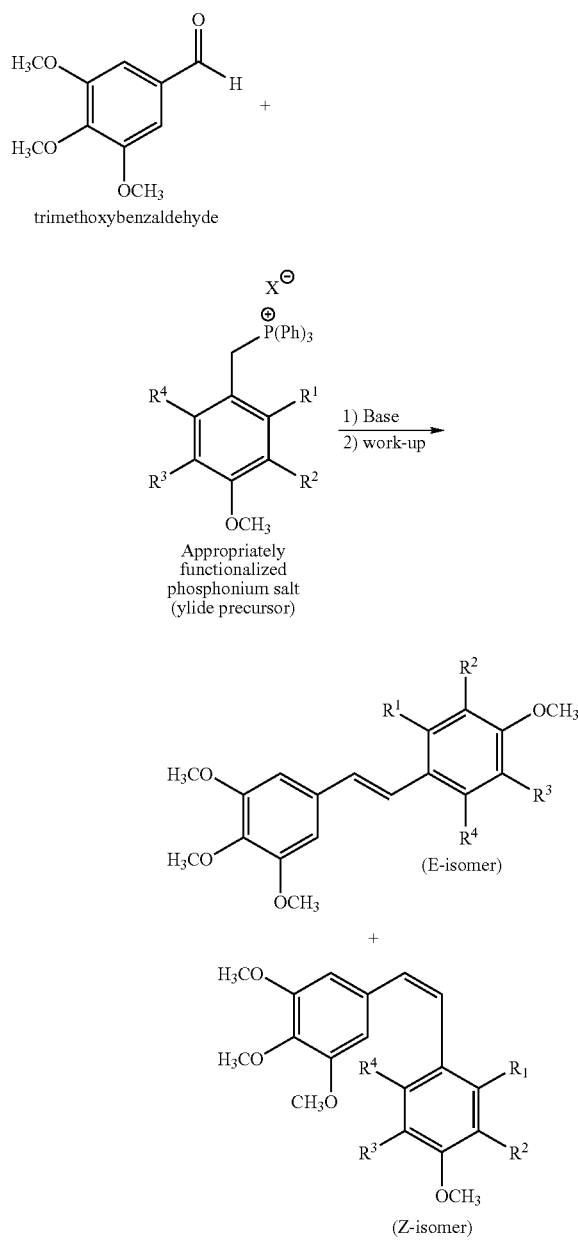

Appropriately
functionalized
phosphonium salt
(ylide precursor)

(E-isomer)

+

(Z-isomer)

General Methods:

LC/MS: LCMS analyses were run on an Micromass Single Quadrupole LCMS system comprising an Agilent HP-1100 LC with a Hypersil BDS $C_{18}$ (5μ) reverse phase column (2.1×50 mm) run with a flow rate of 1.00 mL/min. The mobile phase used solvent A ($H_2O$/0.1% TFA) and solvent B ($CH_3CN$/0.1% TFA) with a 2.1 min gradient from 0% to 95% $CH_3CN$. The gradient was followed by a 0.2 min return to 0% $CH_3CN$ and a 0.1 min flush. The peaks of interest eluted on the LC profiles at the times indicated.

Proton NMR: unless otherwise indicated all $^1H$ NMR spectra were run on an Bruker Avance 400 MHz instrument. All observed protons are reported as parts per million (ppm) downfield from tetramethylsilane (TMS) or other internal reference in the appropriate solvent indicated.

24 a) 6-[(Z)-2-(3,4,5-Trimethoxyphenyl)vinyl]-1,2-dihydroxybenzene (ZSB-82)

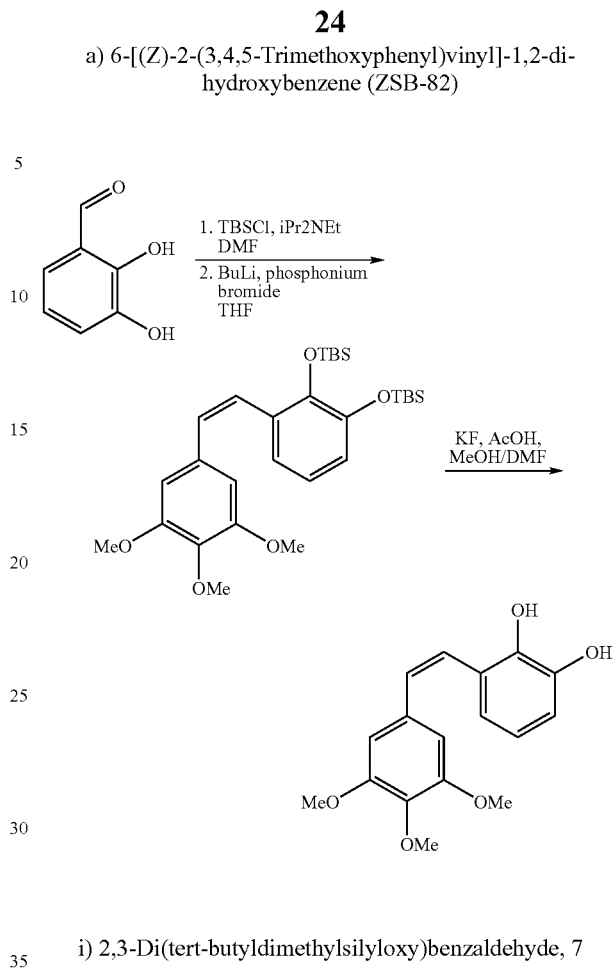

i) 2,3-Di(tert-butyldimethylsilyloxy)benzaldehyde, 7

2,3-Dihydroxybenzaldehyde (1.0 g; 7.24 mmol) was stirred in 5 mL of dimethylformamide and 3.79 mL diisopropylethylamine (2.81 g; 21.7 mmol) added under nitrogen. t-Butyldimethylsilyl chloride (2.44 g; 16.2 mmol) was then added and the mixture stirred overnight. The suspension was added to 25 mL 0.25M sodium hydrogen carbonate solution and extracted twice with 10 mL portions of t-butyl methyl ether. The organics were washed with brine, dried and evaporated affording 7 as a pale yellow oil (2.8 g).

$^1$H NMR ($CDCl_3$): 0.14 (s, 6H), 0.23 (s, 6H), 0.96 (s, 9H), 1.02 (s, 9H), 6.88-6.93 (m, 1H), 7.05-7.08 (m, 1H), 7.38-7.43 (m, 1H), 10.36 (s, 1H).

ii) 6-[(Z)-2-(3,4,5-Trimethoxyphenyl)vinyl]-1,2-di(tert-butyldimethylsilyloxy) benzene, 8

A suspension of 3,4,5-trimethoxybenzylphosphonium bromide (1.047 g, 2 mmol) in 12 mL dry tetrahydrofuran was stirred under nitrogen while cooling to −40° C. then adding 1.52 mL of 1.6M butyllithium in hexane (2.44 mmol) dropwise over six minutes below −25° C. The mixture was kept at −15° C. for ten minutes before cooling to −70°. 7 (0.748 g, 2.04 mmol) was added as a solution in 3 mL THF dropwise below −60° C. and the pale orange solution allowed to reach 20° C. over a period of one hour. After stirring for a further three hours the mixture was allowed to stand overnight. Water (8.5 mL) was added slowly and the mixture extracted three times with 8.5 mL t-butyl methyl ether. The organics were washed with brine, dried and evaporated at 30° C. The crude was purified by flash chromatography (cyclohexane:AcOEt 95:5) after removing triphenylphosphine oxide by filtration to give a colourless oil 8 which solidified on standing (0.70 g):

$^1$H NMR (CDCl$_3$): 6.88-6.92 (m, 1H), 6.71-6.75 (m, 1H), 6.61-6.68 (m, 1H), 6.57 (s, 2H), 6.42 (d, 1H, J 12.1), 6.45 (d, 1H, J 12.1), 3.83 (s, 3H), 3.66 (s, 6H), 1.02 (s, 9H), 0.97 (s, 9H), 0.21 (s, 6H), 0.19 (s, 6H).

iii) 6-[(Z)-2-(3,4,5-Trimethoxyphenyl)vinyl]-1,2-dihydroxybenzene (ZSB-82)

A solution of 8 (0.106 g, 0.2 mmol) in 2 mL THF was stirred at 0° while adding acetic acid (0.024 g, 0.4 mmol) and tetrabutylammonium fluoride (1M in THF, 0.4 ml, 0.4 mmol). The solution was stirred at 20° for one hour then cooled to 0° and 0.5 mL water added. The mixture was extracted with TBME three times, dried, evaporated and the residue partitioned between 10 mL heptane/10 mL acetonitrile. Evaporation of the acetonitrile layer gave 0.057 g pale yellow gum which was purified by silica chromatography with 7:3 heptane:ethyl acetate to give ZSB-82 as a colourless gum (0.032 g):

$^1$H NMR (CDCl$_3$): 6.75-6.87 (m, 3H); 6.63 (d, 1H, J 12.1), 6.66 (d; J 12.1, 1H); 6.47 (s, 2H); 5.52 (1H, s); 5.11 (1H, s); 3.82 (s, 3H); 3.62 (s, 6H).

b) 3-Ethyl-6-[(Z)-2-(3,4,5-trimethoxyphenyl)vinyl]-1,2-dihydroxybenzene (ZSB, 76)

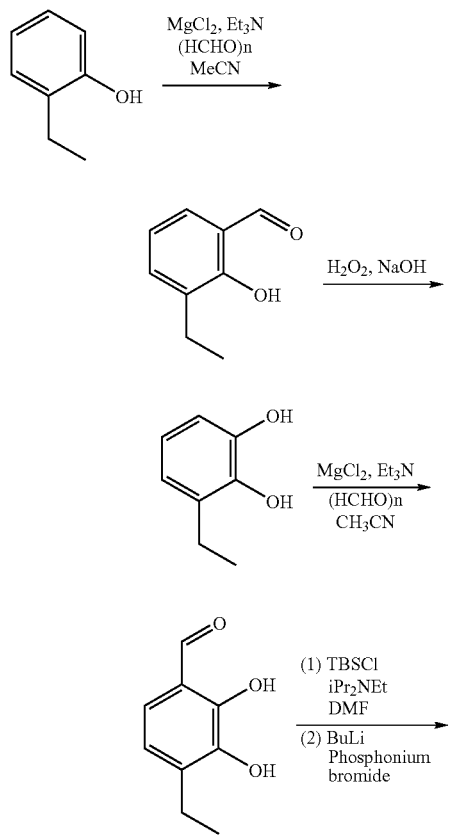

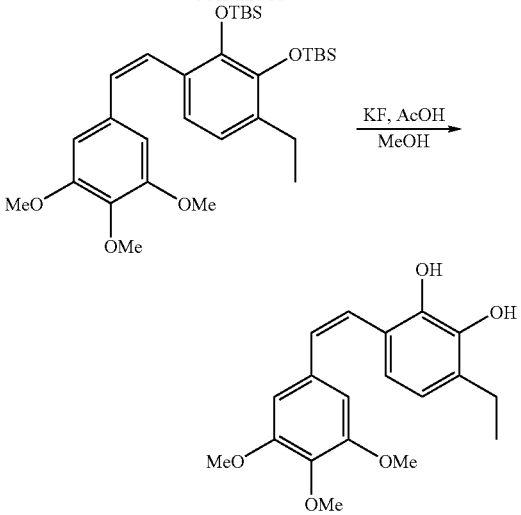

i) 2-Hydroxy-3-ethyl benzaldehyde, 9

Prepared according to Zaidlewicz, M.; et al; *Tetrahedron: Asymmetry*; 2003, 14, 1659-1664: Magnesium chloride (11.4 g, 120 mmol) was added at room temperature to a solution of 2-ethylphenol (9.77 g, 80 mmol) in acetonitrile (100 mL), followed by triethylamine (42 mL, 300 mmol). Paraformaldehyde (16.2 g, 540 mmol) was then added portionwise to the stirred suspension and the mixture was heated at reflux for 3 hours. The mixture was cooled to room temperature then poured into a vigorously stirred mixture of 250 mL of 5% HCl and 150 mL of diethyl ether. The organic phase was separated, and the aqueous layer re-extracted with 100 mL of ether. The combined organic extracts were washed with brine, dried over sodium sulphate and the solvent removed under reduced pressure to give 11.5 g of 9 as a yellow oil which was used without further purification:

$^1$H NMR (CDCl$_3$): 11.27 (1H, s); 9.88 (1H, s); 7.35-7.45 (2H, m); 6.96 (1H, t, J 7.5) 2.71 (2H, q, J 7.6); 1.23 (3H, t, J 7.5).

ii) 1,2-Dihydroxy-3-ethylbenzene, 10

To a solution of crude 9 (ca. 80 mmol) in 2N NaOH (40 mL) cooled to 0-5° C., a solution of ca. 7% hydrogen peroxide (49 mL) was added dropwise over 30 min while maintaining the temperature at 20° C. The reaction was stirred for further 45 min then diluted with AcOEt (ca 250 mL), washed with HCl 2N (ca 50 mL). The aqueous layer was e-extracted with AcOEt and the combined organic extracts were washed with brine, and dried over sodium sulphate. The solvent was removed under reduced pressure to give a crude which was columned (cyclohexane:AcOEt 4:1) to give 6.4 g of 10 as a brown oil:

$^1$H NMR (CDCl$_3$): 6.65-6.8) 3H, m); 5.16 (1H, bs); 5.09 (1H, bs); 2.64 (2H, q, J 7.5); 1.24 (3H, t, J 7.5).

iii) 2,3-Dihydroxy-4-ethyl benzaldehyde, 11

Magnesium chloride (1.71 g, 18 mmol) was added at room temperature to a solution of 10 (1 g, 7.2 mmol) in acetonitrile (10 mL), followed by triethylamine (6.3 mL, 45 mmol). Paraformaldehyde (1.47 g, 49 mmol) was then added portionwise to the stirred suspension and the mixture was heated at reflux for 2 hours. The mixture was cooled to room temperature then poured into a vigorously stirred mixture of 50 mL of 5% HCl and 50 mL of diethyl ether. The organic phase was separated, and the aqueous layer re-extracted with 50 mL of ether. The combined organic extracts were washed with brine, dried over sodium sulphate and the solvent removed under reduced pressure to give a crude which was purified by column (cyclohexane:AcOEt 6:1) to give 0.9 g of 11:

$^1$H NMR (CDCl$_3$): 11.1 (1H, s); 9.83 (1H, s); 7.08 (1H, d, J 8.3); 6.8 (1H, d, J 8.3); 5.65 (1H, s); 2.73 (2H, q, J 7.4); 1.24 (3H, t, J 7.4).

iv) 2,3-Di(tert-butyldimethylsilyloxy)-4-ethyl benzaldehyde, 12

To a solution of 11 (0.9 g, 5.4 mmol) in dimethylformamide (12 mL), tert-butyldimethylsilyl chloride (1.84 g, 12.2 mmol) was added in one portion followed by dropwise addition of diisopropylethylamine (2.3 mL, 13.5 mmol). The mixture was stirred for 6 hours, then diluted with tert-butylmethyl-ether/cyclohexane 4/1 (ca 150 mL) and washed with water (ca 50 mL). The aqueous layer re-extracted with 50 mL of ether, the combined organic extracts were washed with brine, dried over sodium sulphate and the solvent removed under reduced pressure to give 12 as a pale yellow oil (2 g) which was used without further purification:

$^1$H NMR (CDCl$_3$): 10.3 (1H, s); 7.4 (1H, d, J 8.6); 6.9 (1H, d, J 8.6); 2.64 (2H, t, J 7.4); 1.16 (3H, t, J 7.4); 1.04 (9H, s); 1.03 (9H, s); 0.12 (6H, s); 0.1 (6H, s).

v) 3-Ethyl-6-[(Z)-2-(3,4,5-trimethoxyphenyl)vinyl]-1,2-di(tert-butyldimethylsilyloxy)benzene, 13

A suspension of 3,4,5-trimethoxybenzyltriphenylphosphonium bromide (3.9 g, 7.5 mmol) in tetrahydrofuran (40 mL) was cooled to 0° C. and butyllithium (4.7 mL of a 1.6 N solution in hexane, 7.5 mmol) was added dropwise. The brick red solution was stirred at 0° C. for 20 min, then a solution of 12 (2 g, ca 5 mmol) in tetrahydrofuran (15 mL) was added dropwise. The temperature was allowed to rise to room temperature over 4 hours, than the reaction was poured into ethyl acetate (ca 150 mL) and NH$_4$Cl sat (ca 100 mL) the phases separated and the organic layer re-extracted with AcOEt. The combined organic extracts were washed with brine, dried over sodium sulphate and the solvent removed under reduced pressure to give a crude which was purified by column (cyclohexane:AcOEt 9:1) to give 0.6 g of 13:

$^1$H NMR (CDCl$_3$): 6.93 (1H, d, J 7.5); 6.56-6.66 (4H, m); 6.4 (1H, d, J 12.4); 3.83 (3H, s); 3.67 (6H, s); 2.56 (2H, q, J 7.6); 1.11 (3H, t, J 7.6); 1.03 and 1.01 (18H, 2 s); 0.16, 0.07 (12H, 2 s).

vi) 3-Ethyl-6-[(Z)-2-(3,4,5-trimethoxyphenyl)vinyl]-1,2-dihydroxybenzene, ZSB-76

To a solution of 13 (0.15 g, 0.268 mmol) in methanol (2 mL), acetic acid was added acetic acid (0.032 mL, 0.563 mmol) followed by potassium fluoride (0.033 mg, 0.563 mmol). Dimethylformamide was then added (0.5 mL) and the mixture was stirred for 16 hours then more acetic acid (0.04 mL) and KF (0.033 mg) were added and the mixture stirred for 48 hours. The mixture was then diluted with tertbutylmethyl ether (50 mL) and washed with water (10 mL). The aqueous layer was re-extracted, the combined organic layers were washed with brine, dried over sodium sulphate and the solvent removed under reduced pressure to give a crude which was purified by column (cyclohexane:AcOEt 8:2+1% AcOH) to give 0.05 g of ZSB-76:

LCMS: Rt 1.95; Mass found: 683 (2M+Na$^+$), 331 (MH$^+$).
$^1$H NMR (CDCl$_3$): 6.74 (1H, d, J 7.9); 6.7 (1H, d, J 7.9); 6.4 (1H, d, J 12.1); 6.5 (1H, d, J 12.1); 6.45 (2H, s); 5.4 (1H, s); 4.9 (1H, s); 3.83 (3H, s); 3.61 (6H, s); 2.65 (2H, q, J 7.6); 1.19 (3H, t, J 7.6)

c) 3-Methyl-6-[(Z)-2-(3,4,5-trimethoxyphenyl)vinyl]-1,2-dihydroxybenzene, ZSB-75

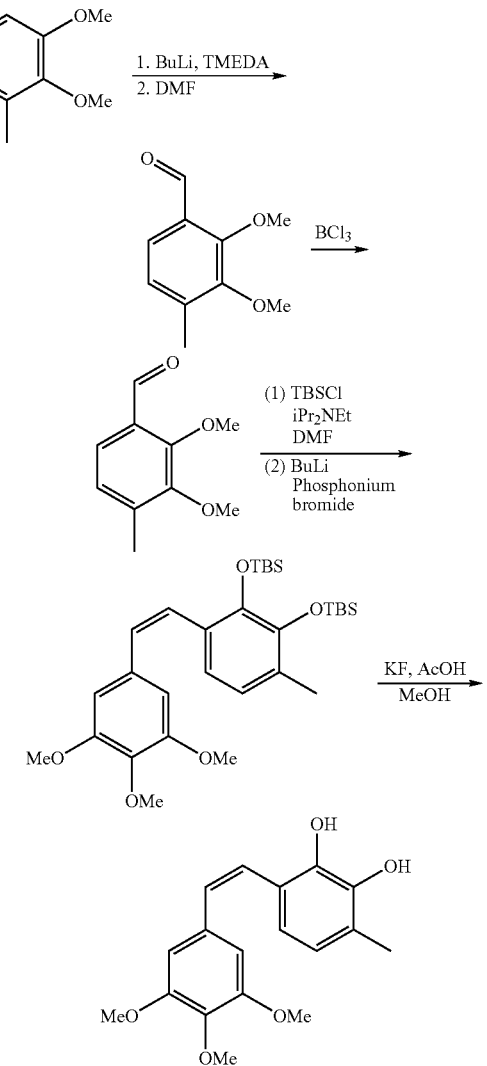

i) 2,3-Dimethoxy-4-methylbenzaldehyde, 14

2,3-Dimethoxytoluene (2 g, 13.1 mmol) was weighed in a flask and ether was added to the flask. N,N,N',N'-tetramethylethylenediamine (422 mg, 3.6 mmol) was added to the solution. While stirring, the mixture was cooled down to 0° C. and n-Butyl lithium 1.6M in hexane (2.25 mL, 3.6 mmol) was added slowly over 20 minutes. The solution was stirred at 0° C. for 30 minutes after which the ice bath was removed. The solution became yellow during addition and after removal of the ice bath, a precipitate started forming. The reaction mixture was left stirring overnight at room temperature under nitrogen then cooled down again to 0° C. and DMF (1.23 mL, 15.9 mmol) was added. The homogeneous reaction mixture was stirred at this temperature for 1 hour. The solution was poured onto crushed ice and 15 mL ammonium chloride 1N. The phases were separated and the organic phase was washed with 4 portions of 1N ammonium chloride. The organics were dried over sodium sulphate, filtered and the filtrate was evaporated under vacuum. The crude product was purified on normal silica with DCM to yield 1.27 g (58%) of 14 which was used in the next stage.

$^1$H NMR (CDCl$_3$): 10.33 (1H, s); 7.38 (1H, d); 6.96 (1H, d); 3.97 (3H, s); 3.85 (3H, s); 2.32 (3H, s).

ii) 2,3-Dihydroxy-4-methylbenzaldehyde, 15

14 (770 mg, 4.6 mmol) was placed in solution in DCM (8 mL) under nitrogen and the solution was cooled down at −20° C. while stirring. Boron trichloride 1M in DCM (10 mL, 9.2 mmol) was added slowly over 15 minutes keeping the temperature below −20° C. The reaction mixture turned from yellow to dark red and was left stirring and warming up overnight. More boron trichloride (5 mL) was added in the morning at T<−20° C. and the reaction was left stirring overnight after which the reaction appeared complete by LC-MS. The mixture was poured into water and extracted with ethyl acetate. The organic phase was dried over sodium sulphate, filtered and evaporated. The crude product was columned on silica with neat DCM to yield 306 mg of 15:

$^1$H NMR (CDCl$_3$): 11.11 (1H, s); 9.82 (1H, s); 7.05 (1H, d); 6.84 (1H, s); 5.76 (1H, s); 2.29 (3H, s).

iii) 2,3-Bis-tert-butyldimethylsilyloxy-4-methylbenzaldehyde, 16

15 (440 mg, 2.9 mmol) was placed in solution in DMF (4.4 mL) under nitrogen and N,N-diisopropylethylamine (1.52 mL, 8.7 mmol) was added. Tert-butyldimethylchlorosilane was added portionwise to the reaction mixture while stirring and the reaction was left stirring over 48 hours at room temperature. The solution was then quenched with 10 mL of a saturated solution of sodium hydrogen carbonate and 10 mL of TBME was added. The organic phase was separated and the aqueous phase re-extracted with twice 10 mL of TBME. The organics were washed with brine, dried over sodium sulphate, filtered and evaporated to yield 859 mg of 16 which was used without further purification:

$^1$H NMR (CDCl$_3$): 10.19 (1H, s); 7.26 (1H, m); 6.75 (1H, m); 2.15 (3H, s); 0.92 (18H, s); 0.75 (6H, s); 0.05 (6H, s).

iv) 3-Methyl-6-[(Z)-2-(3,4,5-trimethoxyphenyl)vinyl]-1,2-di(tert-butyldimethylsilyloxy)benzene, 17

A suspension of 3,4,5-trimethoxybenzyltriphenylphosphonium bromide (1.77 g, 3.4 mmol) in tetrahydrofuran (40 mL) was cooled to 0° C. and butyllithium (2.1 mL of a 1.6 N solution in hexane, 3.39 mmol) was added dropwise. The brick red solution was stirred at 0° C. for 20 min, then cooled to −78° C. and a solution of 16 (0.86 g, 2.26 mmol) in tetrahydrofuran (15 mL) was added dropwise. The temperature was allowed to rise to room temperature overnight, than the reaction was poured into brine (100 mL, containing 5 mL of 1 n HCl) and extracted twice with tert-butylmethyl ether (ca 100+50 mL). The combined organic extracts were washed with brine, dried over sodium sulphate and the solvent removed under reduced pressure to give a crude which was purified by column (cyclohexane:AcOEt 9:1) to give 0.6 g of 17:

$^1$H NMR (CDCl$_3$): 6.91 (1H, d, J 7.7); 6.56-6.66 (4H, m); 6.4 (1H, d, J 12.3); 3.83 (3H, s); 3.67 (6H, s); 2.18 (3H, s); 1.03 (18H, s); 0.16, 0.09 (12H, 2 s).

v) 3-Methyl-6-[(Z)-2-(3,4,5-trimethoxyphenyl)vinyl]-1,2-dihydroxybenzene, ZSB-75

To a solution of 17 (0.42 g, 0.77 mmol) in tetrahydrofuran (2 mL), acetic acid was added (0.097 mL, 1.7 mmol) followed by tetrabutylammonium fluoride (1.62 mL of 1N solution in THF, 1.62 mmol). The mixture was stirred for 16 hours then diluted with tertbutylmethyl ether (100 mL) and washed with water (30 mL) then brine (30 mL). The organic layer was dried over sodium sulphate and the solvent removed under reduced pressure to give a crude which was purified by column (cyclohexane:AcOEt 7:3+1% AcOH) to give 0.138 g of ZSB-75:

LCMS: Rt 1.87; Mass found: 655 (2M+Na$^+$), 317 (MH$^+$).

$^1$H NMR (CDCl$_3$): 6.74 (1H, d, J 7.9); 6.7 (1H, d, J 7.9); 6.4 (1H, d, J 12.1); 6.5 (1H, d, J 12.1); 6.45 (2H, s); 5.4 (1H, s); 4.9 (1H, s); 3.83 (3H, s); 3.61 (6H, s); 2.24 (3H, s).

d) 4-Bromo-6-[(Z)-2-(3,4,5-trimethoxyphenyl)vinyl]-1,2-dihydroxybenzene, ZSB-74

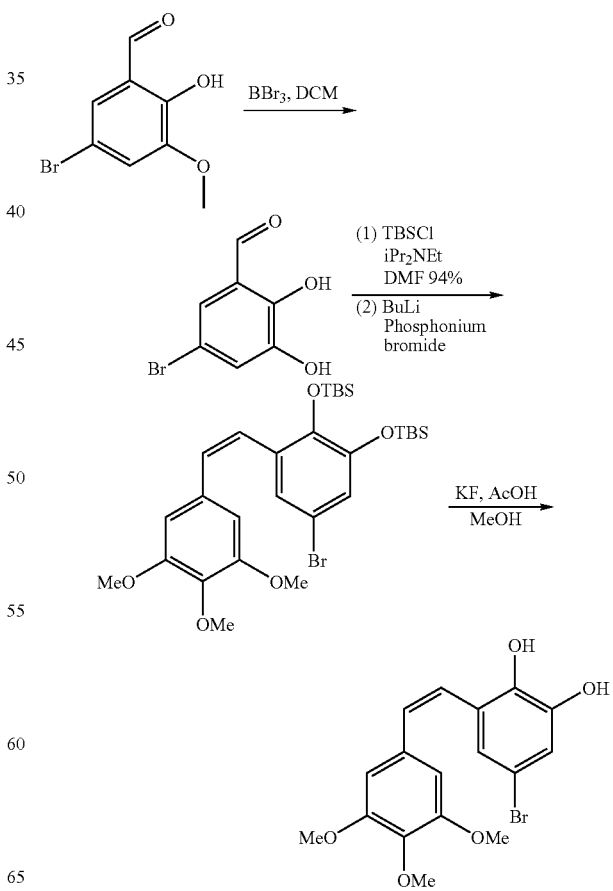

i) 5-Bromo-2,3-dihydroxybenzaldehyde, 18

5-Bromo-3-methoxy-2-hydroxybenzaldehyde (0.92 g; 4 mmol) was stirred under nitrogen below 0° while adding boron tribromide (1M in dichloromethane –12.0 mL; 12 mmol) then allowed to stand at 20° overnight. The mixture was cooled to 0° while adding carefully a total of 30 mL water then saturated sodium hydrogen carbonate (30 mL). Extraction with dichloromethane, drying and evaporating gave very little material which was discarded. Acidification of the aqueous layer to pH 1 with hydrochloric acid gave a precipitate which was extracted with dichloromethane (80 mL three times), dried and evaporated giving 18 as a pale yellow solid (0.78 g):
$^1$H NMR (CDCl$_3$): 10.41, 10.29 (br singlets, 2H), 10.19 (s, 1H), 7.20-7.22 (m, 1H), 7.13-7.16 (m, 1H).

ii) 2,3-Di(tert-butyldimethylsilyloxy)-5-bromo benzaldehyde, 19

To a solution of 18 (0.5 g, 2.3 mmol) in dimethylformamide (6 mL), tert-butyldimethylsilyl chloride (0.784 g, 5.2 mmol) was added in one portion followed by dropwise addition of diisopropylethylamine (0.99 mL, 5.75 mmol). The mixture was stirred for 6 hours, then diluted with tert-butylmethyl ether (ca 150 mL) and washed with water twice (ca 50+30 mL) then brine (30 mL). The organic layer was dried over sodium sulphate and the solvent removed under reduced pressure to give 19 as a pale yellow oil (0.96 g) which was used without further purification:
$^1$H NMR (CDCl$_3$): 10.3 (1H, s); 7.5 (1H, d, J 2.5); 7.17 (1H, d, J 2.5); 1.03 (9H, s); 0.98 (9H, s); 0.25 (6H, s); 0.14 (6H, s).

iii) 4-Bromo-6-[(Z)-2-(3,4,5-trimethoxyphenyl)vinyl]-1,2-di(tert-butyldimethylsilyloxy)benzene, 20

A suspension of 3,4,5-trimethoxybenzyltriphenylphosphonium bromide (1.69 g, 3.23 mmol) in tetrahydrofuran (30 mL) was cooled to 0° C. and butyllithium (2 mL of a 1.6 N solution in hexane, 3.23 mmol) was added dropwise. The brick red solution was stirred at 0° C. for 20 min, then a solution of 19 (0.96 g, ca 2.2 mmol) in tetrahydrofuran (12 mL) was added dropwise. The temperature was allowed to rise to room temperature overnight, than the reaction was diluted with tert-butylmethyl ether (ca 100 mL) and washed with water (ca 50 mL, containing 1 mL 2N HCl) then brine (30 mL). The organic layer was dried over sodium sulphate and the solvent removed under reduced pressure to give a crude which was purified by column (elution with cyclohexane:AcOEt 10:1) to give 0.75 g of 20 still impure with 20% of the E isomer.
$^1$H NMR (CDCl$_3$): 7.08 (1H, d, J 2.4); 6.84 (1H, d, J 2.4); 6.58 (2H, s); 6.53 (1H, d, J 12.1); 6.44 (1H, d, H 12.1); 3.84 (3H, s); 3.71 (6H, s); 1.00 (9H, s) and 0.96 (9H, s); 0.2 (6H, s); 0.16 (6H, s).

iv) 4-Bromo-6-[(Z)-2-(3,4,5-trimethoxyphenyl)vinyl]-1,2-dihydroxybenzene, ZSB-74

To a solution of 20 (0.19 g, 0.32 mmol) in methanol: dimethylformamide 1:1 (4 mL), acetic acid was added (0.114 mL, 1.9 mmol) followed by potassium fluoride (0.110 mg, 1.9 mmol). The mixture was stirred for 30 hours then diluted with tertbutylmethyl ether (50 mL) and washed with water (20 mL) then brine (20 mL), then dried over sodium sulphate. The solvent was removed under reduced pressure to give a crude which was purified by column (cyclohexane:AcOEt 7:3+1% AcOH) to give 0.097 g of ZSB-74:
LCMS: Rt 1.89; Mass found: 785 (2M+Na$^+$), 381 (MH$^+$).
$^1$H NMR (CDCl$_3$): 6.99 (1H, d, J 2.1); 6.96 (1H, d, J 2.1); 6.7 (1H, d, J 12.1); 6.4-6.5 (3H, m); 5.46 (1H, s); 4.97 (1H, s); 3.84 (3H, s); 3.66 (6H, s).

e) 4-Phenyl-6-[(Z)-2-(3,4,5-trimethoxyphenyl)vinyl]-1,2-dihydroxybenzene, ZSB-80

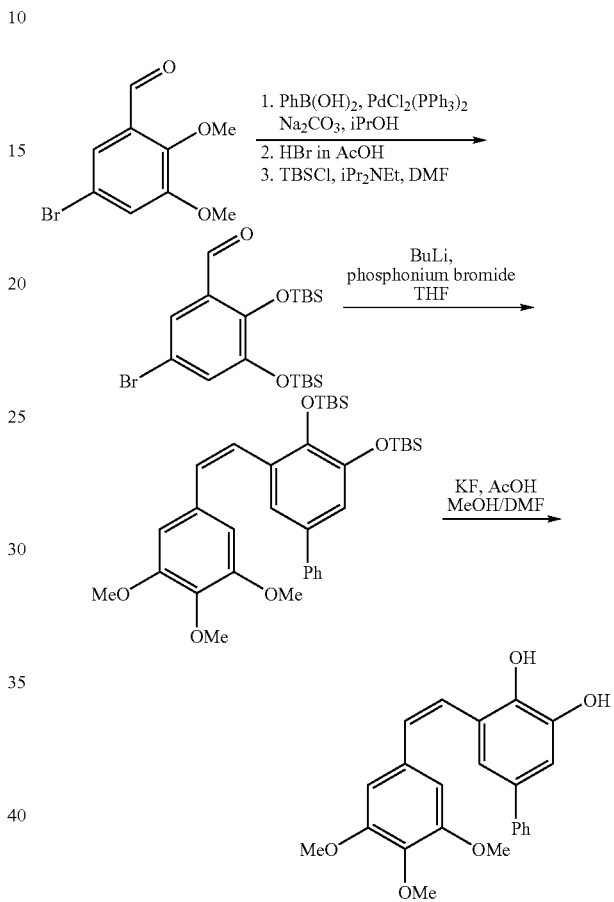

i) 2,3-Dimethoxy-5-phenylbenzaldehyde, 21

A stirred mixture of benzeneboronic acid (0.610 g; 5 mmol), 5-bromo-2,3-dimethoxybenzaldehyde (1.00 g; 4.1 mmol), bis(triphenylphosphine)palladium (II) chloride (0.050 g; 0.071 mmol), sodium carbonate (0.848 g; 8 mmol), isopropanol (40 mL) and water (4.0 mL) was bubbled with nitrogen for fifteen minutes then heated under reflux overnight. The mixture was evaporated, the residue stirred with water and dichloromethane and the organic layer dried and evaporated. The residue was taken up in boiling cyclohexane (40 mL twice) and filtered hot. The solution was chromatographed on silica using cyclohexane to elute triphenylphosphine and 10% ethyl acetate—90% cyclohexane to elute product 21 (0.87 g) as a white crystalline solid:
$^1$H NMR (CDCl$_3$): 10.5 (s, 1H), 7.63-7.69 (m, 1H), 7.53-7.60 (m, 2H), 7.42-7.49 (m, 2H), 7.33-7.41 (m, 2H), 4.02 (s, 3H), 3.98 (s, 3H).

ii) 2,3-Dihydroxy-5-phenylbenzaldehyde, 22

A mixture of 21 (0.63 g; 2.6 mmol), 48% aqueous hydrobromic acid (15 mL) and acetic acid (12 mL) was stirred under nitrogen at reflux overnight. The suspension was decanted from dark solid and evaporated. The residue was taken up in boiling dichloromethane (three lots of 50 mL), filtered hot and evaporated giving 22 as pale brown solid (0.290 g):

$^1$H NMR (DMSO-d6): 10.2 (s, 1H), 10.2 (br s, 1H), 10.0 (br s, 1H), 7.55-7.63 (m, 2H), 7.42-7.50 (m, 3H), 7.31-7.38 (m, 2H).

iii) 2,3-Di(tert-butyldimethylsilyloxy)-5-phenylbenzaldehyde, 23

Standard conditions gave 0.481 g crude 23 which was purified by silica chromatography eluting with 2% ethyl acetate 98% cyclohexane.

$^1$H NMR (CDCl$_3$): 10.42 (s, 1H), 7.67-7.69 (m, 1H), 7.52-7.57 (m, 3H), 7.40-7.47 (m, 2H), 7.34-7.37 (m, 1H), 1.05 and 1.01 (2 s, 18H), 0.1957 and 0.29 (2 s, 12H).

iv) 4-Phenyl-6-[(Z)-2-(3,4,5-trimethoxyphenyl)vinyl]-1,2-di(tert-butyldimethylsilyloxy)benzene, 24

A suspension of 3,4,5-trimethoxybenzyltriphenylphosphonium bromide (0.24 g, 0.46 mmol) in tetrahydrofuran (4 mL) was cooled to 0° C. and butyllithium (0.28 mL of a 1.6 N solution in hexane, 0.46 mmol) was added dropwise. The brick red solution was stirred at 0° C. for 20 min, then a solution of 23 (0.13 g, 0.3 mmol) in tetrahydrofuran (2 mL) was added dropwise. The temperature was allowed to rise to room temperature overnight, than the reaction was diluted with tert-butylmethyl ether (ca 100 mL) and washed with water (ca 50 mL, containing 1 mL 2N HCl) then brine (30 mL). The organic layer was dried over sodium sulphate and the solvent removed under reduced pressure to give a crude which was purified by column (elution with cyclohexane:AcOEt 10:1) to give 0.05 g of 24 still impure with 20% of the E isomer.

$^1$H NMR (CDCl$_3$): 7.2-7.35 (5H, m); 7.14 (1H, d, J 2.4); 6.97 (1H, d, J 2.4); 6.68 (1H, d, J 12.1); 6.62 (2H, s); 6.49 (1H, d, J 12.1); 6.44 (1H, d, J 12.1); 3.83 (3H, s); 3.64 (6H, s); 1.04 (9H, s) and 0.99 (9H, s); 0.26 (6H, s); 0.22 (6H, s).

v) 4-Phenyl-6-[(Z)-2-(3,4,5-trimethoxyphenyl)vinyl]-1,2-dihydroxybenzene, ZSB-80

To a solution of 24 (0.05 g, 0.082 mmol) in methanol:dimethylformamide 1:1 (2 mL), acetic acid was added (0.025 mL, 0.41 mmol) followed by potassium fluoride (0.024 mg, 0.41 mmol). The mixture was stirred for 6 hours then diluted with tertbutylmethyl ether (50 mL) and washed with water (10 mL) then brine (50 mL), then dried over sodium sulphate. The solvent was removed under reduced pressure to give a crude which was purified by column (cyclohexane:AcOEt 6:4+1% AcOH) to give 0.097 g of ZSB-80:

LCMS: Rt 1.95; Mass found: 379 (MH$^+$), 757 (2M+H$^+$).

$^1$H NMR (CDCl$_3$): 7.45-7.5 (2H, m); 7.35-7.4 (2H, m); 7.25-7.35 (1H, m); 7.1 (1H, d, J 2.4); 7.05 (1H, d, J 2.4); 6.7 (1H, d, J 11.9); 6.6 (1H, d, J 11.9); 6.5 (2H, s); 5.4 (1H, s); 5.1 (1H, s); 3.84 (3H, s); 3.63 (6H, s).

f) 3-Allyl-6-[(Z)-2-(3,4,5-trimethoxyphenyl)vinyl]-1,2-dihydroxybenzene, ZSB-77

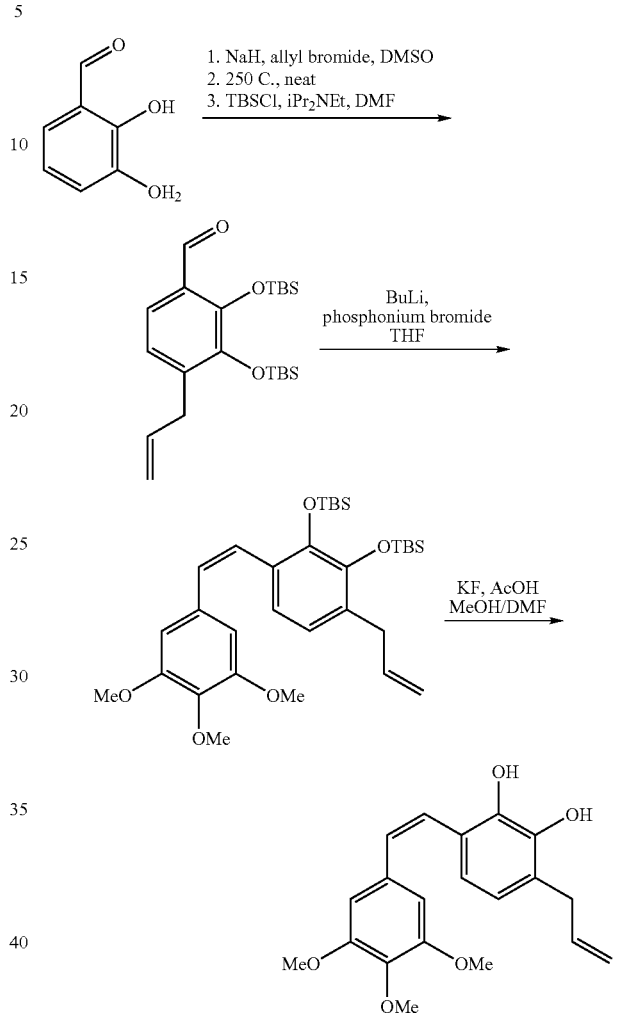

i) 3-Allyloxy-2-hydroxybenzaldehyde, 25

A solution of 2,3-dihydroxybenzaldehyde (5.51 g-0.040 mol) in 30 mL dry DMSO was added with stirring below 20° C. under nitrogen to a suspension of sodium hydride (3.80 g-0.081 mol) in 60 mL DMSO. After one hour solids adhering to the sides of the flask were carefully dislodged with a spatula and stirring continued for 20 minutes. A solution of allyl bromide (3.46 mL-4.84 g-0.040 mol) in 10 mL DMSO was added dropwise below 27° and stirring continued overnight. 1M hydrochloric acid (50 mL) was added slowly and the mixture extracted three times with ethyl acetate. The extracts were washed three times with brine, dried and evaporated giving 10.0 g pale brown oil. Chromatography on 800 mL silica eluting with 80:20:1 heptane:ethyl acetate:acetic acid gave 2.85 g of 25 as a pale yellow oil:

$^1$H NMR (CDCl$_3$): 11.08 (s, 1H), 9.91 (s, 1H), 7.17-7.22 (m, 1H), 7.11-7.15 (m, 1H), 6.92-6.97 (m, 1H), 6.01-6.15 (m, 1H), 5.38-5.47 (m, 1H), 5.28-5.31 (m, 1H); 4.63-4.68 (m, 2H).

ii) 4-Allyl-2,3-dihydroxybenzaldehyde, 26

25 (2.82 g) was heated and stirred under nitrogen in a 25 mL flask/condenser heated on a metal block to 247° for twelve minutes. The resulting pale brown oil was chromatographed on 200 mL silica eluting with 80:20:1 heptane:ethyl acetate:acetic acid giving 26 as a pale green semi-solid (1.25 g):

$^1$H NMR (CDCl$_3$): 11.12 (s, 1H), 9.83 (s, 1H), 7.07-7.11 (m, 1H), 6.81-6.85 (m, 1H), 5.96-6.07 (m, 1H), 5.69 (s, 1H), 5.07-5.17 (m, 2H), 3.46-3.48 (m, 2H).

iii) 2,3-Di(tert-butyldimethylsilyloxy)-4-allylbenzaldehyde, 27

26 (1.25 g-7.0 mmol) was dissolved in 5 mL DMF and stirred under nitrogen. t-Butyldimethylsilyl chloride (2.35 g-15.6 mmol) was added followed by diisopropylethylamine (3.66 mL-2.72 g-21.0 mmol) and stirring continued overnight.

TBME (10 mL) was added and the solution decanted from amine hydrochloride. This process was repeated twice and the resulting solution was washed with 1M sodium hydrogen carbonate twice, brine twice, dried and evaporated giving 27 as a pale purple oil:

$^1$H NMR (CDCl$_3$): 10.29 (s, 1H), 7.40-7.42 (m, 1H), 6.86-6.88 (m, 1H), 5.82-5.94 (m, 1H), 5.02-5.11 (m, 2H), 3.37-3.41 (m, 2H), 1.02 and 1.03 (two s, 18H), 0.08 and 0.12 (two s, 12H).

iv) 3-Allyl-6-[(Z)-2-(3,4,5-trimethoxyphenyl)vinyl]-1,2-di(tert-butyldimethylsilyloxy)benzene, 28

A suspension of 3,4,5-trimethoxybenzylphosphonium bromide (1.047 g-2 mmol) in 12 mL dry tetrahydrofuran was stirred under nitrogen while cooling to −40° C. then adding 1.52 mL of 1.6M butyllithium in hexane (2.44 mmol) dropwise over six minutes below −25° C. The mixture was kept at −15° for ten minutes before cooling to −70°. 27 (0.814 g-2.0 mmol) was added as a solution in 3 mL THF dropwise below −60° and allowed to reach 20° over a period one hour. After stirring for a further three hours the mixture was allowed to stand overnight giving a pale brown solution. Water (8.5 mL) was added slowly and the mixture extracted three times with 8.5 mL t-butyl methyl ether. The organics were washed with brine, dried and evaporated at 30° C. giving a pale red semi-solid which was purified by flash chromatography on 150 mL silica eluting with 95% cyclohexane: 5% ethyl acetate giving 27 as a colourless oil (0.84 g):

$^1$H NMR (CDCl$_3$): 6.92-6.96 (m, 1H), 6.58-6.67 (m, 4H), 6.38 (d, 1H, J 12.6), 6.42 (d, 1H, J 12.6), 5.82-5.96 (m, 1H), 4.94-5.09 (m, 2H), 3.83 (s, 3H), 3.66 (s, 6H), 3.31-3.35 (m, 2H), 1.03 (s, 18H), 0.16 (s, 6H), 0.08 (s, 6H).

v) 3-Allyl-6-[(Z)-2-(3,4,5-trimethoxyphenyl)vinyl]-2,3-dihydroxybenzene, ZSB-77

A solution of 27 (0.456 g-0.8 mmol) in 10 mL DMF and 10 mL methanol was stirred under nitrogen while adding 0.114 mL-0.120 g-2.0 mmol) of acetic acid then potassium fluoride (dried-0.232 g-4.0 mmol) and stirring was continued overnight. TBME (total 150 mL) was added and the mixture washed with water (25 mL), brine twice, dried and evaporated at 30°. Chromatography of the product on 40 mL silica eluting with 80:20:1 cyclohexane:ethyl acetate:acetic acid gave ZSB-77 as an off-white solid (0.150 g):

$^1$H NMR (CDCl$_3$): 6.67-6.76 (m, 2H); 6.61 (d, J 12.1, 1H); 6.64 (d, J 12.1, 1H); 6.52 (d, J 12.1, 1H); 6.47 (s, 2H); 5.93-6.05 (m, 1H); 5.05-5.13 (m, 3H); 3.82 (s, 3H); 3.62 (s, 6H) 3.40 (d, 2H, J 6.5).

g) 4-Fluoro-6-[(Z)-2-(3,4,5-trimethoxyphenyl)vinyl]-1,2-dihydroxybenzene, ZSB-78

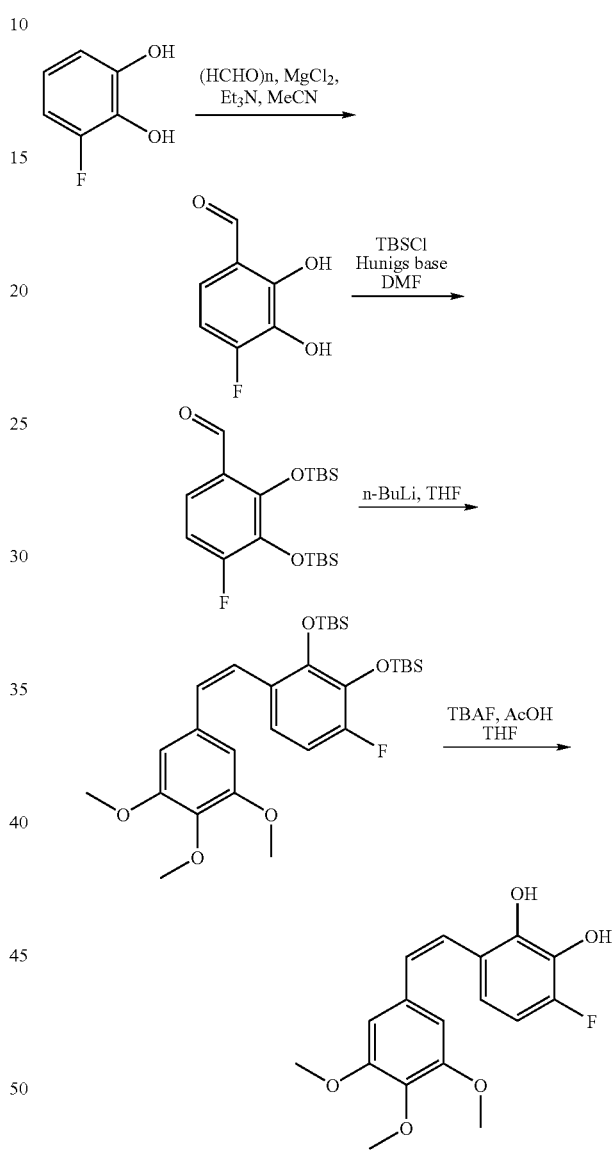

i) 4-Fluoro-2,3-dihydroxybenzaldehyde, 28

Magnesium chloride (3.71 g, 33 mmol) was added portionwise at room temperature to a solution of 3-fluorocatechol (2 g, 15.6 mmol) in acetonitrile (20 mL), followed by triethylamine (13.4 mL, 97.5 mmol). Paraformaldehyde (3.16 g, 105.3 mmol) was then added to the stirred suspension and the mixture was heated at reflux for 5 hours. The mixture was cooled to room temperature then poured into a mixture of 5% HCl and TBME. The organic phase was separated, and the aqueous layer re-extracted with TBME. The combined organic extracts were washed with brine, dried over sodium sulphate and the solvent removed under reduced pressure. The crude mixture (~1:1 starting material:product) was purified on normal silica in neat DCM followed by DCM/MeOH 96:4 and 90:10 to yield 478 mg of 28 still contaminated with 11.4% w/w of 3-fluorocatechol.

$^1$H NMR (CDCl$_3$): 11.37 (1H, s); 9.83 (1H, s); 7.16 (1H, m); 6.80 (1H, m); 5.43 (1H, s).

ii) 2,3-Di t-butyldimethylsilyloxy-4-fluorobenzaldehyde, 29

As for 2,3-Di-tert-butyldimethylsilyloxy-4-methylbenzaldehyde.

Obtained 945 mg of 29, yield =82%:

$^1$H NMR (CDCl$_3$): 10.11 (1H, s); 7.27 (1H, m); 6.66 (1H, m); 0.89 (9H, s); 0.85 (9H, s); 0.04 (6H, d); 0.0 (6H, s).

iii) 4-Fluoro-6-[(Z)-2-(3,4,5-trimethoxyphenyl)vinyl]-1,2-di(t-butyldimethylsilyloxy)-benzene, 30

A suspension of 3,4,5-trimethoxybenzyltriphenylphosphonium bromide (1.25 g, 2.4 mmol) in tetrahydrofuran (14 mL) was cooled to −20° C. and n-butyllithium 1.6M in hexane (1.83 mL, 2.9 mmol) was added dropwise. The red solution was stirred at −20° C. for 20 min, then cooled down to −78° C. A solution of 29 (940 mg, 2.4 mmol) in tetrahydrofuran (4 mL) was added dropwise. The temperature was allowed to rise to room temperature overnight. The reaction mixture was poured into ethyl acetate (ca 15 mL) and NH$_4$Cl sat (ca 15 mL), the phases were separated and the organic layer re-extracted with ethyl acetate. The combined organic extracts were washed with brine, dried over sodium sulphate and the solvent removed under reduced pressure to give a crude which was purified by column (neat DCM) to give 869 mg of 30 compound:

$^1$H NMR (CDCl$_3$): 6.68 (1H, m); 6.52 (1H, m); 6.37 (1H, m); 6.34 (1H, m); 6.22 (1H, m); 3.64 (3H, s); 3.48 (6H, s); 0.80 (9H, s); 0.80 (9H, s).

iv) 4-Fluoro-6-[(Z)-2-(3,4,5-trimethoxyphenyl)vinyl]-1,2-dihydroxybenzene, ZSB-78

To a solution of 30 (860 mg, 1.57 mmol) in tetrahydrofuran (8.6 mL), acetic acid was added (0.20 mL, 3.13 mmol) followed by tetrabutylammonium fluoride 1N solution in THF (3.13 mL, 3.13 mmol). The mixture was stirred for 3 hours then diluted with tertbutylmethyl ether and washed with water then brine. The organic layer was dried over sodium sulphate and the solvent removed under reduced pressure to give a crude which was purified by columns (three times— first with cyclohexane:AcOEt 1:1, then with cyclohexane:AcOEt 7:3+1% acetic acid and finally cyclohexane:AcOEt 8:2+1% acetic acid) to yield 70 mg (14% yield) of ZSB-78:

LCMS: Rt 1.79; Mass found: 663 (2M+Na$^+$), 321 (MH$^+$).

$^1$H NMR (acetone-d6): 8.45 (1H, s); 7.95 (1H, s); 6.71 (1H, m); 6.45-6.65 (5H, m); 3.70 (3H, s); 3.64 (6H, s).

h) 2,3,4-Trihydroxy-6-[(Z)-2-(3,4,5-trimethoxyphenyl)vinyl]-benzene, ZSB-79

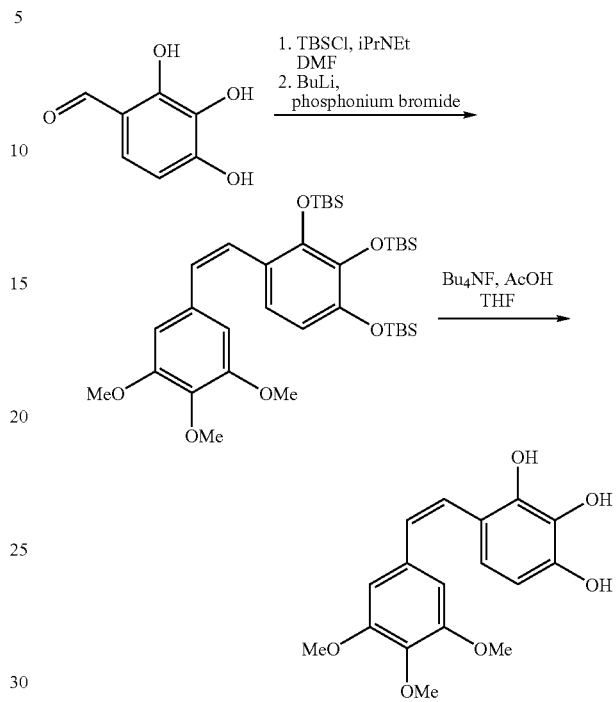

i) 2,3,4-Tri(t-butyldimethylsilyloxy)benzaldehyde, 31 t-Butyldimethylsilylchloride (1.64 g, 10.9 mmol) was added dropwise over 5 min to a solution of 2,3,4-trihydroxybenzaldehyde (0.50 g, 3.25 mmol) and diisopropylethyl amine (2.54 mL, 14.6 mmol) in DMF at rt. The reaction mixture was stirred at room temperature overnight (16 h), then half saturated aq. NaHCO$_3$ was added and the reaction mixture was extracted with TBME (3×). The organic phase was washed successively with water and brine, dried (Na$_2$SO$_4$) and concentrated in vacuo to give the crude product which was recrystallised from methanol (40 mL) to give 31 (0.85 g) as a white solid which was used in the next step without further purification.

$^1$H NMR (CDCl$_3$): 10.1 (s, 1H); 7.2 (d, 1H, J 8.7); 6.45 (d, 1H, J 8.7); 0.9 (s, 9H); 0.82 (s, 9H); 0.79 (s, 9H); 0.16 (s, 6H); 0.1 (s, 6H); 0.0 (s, 6H); −0.05 (s, 6H).

ii) 1,2,3-Tri(t-butyldimethylsilyloxy)-6-[(Z)-2-(3,4,5-trimethoxyphenyl)vinyl]-benzene, 32 n-Butyl lithium (0.89 mL, 2.23 mmol, 2.5 M in hexanes) was added dropwise over 10 min to a solution of 3,4,5-trimethoxybenzylphosphonium bromide (0.96 g, 1.83 mmol) in THF (10 mL) at −10° C. The reaction mixture was stirred at this temperature for 15 min then cooled to −70° C. and a solution of 31 (0.93 g, 1.88 mmol) in THF (4 mL) was added and the reaction mixture was allowed to warm to room temperature with stirring overnight. The reaction mixture was cooled to 0° C. and water was added. The reaction mixture was extracted with TBME (3×) and the organic phase was washed successively with water and brine, dried (Na$_2$SO$_4$) and concentrated in vacuo to give crude product (1.5 g). Purification by column chromatography (SiO$_2$; 5:95 TBME: cyclohexane+1% Et$_3$N) gave 32 compound (0.6 g, 50%) as a 86:14 mixture of Z:E isomers:

$^1$H NMR (CDCl$_3$): 6.75 (d, 1H, J 8.7); 6.55 (s, 2H); 6.45 (1H, d, J 12.3); 6.28 (d, 1H, J 8.7); 6.24 (d, 1H, J 12.3); 3.75 (s, 3H); 3.58 (s, 6H); 0.92 (s, 9H); 0.87 (s, 9H); 0.81 (s, 9H); 0.10 (s, 6H); 0.07 (s, 6H); 0.00 (s, 6H).

iii) 2,3,4-Trihydroxy-6-[(Z)-2-(3,4,5-trimethoxyphenyl)vinyl]-benzene, ZSB-79

Tetrabutylammonium fluoride (1.37 mL, 1.37 mmol, 1M in THF) was added to a solution of 32 (0.45 g, 0.69 mmol) and glacial acetic acid (78 µL, 1.37 mmol) in THF (6 mL) at 0° C. The reaction mixture was allowed to warm to room temperature overnight, then cooled to 0° C. and water was added. The reaction mixture was extracted with TBME (3×) and the organic phase was dried (Na$_2$SO$_4$) and concentrated in vacuo. The residue was partitioned between CH$_3$CN and cyclohexane and the CH$_3$CN layer was separated and concentrated in vacuo to give the crude product (0.27 g). Purification by column chromatography (SiO$_2$ 1:1 EtOAc:cyclohexane) gave ZSB-79 (0.127 g, 58%) as a 86:14 mixture of Z:E isomers:

LCMS: Rt 1.25; Mass found: 319 (MH$^+$).

$^1$H NMR (acetone-d6): 7.5 (br s, 3H); 6.45 (s, 2H); 6.44 (d, 1H, J 8.7); 6.42 (d, 1H, J 12.3); 6.27 (d, 1H, J 12.3); 6.17 (d, 1H, J 8.7); 3.56 (s, 3H); 3.51 (s, 6H).

i) 2,3-Dihydroxy-4-ethoxy-6-[(Z)-2-(3,4,5-trimethoxyphenyl)vinyl]-benzene, ZSB-81

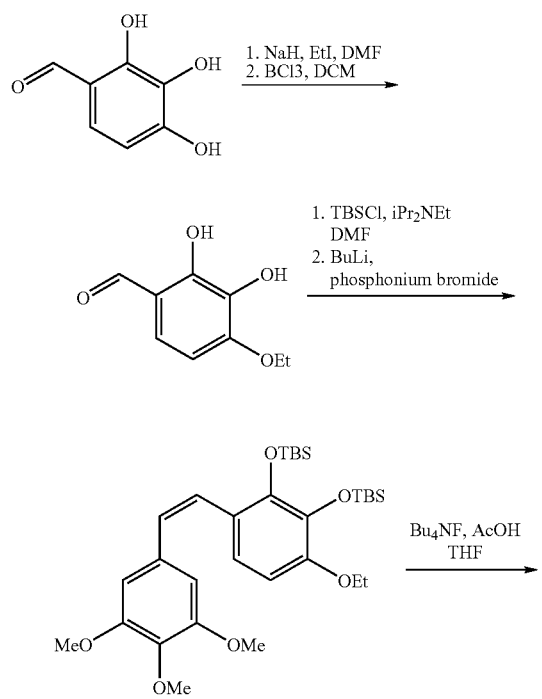

i) 2,3,4-Triethoxybenzaldehyde, 33

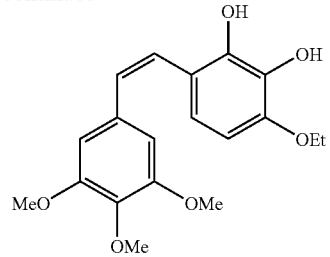

Sodium hydride (2.08 g, 51.9 mmol, 60% dispersion in oil) was added portionwise to a solution of 2,3,4-trihydroxybenzaldehyde (2.0 g, 13 mmol) in DMF (26 mL) at −1° C. The reaction mixture was stirred at this temperature for 45 min then iodoethane (3.4 mL, 42.9 mmol) was added and allowed to warm to room temperature overnight. The reaction mixture was cooled to 0° C., diluted in water, then extracted with TBME (3×). The organic phase was washed successively with water and brine, dried (Na$_2$SO$_4$) and concentrated in vacuo to give the crude product (1.4 g). Purification by column chromatography (SiO$_2$ 5:95 EtOAc:cyclohexane) gave 33 compound (0.80 g):

$^1$H NMR (CDCl$_3$): 10.2 (s, 1H); 7.58 (d, 1H, J 8.7); 6.75 (d, 1H, J 8.7); 4.25 (q, 2H, J 7.0); 4.15 (q, 2H, J 7.0); 4.10 (q, 2H, J 7.0); 1.48 (t, 3H, J 7.0); 1.41 (t, 3H, J 7.0); 1.40 (t, 3H, J 7.0).

LCMS: Rt 1.50 Mass found: 239 (MH$^+$).

ii) 4-Ethoxy-2,3-dihydroxybenzaldehyde, 34

A solution of boron trichloride (3.34 mL, 3.34 mmol 1M in DCM, 1 eq) was added dropwise to a solution of 33 (0.80 g, 3.34 mmol) in DCM at room temperature. The reaction mixture was stirred for 2 hours at this temperature then a further one equivalent of boron trichloride (3.34 mL, 3.34 mmol, 1M in DCM) was added and the reaction mixture was stirred at room temperature overnight. The reaction mixture was cooled to 0° C. and saturated NaHCO$_3$ aq. was added, then made acidic by the dropwise addition of conc. HCl. The reaction mixture was extracted with TBME (3×) and the organic phase was dried (Na$_2$SO$_4$) and concentrated in vacuo to give the crude product (1.4 g). Purification by column chromatography (SiO$_2$ 1:2 EtOAc:cyclohexane) gave 34 compound (0.46 g, 76%):

$^1$H NMR (CDCl$_3$): 11.1 (s, 1H); 9.75 (s, 1H); 7.10 (d, 1H, J 8.7); 6.60 (d, 1H, J 8.7); 5.48 (s, 11H); 4.23 (q, 2H, J 7.0); 1.51 (t, 3H, J 7.0).

iii) 4-Ethoxy-2,3-di(t-butyldimethylsilyloxy)benzaldehyde, 35

Diisopropylethylamine (1.44 mL, 8.32 mmol) was added to a solution of 34 (0.50 g, 2.8 mmol) and t-butyldimethylsilylchloride (0.92 g, 6.1 mmol) in DMF (4 mL) at room temperature The reaction mixture was stirred at room temperature overnight (16 h), then half saturated aq. NaHCO$_3$ was added and the reaction mixture was extracted with TBME (3×). The organic phase was washed successively with water and brine, dried (Na$_2$SO$_4$) and concentrated in vacuo to give the crude product (1.4 g), which was recrystallised from methanol to give 35 (0.47 g, 41%) as a white solid which was used in the next step as such:

$^1$H NMR (CDCl$_3$): 10.0 (s, 1H); 7.34 (d, 1H, J 8.7); 6.47 (d, 1H, J 8.7); 3.94 (q, 2H, J 7.0); 1.32 (t, 3H, J 7.0); 0.91 (s, 9H); 0.87 (s, 9H); 0.0 (s, 6H); −0.02 (s, 6H).

iv) 1,2-Di(t-butyldimethylsilyloxy)-3-ethoxy-6-[(Z)-2-(3,4,5-trimethoxyphenyl)vinyl]-benzene, 36 n-Butyl lithium (0.85 mL, 1.36 mmol, 1.6 M in hexanes) was added dropwise over 10 min to a solution of 3,4,5-trimethoxybenzylphosphonium bromide (0.58 g, 1.12 mmol) in THF (7 mL) at −10° C. The reaction mixture was stirred at this temperature for 15 min then cooled to −70 C and a solution of 35 (0.47 g, 1.14 mmol) in THF (3 mL) was added and the reaction mixture was allowed to warm to room temperature with stirring overnight. The reaction mixture was cooled to 0° C. and water was added. The reaction mixture was extracted with TBME (3×) and the organic phase was washed successively with water and brine, dried (Na$_2$SO$_4$) and concentrated in vacuo to give crude product (0.67 g). Purification by column chromatography (SiO$_2$ 2:98 EtOAc: cyclohexane+1% Et$_3$N) gave 36 (0.21 g, 34%) as an 89:11 mixture of Z:E isomers.

$^1$H NMR (CDCl$_3$): 6.79 (d, 1H, J 8.7); 6.46 (s, 2H); 6.44 (d, 1H, J 12.3); 6.24 (m, 2H); 3.85 (q, 2H, J 7); 3.72 (m, 5H); 3.51 (s, 6H); 1.32 (t, 3H, J 7); 0.93 (s, 9H); 0.90 (s, 9H); 0.07 (s, 6H); 0.00 (s, 6H).

v) 2,3-Dihydroxy-4-ethoxy-6-[(Z)-2-(3,4,5-trimethoxyphenyl)vinyl]-benzene, ZSB-81

Tetrabutylammonium fluoride (0.75 mL, 0.75 mmol, 1M in THF) was added to a solution of 36 (0.21 g, 0.375 mmol) and glacial acetic acid (43 μL, 0.75 mmol) in THF 7 mL at 0° C. The reaction mixture was allowed to warm to room temperature overnight, then cooled to 0° C. and water was added. The reaction mixture was extracted with TBME (3×) and the organic phase was dried (Na$_2$SO$_4$) and concentrated in vacuo. The residue was partitioned between CH$_3$CN and cyclohexane and the CH$_3$CN layer was separated and concentrated in vacuo to give the crude product. Purification by column chromatography (SiO$_2$ 1:1 EtOAc:cyclohexane) gave ZSB-81 (38 mg, 29%) as an 89:11 mixture of Z:E isomers:

LCMS: Rt 1.86; Mass found: 347 (MH$^+$).

$^1$H NMR (d6 acetone): 7.62 (br s, 1H); 7.42 (br s, 1H); 6.67 (d, 1H, J 8.7); 6.61 (s, 2H); 6.58 (d, 1H, J 12.3); 6.44-6.30 (m, 2H); 4.03 (q, 2H, J 7); 3.67 (s, 3H); 3.62 (s, 6H); 1.30 (t, 3H, J 7).

j) 2,3-Dihydroxy-4-allyloxy-6-[(Z)-2-(3,4,5-trimethoxyphenyl)vinyl]-benzene, ZSB-84

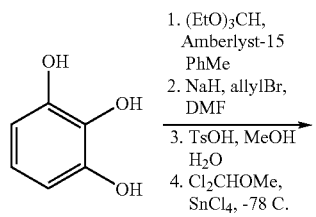

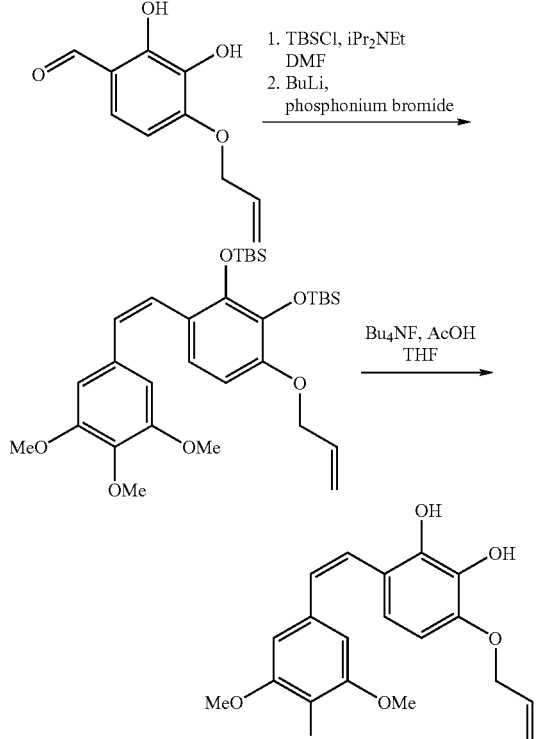

i) 2-Ethoxy-1,3-benzodioxol-4-ol, 37

Method adapted from J. Am. Chem. Soc. 1989, 111, 4832.

A 500 mL round bottom flask was charged with pyrogallol (25 g, 0.198 mol), triethyl orthoformate (40 mL, 35.6 g, 0.240 mol), toluene (250 mL) and Amberlyst-15 (2.40 g). A 40 cm long B24 reflux condenser was attached and on top of this a distillation head was connected to a condenser, receiver adaptor and 100 mL collecting flask. The reaction mixture was stirred and heated under reflux at a metal block temperature of 150° C. for 1 h. The water flow to the is reflux condenser was stopped and the water to the distillation condenser was turned on. Distillate boiling point up to 78° C. was collected over 4 h, after which the block temperature was increased to 260° C. for 30 min and finally 170° C. for 30 min. The toluene/ethanol azeotrope (43 mL) was collected and contained 68% ethanol. The red mixture was filtered through celite and the filtrate was evaporated to dryness. The residue was absorbed onto 60 mL of flash silica then applied to a column of 300 mL flash silica made up in heptane/EtOAc (9:1). Elution with this solvent mixture afforded 37 (26.2 g, 73%) as a very pale yellow oil:

$^1$H NMR (CDCl$_3$) δ 6.88 (s, 1H), 6.72-6.78 (m, 1H), 6.48-6.54 (m, 2H), 5.27 (br s, 1H), 3.74 (q, 2H, J 7.1), 1.26 (t, 3H, J 7.1).

ii) 4-Allyloxy-2-ethoxy-1,3-benzodioxolane, 38

A solution of 37 (4.0 g, 22.0 mmol) in DMF (7 mL) was added dropwise over 5 min to a suspension of sodium hydride (1.32 g, 33.0 mmol 60% dispersion in oil) in DMF (15 mL) at 0° C. The reaction mixture was stirred at this temperature for 15 min, then allyl bromide (2.93 g, 2.09 mL, 24.2 mmol) was added and the reaction mixture was allowed to warm to rt over 16 h. The reaction mixture was then cooled to 0° C., water was added dropwise, then the reaction mixture was extracted with t-BuOMe (3×). The organic phase was washed successively with water and brine, dried (Na$_2$SO$_4$) and evaporated to dryness to give 4.8 g of crude product. Purification by column chromatography (SiO$_2$ 2:98 EtOAc:cyclohexane) gave 38 compound (3.3 g, 68%):

$^1$H NMR (CDCl$_3$): δ 6.90 (s, 1H); 6.78 (t, 1H, J 8.2); 6.56 (d, 1H, J 8.0); 6.54 (d, 1H, J 8.4); 6.05 (ddt, 1H, J 17.3, 10.4, 5.5); 5.41 (dd, 1H, J 17.3, 1.3); 5.28 (d, 1H, J 10.4); 4.65 (d, 2H, J 5.5); 3.75 (q, 2H, J 7.1); 1.27 (t, 3H, J 7.1).

LCMS: Rt 1.51 Mass found: 222 (M$^+$).

iii) 3-Allyloxycatechol, 39

A solution of 38 (3.3 g, 15 mmol) and p-toluenesulfonic acid monohydrate (0.17 g, 0.9 mmol) in aqueous MeOH (21 mL, MeOH: H$_2$O 20:1) was stirred at rt for 16 h, then neutralised by the addition of saturated NaHCO$_3$ aq. and the methanol was removed in vacuo. The residue was extracted with t-BuOMe (3×) and the organic phase was dried (Na$_2$SO$_4$) and evaporated to dryness to give 39 compound (2.4 g, 95%) which was used as such in the next step:

$^1$H NMR (CDCl$_3$): δ 6.73 (t, 1H, J 8.2); 6.60 (dd, 1H, J 8.4, 1.3); 6.45 (dd, 1H, J 8.2, 1.3); 6.05 (ddt, 1H, J 17.3, 10.4, 5.6); 5.46-5.3 (m, 4H); 4.60 (dt, 2H, J 5.6, 1.3).

LCMS: Rt 0.58 Mass found: 166 (M$^+$).

iv) 4-Allyloxy-2,3-dihydroxybenzaldehyde, 40

Tin tetrachloride (0.31 g, 0.14 mL, 1.32 mmol) was added to a solution of 39 (0.20 g, 1.20 mmol) and αα'-dichloromethyl methyl ether (0.15 g, 0.12 mL, 1.32 mmol) in CH$_2$Cl$_2$ at −78° C. The pale brown reaction mixture was stirred at this temperature for 1.5 h, then poured into an excess of saturated NaHCO$_3$ aq. cooled at 0° C. The mixture was stirred for 15 min, acidified to pH 5 by the addition of 5% w/v citric acid then extracted with CH$_2$Cl$_2$ (3×). The organic phase was dried (Na$_2$SO$_4$) and evaporated to dryness to give 40 compound (0.18 g, 76%) which was used as such in the next step.

$^1$H NMR (CDCl$_3$): δ 11.1 (s, 1H); 9.76 (s, 1H); 7.10 (d, 1H, J 8.6); 6.61 (d, 1H, J 8.6); 6.06 (m, 1H); 5.5-5.3 (m, 3H); 4.70 (d, 2H, J 5.5).

LCMS: Rt 1.04 Mass found: 195 (MH$^+$).

v) 4-Allyloxy-2,3-di(t-butyldimethylsilyloxy)benzaldehyde, 41

Diisopropylethylamine (0.35 g, 0.48 mL, 2.75 mmol) was added to a solution of 40 (0.18 g, 0.92 mmol) and t-butyldimethylsilyl chloride (0.30 g, 2.0 mmol) in DMF (4 mL) at rt. The reaction mixture was stirred at rt for 16 h then poured into half saturated NaHCO$_3$ aq. and extracted with t-BuOMe (3×). The organic phase was dried (Na$_2$SO$_4$) and evaporated to dryness. Purification by column chromatography (SiO$_2$ 2:98 EtOAc:cyclohexane) gave 41 compound (0.14 g, 35%):

$^1$H NMR (CDCl$_3$): δ 10.1 (s, 1H); 7.30 (d, 1H, J 8.2); 6.51 (d, 1H, J 8.1); 5.95 (m, 1H); 5.3-5.1 (m, 2H); 4.42 (d, 2H, J 5.5); 0.90 (s, 9H); 0.79 (s, 9H); 0.05 (s, 12H).

LCMS: Rt 2.33 Mass found 423 (MH$^+$).

vi) 1,2-Di-(t-butyldimethylsilyloxy)-3-allyloxy-6-[(Z)-2-(3,4,5-trimethoxyphenyl)vinyl]-benzene, 42 n-Butyllithium (0.37 mL, 0.59 mmol, 1.6 M in hexanes) was added dropwise over 5 min to a solution of 3,4,5-trimethoxybenzylphosphonium bromide (0.27 g, 0.52 mmol) in THF (3 mL) at −10° C. The reaction mixture was stirred at this temperature for 15 min then cooled to −70° C. and a solution of 41 (0.10 g, 0.24 mmol) in THF (3 mL) was added and the reaction mixture was allowed to warm to rt with stirring overnight (16 h). The reaction mixture was cooled to 0° C. and water was added. The reaction mixture was extracted with t-BuOMe (3×) and the organic phase was washed successively with water and brine, dried (Na$_2$SO$_4$) and evaporated to dryness to give crude product (0.3 g). Purification by column chromatography (SiO$_2$ 2:98 EtOAc:cyclohexane) gave 42 (83 mg, 60%) as an 85:15 mixture of Z:E isomers.

$^1$H NMR (CDCl$_3$): δ 6.90 (d, 1H, J 8.7); 6.61 (s, 2H); 6.59 (d, 1H, J 12.2); 6.38 (m, 2H); 6.12-6.0 (m, 1H); 5.32 (dd, 1H, J 14.9, 1.4); 5.24 (dd, 1H, J 10.5, 1.4); 4.44 (d, 2H, J 5.9); 3.85-3.80 (m, 9H); 1.02 (s, 9H); 1.00 (s, 9H); 0.10 (s, 6H); 0.05 (s, 6H).

LCMS: Rt 1.20 Mass found 317.

vii) 1,2-Dihydroxy-3-allyloxy-6-[(Z)-2-(3,4,5-trimethoxyphenyl)vinyl]-benzene, ZSB-84

Tetrabutylammonium fluoride (0.24 mL, 0.24 mmol, 1M in THF) was added to a solution of 1,2-di(t-butyldimethylsilyloxy)-3-allyloxy-6-[(Z)-2-(3,4,5-trimethoxyphenyl)vinyl]-benzene (69 mg, 0.120 mmol) and glacial acetic acid (14 μL, 0.24 mmol) in THF 4 mL at 0° C. The reaction mixture was allowed to warm to rt overnight, then cooled to 0° C. and water was added. The reaction mixture was extracted with t-BuOMe (3×) and the organic phase was dried (Na$_2$SO$_4$) and evaporated to dryness. Purification by column chromatography (SiO$_2$ 3:7 EtOAc:cyclohexane) gave ZSB-84 (36 mg, 84%) as an 96:4 mixture of Z:E isomers:

$^1$H NMR (d6-acetone): δ 7.63 (br s 1H); 6.71 (d, 1H, J 8.6); 6.65 (s, 2H); 6.62 (d, 1H, J 12.3); 6.45 (d, 1H, J 12.2); 6.43 (d, 1H, J 8.6); 6.06 (m, 1H); 5.42 (d, 1H, J 17.2); 5.24 (d, 1H, J 10.5); 4.58 (d, 2H, J 5.3); 3.72 (s, 3H); 3.65 (s, 6H).

LCMS: Rt 1.40 Mass found 359 (MH$^+$).

k) 4-Nitro-6-[(Z)-2-(3,4,5-trimethoxyphenyl)vinyl]-2,3-dihydroxybenzene, ZSB-83

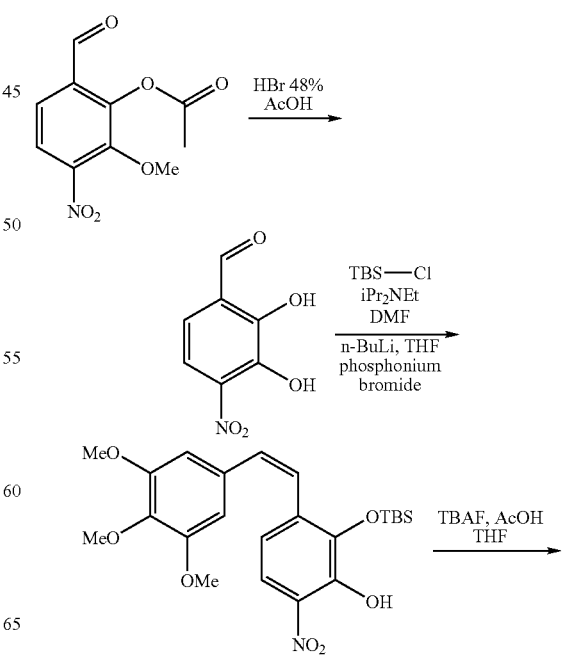

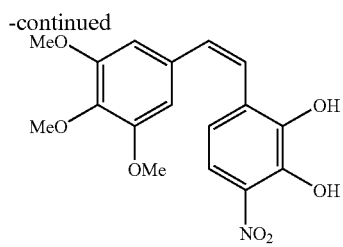

i) 2-Acetoxy-3-methoxybenzaldehyde, 42

Acetic anhydride (45.9 g, 0.45 mol) was added to a suspension of 3-methoxysalicylaldehyde (45.6 g, 0.3 mol) and $K_2CO_3$ (42.0 g, 0.6 mol) in $CH_2Cl_2$ (450 L) at rt. The reaction mixture was stirred at rt overnight then filtered, evaporated and the residue was recrystallised from cyclohexane to give 42 (42.0 g, 74%) as colourless needles:

$^1$H NMR (CDCl$_3$) δ 10.13 (s, 1H), 7.46-7.50 (m, 1H), 7.30-7.39 (m, 1H), 7.20-7.24 (m, 1H), 3.88 (s, 3H), 2.42 (s, 3H).

ii) 2-Acetoxy-3-methoxy-4-nitrobenzaldehyde, 43

42 (42.0 g, 0.22 mol) was added portionwise as a finely ground powder over 1 h to a solution of concentrated sulphuric acid (28 mL) in 100% nitric acid (140 mL) at −20° C. During the addition, the reaction temperature was maintained at around −15° C. The reaction mixture was stirred at −5° C. for a further 40 min, then poured into to ice/water (1 L) and extracted rapidly with toluene (2×). The organic phase was washed successively with 0.25 M NaHCO$_3$ aq. water and brine, dried (Na$_2$SO$_4$) and evaporated to dryness to give crude product (19.8 g) as a yellow oil, which was shown by NMR to contain ~60% nitro-compounds. Purification of 8 g of this material by column chromatography (three times, SiO$_2$, first eluting with 1:9 EtOAc:cyclohexane, then with 3:7 EtOAc:cyclohexane and finally with 1:1 EtOAc:cyclohexane) gave 43 (2.53 g) in (~80% purity) together with 2-hydroxy-3-methoxy-4-nitrobenzaldehyde (~10%). The product was used as such in the next step.

iii) 2,3-Dihydroxy-4-nitrobenzaldehyde, 44

43 (2.5 g, 10.5 mmol) was added to a solution of acetic acid (62.5 mL) and hydrobromic acid 48% (70 mL) and the reaction mixture was heated at 150° C. for 4 h. The reaction mixture was then cooled to rt and evaporated to dryness. The residue was diluted in hot CH$_2$Cl$_2$ (40 mL) and filtered. The filtrate was evaporated to dryness to give 44 (1.74 g, 91%) which was used as such in the next step:

$^1$H NMR (CDCl$_3$): 10.60 (1H, s); 10.04 (1H, s); 7.77 (2H, d, J 14); 7.26 (1, d, J 14)

iv) 2,3-Di(t-butyldimethylsilyloxy)-4-nitro benzaldehyde, 45

Diisopropylethylamine (4.9 mL, 27.9 mmol) was added dropwise to a solution of 44 (1.7 g, 9.3 mmol) and t-butyldimethylsilyl chloride (3.13 g, 20.8 mmol) in DMF (34 mL) at rt. The reaction mixture was stirred at rt overnight, then diluted with t-BuOMe and washed with water. The aqueous layer was re-extracted with t-BuOMe and the combined organic extracts were washed with brine, dried (Na$_2$SO$_4$) and evaporated to dryness to give 45 (0.88 g, 23%) which was used as such in the next step:

$^1$H NMR (CDCl$_3$): 10.42 (1H, s); 9.85 (1H, s); 7.67 (1H, d, J 14.5); 7.28 (1H, d, J 14.5); 0.94 (9H, s); 0.87 (9H, s); 0.21 (6H, s); 0.16 (6H, s).

v) 3-Nitro-6-[(Z)-2-(3,4,5-trimethoxyphenyl)vinyl]-1-(t-butyldimethylsilyloxy)-2-hydroxybenzene, 46 n-Butyllithium (1.6 mL of a 1.6 M solution in hexane, 2.6 mmol) was added dropwise to a suspension of 3,4,5-trimethoxybenzyltriphenylphosphonium bromide (1.1 g, 2.1 mmol) in THF (15 mL) at −20° C. The brick red solution was stirred at −20° C. for 30 min, cooled to −78° C., then a solution of 45 (0.88 g, 2.14 mmol) in THF (5 mL) was added dropwise. The reaction mixture was allowed to warm to rt overnight, then poured into t-BuOMe (ca. 20 mL) and water (ca. 20 mL), the layers were separated and the aqueous layer was re-extracted with t-BuOMe. The combined organic extracts were washed with brine, dried (Na$_2$SO$_4$) and evaporated to dryness. Purification by column chromatography (SiO$_2$, EtOAc:cyclohexane 1:1) gave 46 (0.355 g, 29%):

$^1$H NMR (CDCl$_3$): 10.99 (1H, s); 7.73 (1H, d, J 9.3); 7.48 (1H, d, J 16.6); 7.23 (1H, d, J 9.3); 7.13 (1H, d, J 16.4); 6.78 (2H, s); 3.91 (6H, s); 3.89 (3H, s); 1.09 (9H, s); 0.29 (6H, s).

vi) 3-Nitro-6-[(Z)-2-(3,4,5-trimethoxyphenyl)vinyl]-1,2-dihydroxybenzene, ZSB-83

Tetrabutylammonium fluoride (0.77 mL, 0.769 mmol, 1M in THF) was added to a solution of 46 (0.355 g, 0.769 mmol) and glacial acetic acid (0.04 mL, 0.769 mmol) in THF (4 mL) at rt. The reaction mixture was stirred at rt for 3 h then diluted with t-BuOMe and washed successively with water and brine. The organic layer was dried (Na$_2$SO$_4$) and evaporated to dryness to give a crude product which was purified by column chromatography (three times—first with: EtOAc:cyclohexane 3:7+1% acetic acid, then with neat CH$_2$Cl$_2$ and finally with CH$_2$Cl$_2$:methanol 40:1) to yield ZSB-83 (65 mg, 25%):

$^1$H NMR(CDCl$_3$): 10.83 (1H, s); 7.65 (1H, d, J 9.3); 7.27 (2H, s); 7.17 (1H, d, J 9.3); 6.79 (2H, s); 6.09 (1H, s); 3.91 (6H, s); 3.88 (3H, s).

LCMS: Rt 1.41.

Mass found: 348 (MH$^+$).

l) No Methoxy A Ring CA4

The synthesis of this molecule is indicated in FIG. 3.

i) Benzyltriphenylphosphonium Bromide 47

To a well-stirred solution of benzyl bromide (2.736 g, 16 mmol) was dissolved in CH$_2$Cl$_2$ (50 mL) and triphenylphosphite (4.62 g, 17.6 mmol.) was added. The reaction was heated overnight and then ice-cold water was added and the product was isolated by extraction with CH$_2$Cl$_2$. The organic phase was washed with brine and dried over sodium sulfate. Evaporation of the solvent in vacuo resulted in a crude solid, which was recrystallized from ethyl alcohol/heaxane to afford 47 as colorless crystals (6.24 g, 90%)

R$_f$ 0.00 (hexane-ethyl acetate 1:1).

$^1$H-NMR (300 MHz, CDCl$_3$): δ 5.32 (2H, d, J=15 Hz), 7.10 (3H, m), 7.13 (1H, m), 7.70 (15H, m).

ii) 2,3-Dihydroxy-4-methoxybenzaldehyde, 48

An anhydrous dichloromethane (50 ml) solution of 2,3,4-trimethoxybenzaldehyde (1.96 g, 10 mmol) under argon at room temperature was stirred for 10 min and boron trichloride (10 ml, 10 mmol, 1 eq; 1.0 M solution in dichloromethane) was added. After 2 h, the second equivalent of boron trichloride (10 ml, 10 mmol, 1 eq; 1.0 M solution of dichloromethane) was added. The dark reaction mixture was stirred overnight and then slowly poured into 10% sodium bicarbonate (aq) (4 g/36 ml). The resulting solution was acidified with concentrated hydrochloride acid to pH 1. The dichloromethane layer was separated, and the aqueous layer extracted with ethyl acetate (4×20 ml) and dried. Evaporation of solvent in vacuum gave brown oil, which was further separated by column chromatography (1:1 hexane-ethyl acetate) to afford a yellow solid. Recrystallization from ethyl acetate-hexane gave a pale yellow needle of 48 (1.1 g, 65.5%); $R_f$ 0.40 (hexane:ethyl acetate: 1:1).

iii) 2,3-Bis-[tert-butyldimethylsilyloxy]-4-methoxyblenaldehyde, 49

Diiospropylethylamine (1.8 ml) was added to a stirred solution (under argon) of 38 (840 mg, 5 mmol) in DMF (10 ml) followed by tert-butyldimethylsilyl chloride (1.12 g, 7.5 mmol) and this solution mixture was stirred at room temperature for 45 min. After 25 min, ice-cold water (20 ml) was added and the mixture was extracted with ether (4×25 ml). The organic layer was washed with ice-water (20 ml), saturated NaHCO$_3$ solution (20 mL) and dried over sodium sulfate. The solvent was rotovapored under reduced pressure to yield a light brown oil that was purified by column chromatography (SiO$_2$, hexanes-ethyl acetate 16:1) to yield the bis-silyl ether (1.58 g, 4 mmol, 80%) as a light yellow oil which could be crystallized from methanol to afford 49 as a colorless solid. $R_f$ 0.80 (hexanes-ethyl acetate 15:1).

iv) Z-1-(2'-3'-(tert-butyldimethylsilyl)-4'-methoxy-oxyphenyl)-2-phenylethene, 50

Butyllithium (1.2 ml, 2.5M in THF) was added to a suspension of benzyltriphenylphosphonium bromide (1.299 g, 3 mmol) in THF (50 mL) at –15° C. The resulting deep reddish solution was allowed to warm to room temperature while stirring for 30 min. The 49 (1.11 g, 2.8 mmol) was added after this time, changing the color from a deep red to orange. This solution was allowed to stir for 3 hours at room temperature. After this time, the reaction mixture was diluted with ice-cold water (25 mL) and extracted with ether (4×25 mL). The organic phase was washed with water (2×25 mL). The solvent was removed under reduced pressure to afford the product as a dark brown oil (Z:E mixture, 1.2:1). The Z isomer was obtained following column chromatography (SiO$_2$, hexanes: ethyl acetate, 18:1 (2×)). The protected Z stilbene 50 was afforded (461.4 mg, 35%) as an off-white solid.

$^1$H-NMR (300 MHz, CDCl$_3$): δ 0.19 (6H, s), 0.26 (6H, s), 1.07 (9H, s), 1.10 (9H, s), 3.79 (3H, s), 6.38 (1H, d, J=8.5 Hz), 6.50 (1H, d, J=12 Hz), 6.75 (1H, d, J=12 Hz), 6.89 (1H, d, J=8 Hz), 7.26 (3H, m), 7.39 (2H, d, J=8 Hz). $^{13}$C-NMR (300 MHz, CDCl$_3$): δ 162.73, 152.06, 146.45, 138.01, 137.31, 129.22, 128.45, 127.94, 127.19, 123.8, 122.08, 104. 85, 55.27, 26.81, 26.62, 19.22, 18.99, –2.87, –3.34.

v) Z-1-(2',3'-dihydroxy-4'methoxy-phenol)-2-phenylethene, 51

To a solution of 50 (460 mg, 0.97 mmol), in anhydrous THF (10 ml) was added tetrabutylammonium fluoride (1M in 2.16 ml of THF, 2.16 mmol, 2.2 eq). The mixture was stirred at room temperature and the reaction was monitored by TLC. After 25 min, ice-cold 6N hydrochloride acid (aq) was added, and the mixture was extracted with ethyl acetate (4×20 mL). The combined extracts were washed with saturated sodium chloride (aq) and dried over sodium sulfate. Removal of the solvent under reduced pressure yielded a dark brown oil, which was separated by column chromatography to afford 51 as a white power (168 mg, 69.3%):

$^1$H-NMR (300 MHz, CDCl$_3$): δ 3.88 (3H, s), 5.48 (2H, bs), 6.36 (1H, d, J=8.6 Hz), 6.66 (2H, s), 6.72 (1H, d, 8.6 Hz), 7.24 (5H, m). $^{13}$C-NMR (300 MHz, CDCl$_3$): δ 146.3, 141.7, 137.3, 132.5, 130.3, 128.8, 128.2, 127.1, 124.5, 120.3, 117.9, 102.9, 56.1.

m) 2',3' dihydroxy-3,5 dichloro-4,4'-dimethoxy-(Z)-stilbene, ZSB-70

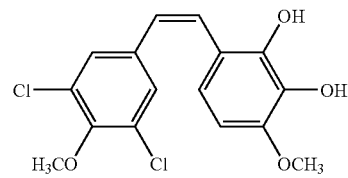

n) 2',3' dihydroxy-4'-methoxy-3,4,5-trifluoro-(Z)-stilbene, ZSB-71

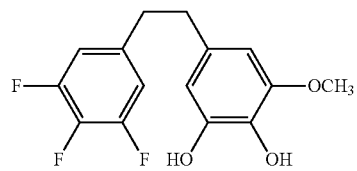

o) 2,3-Dihydroxy-4-methoxy-[(Z)-2-(3,4,5-trimethoxyphenyl) Beta lactam]-benzene

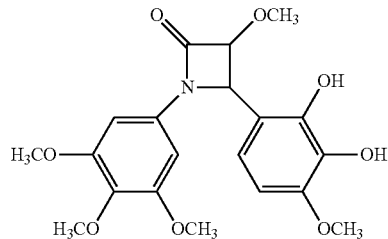

$^1$H NMR: δ 6.81 (d, 1H, J=8.67 Hz), 6.63 (s, 2H), 6.48 (d, 1H, J=8.69 Hz), 5.55 (d, 1H, J=4.86 Hz), 4.85 (d, 1H, J=4.87 Hz), 3.87 (s, 3H), 3.79 (s, 1H), 3.77 (s, 3H), 3.75 (s, 6H), 3.32 (s, 3H).

$^{13}$C NMR: δ 164.39, 153.46, 146.74, 142.33, 134.64, 133.28, 132.05, 119.56, 112.55, 103.00, 95.07, 84.53, 60.92, 58.77, 56.08, 56.00, 55.85.

Example 3

Diphosphate Prodrugs

CA1P prodrug is activated when phosphate moieties are removed from the molecule by phosphatases that are ubiquitous in mammalian blood and tissue. Dephosporylation of the drug produces an ortho-catechol that is able to bind tubulin associated with vascular endothelia and interfere with the flow of blood to tumor regions. The ortho-catechol is highly unstable and is capable of autooxidizing to form a semi-quinone and quinone moiety, both of which are known to produce highly reactive oxygen species (ROS) that are highly cytotoxic to tumor cells by virtue of their damaging effects on tumor cell membranes, lipid peroxidation, DNA damage, and depolymerization of macromolecules. In addition, the quinone species of the This second cytotoxic activity increases the molecules ability to kill tumor cells. Therefore, phosphorylation is thought to stabilize the highly unstable catechol and quinone, and delay their formation until the prodrug is administered to a patient.

Phosphate Prodrugs can be performed in a manner similar to the following reaction:

a) Tetrasodium-Z-1-(2',3'-diphosphoryl-4'-methoxy-phenyl)-2-phenylethene, 53

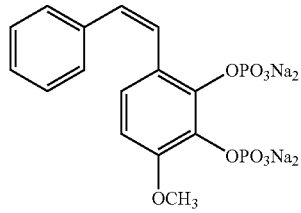

i) Z-1-(2',3'-dibenzylphosphoryl-4'methoxy-phenyl)-2-phenylethene, 52

The Z-isomer 51 (150 mg, 0.62 mmol) was dissolved in acetonitrile (15 mL) in a round bottom flask equipped with a septum, thermometer, and $N_2$ inlet. After cooling to −20° C., $CCl_4$ (0.6 mL) was added. The resulting solution was stirred for 10 min prior to adding diisopropylethylamine (Hunig's base) (0.5 mL) followed by DMAP (15 mg). About 2 min later, the slow addition of dibenzyl phosphite (0.5 mL) was begun at such a rate that the reaction temperature remained below −20° C. After the completion of the reaction (in 45 minutes by TLC monitoring), 0.5M $KH_2PO_4$ (10 mL) was added, and the solution was allowed to warm up to ambient temperature and extracted with ethyl acetate (3×20 mL). The combined solvent extract was washed with water (20 mL) and brine (20 mL), and then dried over $NaSO_4$. Removal of solvent in vacuum gave a yellow oil that was further separated by column chromatography ($SiO_2$, hexanes: ethyl acetate 6:4), yielding the dibenzyl phosphorylated Z-isomer 52 (415 mg, 88%) as a light yellow oil.

$^1$H-NMR (300 MHz, $CDCl_3$): δ 3.78 (3H, s), 5.16 (4H, m), 5.26 (4H, m), 6.64 (2H, d, J=11 Hz), 6.74 (1H, d, J=12 Hz), 7.03 (1H, d, J=8.8 Hz.), 7.31 (25H, m). $^{13}$C-NMR (300 MHz, $CDCl_3$): δ 171.5, 151.9, 141.8, 137.2, 136.5, 136.4, 136.2, 136.1, 131.8, 129.2, 128.9, 128.8, 128.4, 128.2, 127.6, 127.0, 124.9, 109.7, 56.7. $^{31}$P-NMR (300 MHz, $CDCl_3$): δ −5.46, −5.53.

ii) Tetrasodium-Z-1-(2',3'-diphosphoryl-4'-methoxy-phenyl)-2-phenylethene, 53

To a solution of 52 (230 mg, 0.3 mmol) was dissolved in dry acetonitrile (10 mL) at room temperature. After 2 min of stirring under argon, the distilled bromotrimethylsilane (TMSBr) (0.16 mL, 4.0 eq.) was added (dropwise) to the reaction during the 5 min period. After 30-45 min, HPLC confirmed completion of the debenzylation, the reaction was quenched with a solution of sodium methoxide (64.82 mg, 4 eq.) in methanol and allowed to sit for 1 hour. The product was filtered out and washed with 50% methanol/acetone. The crude solid was dissolved in a small amount of water; additional ethanol was added to precipitate the compound out. The product was collected and dried to provide 53 (58 mg, 40%).

$^1$H-NMR (300 MHz, $CDCl_3$): δ 3.80 (3H, s), 6.53 (1H, d, J=8.5 Hz), 6.63 (1H, d, J=12 Hz), 6.88 (1H, d, J=8.6 Hz), 7.08 (1H, d, J=12 Hz), 7.30 (3H, m), 7.43 (2H, d, J=7.3 Hz). $^{13}$CNMR (300 MHz, $CDCl_3$): δ 165.65, 152.57, 125.77, 145.67, 137.99, 136.23, 136.14, 129.01, 128.38, 128, 226, 127.7, 126.86, 126.24, 124.31, 123.47, 106.79, 55.76. $^{31}$P-NMR (300 MHz, $CDCl_3$): δ 1.25, 0.93.

b) 2',3'diphosphate-3,4,5-trimethoxy-(Z)-stilbene, tetrasodium salt; ZSB-36

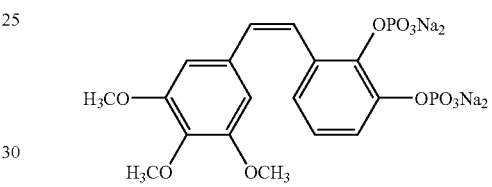

c) 3',4'diphosphate-3,4,5-trimethoxy-(Z)-stilbene, tetrasodium salt; ZSB-37

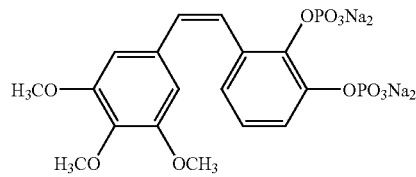

Example 4

Properties of Catechol Compounds a) Tubulin Binding Activity

The method of Verdier-Pinard (1998, Molec. Pharmacol. 53, 62-76) was used to assay catechol compounds for inhibition of tubulin polymerization. Tubulin polymerization was followed turbidimetrically at 350 nm on an Agilent 8453 spectrophotometer equipped with a kinetics program, a jacketed cell holder, and two microprocessor-controlled water baths. Purified tubulin (1 mg/ml) was induced to polymerize in a monosodium glutamate/GTP solution by a jump in temperature. Absorbance was recorded every 10 seconds and the data was analyzed by a GraphPad Prism program. Results are summarized in Table 2.

b) Tumor Cell Cytotoxicity

Exponentially growing tumor cells were treated with the following compounds for 24 hours. Insoluble compounds were formulated in a small amount (0.3%) of DMSO for biological evaluation. Cell viability was determined by the calorimetric MTT assay using 3(4,5-dimethylthiazol-2-yl)-2,5-diphenyl-2H-tetrazolium bromide according to well-established procedures (see Berridge, et al. (1996) for a general protocol of this type of assay). The results are shown in Table 2.

c) Reduction in Tumor Blood Flow

Catechols were dissolved in 50% DMSO (2 mg/kg) prior to intravenous (iv) administration (i.v.) to tumor-bearing mice. MHEC-5T tumors were established by subcutaneous injection of $0.5 \times 10^6$ cultured MHEC5-T cells (German Collection of Microorganisms and Cell Culture, Braunschweig, Germany) into the right flank of Fox Chase CB-17 severe combined immunodeficient (SCID) mice. Tumor grafts grew palpable within one week and reached the limited size (15×15 mm) within 10 days. Tumor bearing mice were injected intraperitoneally with saline control or various dosages of CA1P or CA4P after the transplanted tumor reached a size of 300 mm$^3$ (a size without development of necrosis). Twenty-four hours later they were injected with 0.25 ml of fluorescent FluoSphere beads (0.1 μm beads conjugated with blue fluorescent tag (F-8789, Molecular Probes, Eugene, Oreg.) and diluted 1:6 in physiological saline) in the tail vein, and sacrificed after 3 minutes. Tumors were then excised for cryosections. Cryosections of 8 μm thickness were directly examined under a fluorescent microscope. Functional blood vessels were indicated by blue fluorescence from injected microbeads. For quantification, three sections from three tumors treated in each group were examined and in each section, more than 70% of the area was automatically recorded with a microscopic digital camera at ×10 magnification. A computer program named Stage Pro (Media Cybernetics, Md.) was used to control the picture recording. Image analysis was performed with Image Plus software (Media Cybernetics, Md.). The results were expressed as vessel area per mm$^2$ in percentage of the control in Table 2.

TABLE 2

Catechol Properties

| Catechol | Tubulin Binding (uM IC50) | MTT (uM IC50) | Blood Flow at 10 mg/kg (% vessel area of control) |
|---|---|---|---|
| CA1 | 1.9 | 0.0046 | 30 |
| ZSB-36 | | 0.4 | 94 |
| ZSB-37 | | 0.073 | 80 |
| ZSB-70 | | | |
| ZSB-71 | | 0.887 | 46.7 |
| ZSB-74 | 2.1 | 0.34 | |
| ZSB-75 | | 0.9 | |
| ZSB-76 | | 0.542 | |
| ZSB-77 | | 0.748 | |
| ZSB-78 | | 0.546 | |
| ZSB-79 | | 0.069 | 26.7 |
| ZSB-80 | | 1.562 | |
| ZSB-81 | | 0.094 | |
| ZSB-82 | 6.2 | 0.143 | |
| ZSB-83 | | 0.28 | |
| ZSB-84 | | 0.007 | 60 |

Example 5

Production of Quinone and Reactive Oxygen Species

The inventors have made the surprising discovery that CA1 is readily oxidized to its their corresponding quinones with the concomitant production of tumor cytotoxic ROS free radicals, including the ones discussed specifically herein. Oxidation to an ortho-quinone can result in oxidative damage to the tumor via redox cycling. This is a process in which the quinone is reduced to a radical (ie. semiquinone), which in turn reduces oxygen to superoxide radicals with quinone being reformed or cycled. The generation of a quinone derivative was demonstrated and the quinone was found to react rapidly with the reducing agents glutathione and ascorbate. In addition, a rapid consumption of oxygen in the presence of ascorbate confirmed the formation of CA1 quinone. Furthermore, redox-cycling, confirming the formation of CA1 semiquinone, was observed with CA1.

a) Production and Characterization of the Qinone Formed on Oxidation of its Corresponding Catechol The formation of each quinone was examined by reacting its corresponding catechol with excess FeCl$_3$/H$_2$SO$_4$ and monitoring the reaction by HPLC. The identity of each quinone was confirmed by HPLC-MS (mass 330, $\lambda_{max}$ 312, 422 nm).

The ortho-quinone derivative was found to react rapidly with glutathione and ascorbate. As illustrated in FIG. 1A, stopped-flow rapid mixing of CA1 with excess of glutathione or ascorbate antioxidants resulted in a rapid loss of ortho-quinone absorbance. Measurement of the products by HPLC following reaction with glutathione demonstrated the presence of a new polar product. The data suggest that this new product is the quinone-glutathione adduct, since this HPLC peak was not observed after reaction of the quinone with ascorbate.

b) Redox Cycling with Ortho-Quinone and Antioxidants

Figure 1B:
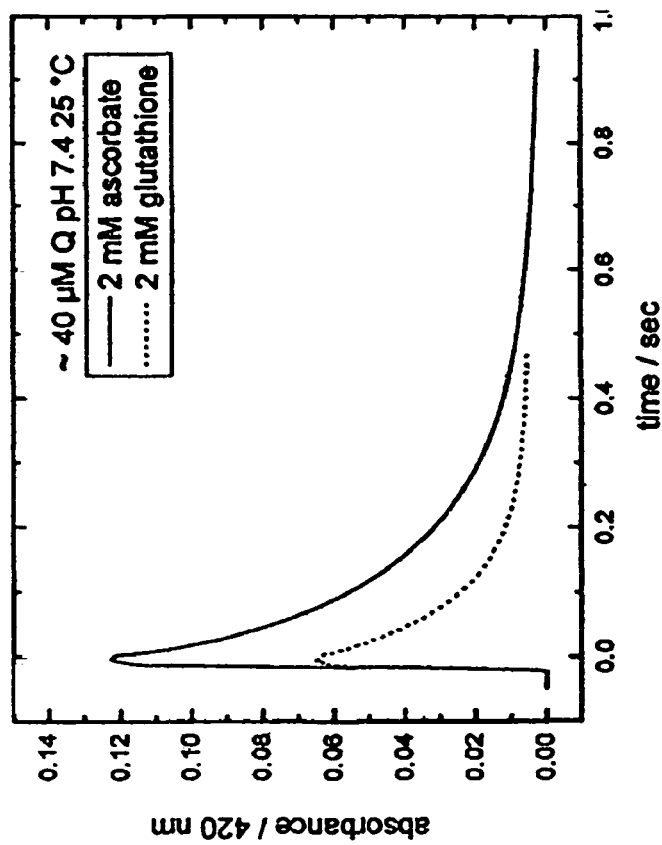
FIG. 1B illustrates the rapid consumption of oxygen when a reducing agent is added to a solution of Combretastatin A-1 ortho-quinone.

Phenolic compounds such as CA1 can also stimulate oxidative stress in tumor tissue by causing redox-cycling. This is a process in which the quinone of CA1 is reduced to a radical, in turn reducing oxygen to superoxide radicals with the quinone being re-formed or cycled. In order to examine if CA1 participates in redox-cycling, oxygen consumption was measured using suspensions of mouse liver homogenate and a Clark-type electrode. In this experiment, a rapid consumption of oxygen was observed when ascorbate was added to the quinone (refer to FIG. 1B). Furthermore, glutathione also was demonstrated to increase oxygen consumption when added to the quinone but the kinetics were different than that observed with ascorbate (refer to FIG. 1B).

In blood, the ortho catechol CA1 is susceptible to oxidation. This results in low or irreproducible recoveries with CA1 from plasma. The recovery of CA1 was resolved by incorporation of ascorbic acid as an antioxidant in the extraction mixture. In the presence of ascorbic acid the recovery of CA1 from plasma was increased to approximately 90%.

c) Formation of CA1 Quinone by HL-60 Tumor Cells

Figure 2A:
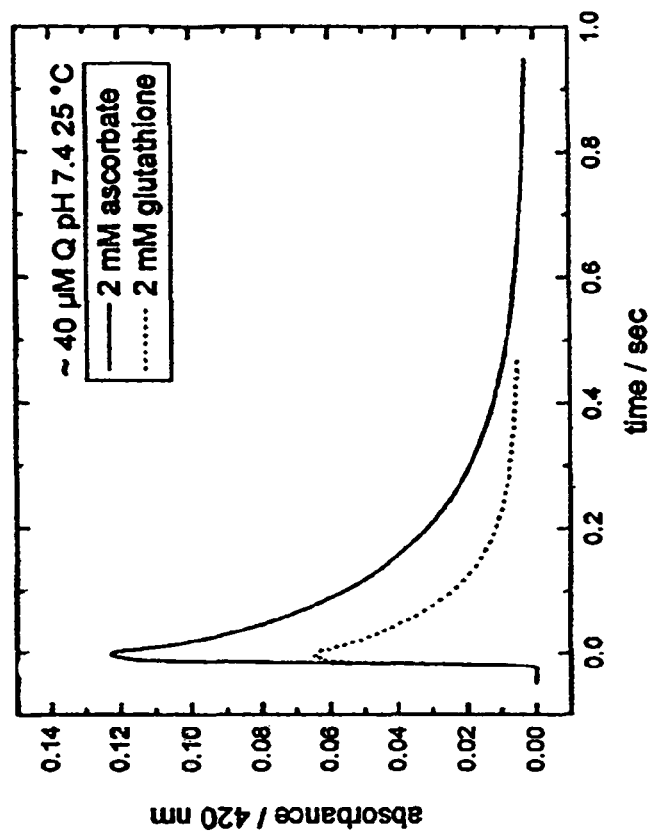
FIG. 2A illustrates the oxidative activation of the ortho-catechol, Combretastatin A-1 upon addition to HL-60 (human promyelocytic leukaemia) cells in the presence or absence of superoxide dismutase (SOD).
Figure 2B:
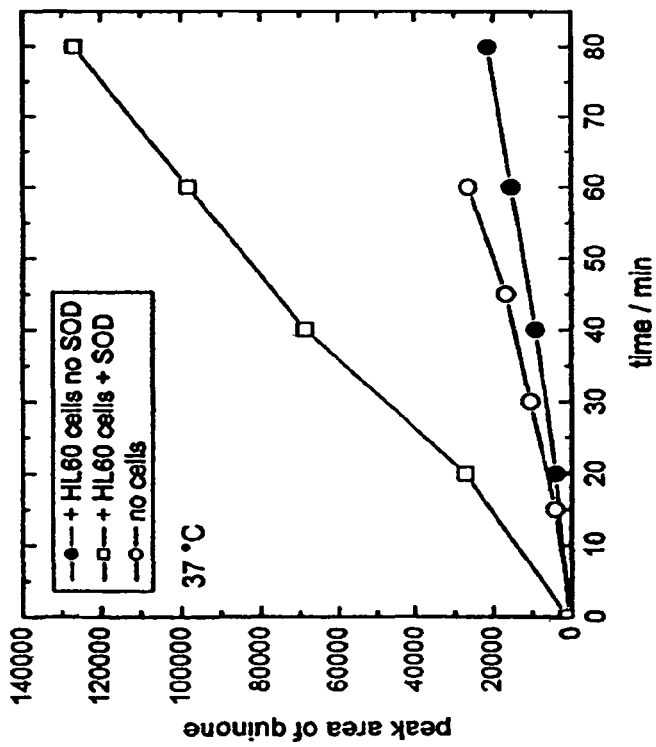
FIG. 2B is a HPLC chromatogram illustrating the separation of Combretastatin A1 and the Combretastatin A-1 ortho-quinone following incubation with HL-60 cells.

In the presence of peroxidases, CA1 is expected to generate the ortho quinone metabolite. HL-60 (human promyelocytic leukemia) cells are rich in myeloperoxidase and should initiate peroxidase-catalyzed oxidation of catechols. CA1 was shown to be oxidized to the quinone in the presence of HL-60 cells. Additionally, CA1 was shown to be oxidized at a faster rate in the presence of both HL-60 cells and superoxide dismutase (SOD) (refer to FIG. 2A). These results suggest that CA1 is oxidized to the quinone and recycled back to CA1 by superoxide radicals. Thus, by reducing the lifetime of superoxide radicals by adding SOD prevents quinone reduction. Interestingly when SOD was present, the formation of the trans form of CA1 was reduced. (refer to FIG. 2B). This is consistent with the semiquinone radical being generated from superoxide, conjugation in the radical allowing isomerization to the trans form.

d) Formation of Quinones by Peroxidase

Other peroxidases which may preferentially activate catechols in the presence of proliferating vasculature. Horseradish peroxidase (HRP) was utilized in the following experiment to oxidize a number of catechols to their corresponding ortho-quinones in vitro.

Methods: catechols were dissolved in DMSO immediately prior to assay (10 mM). HRP (Sigma, P6782, 1000 units/mg), was dissolved in phosphate buffered saline (PBS) at a concentration of 40 ug/ml. Fresh hydrogen peroxide (50 mM) was prepared from a 30% w/w solution (Sigma, H1009). Incubations were carried out in a water bath maintained at 37° C. Exact volumes varied depending on the catechol, but typically they comprised 1.92 ml PBS, 20 µl DMSO, 20 µl hydrogen peroxide and 20 µl drug in a 4 ml amber glass vial. Prior to addition of the drug, the vial was pre-incubated for 10 min. The reaction was initiated by the addition of 20 µl HRP. Samples (100 µl) were then removed at intervals, added to 100 µl acetonitrile and placed on ice. At the end of the incubation, samples were centrifuged (12000 g, 1 min) to remove precipitated protein and the supernatants placed in polypropylene hplc vials for analysis. Control incubations containing no HRP were carried out in the same way.

HPLC was performed using a Waters 2695 Separations Module with a sample compartment maintained at 10° C., and a Waters 2996 Photodiode Array Detector. The column was an ACE C18, 3 µm particle size, 125×3 mm (Hichrom) maintained at 30° C. Compounds were eluted with varying proportions of A: 5 mM $KH_2PO_4$, 5 mM $H_3PO_4$, and B: 75% acetonitrile, 25% water at a flow rate of 0.6 m/min, in order to achieve a similar starting peak area for each catechol. Occasionally, in order to achieve a better resolution of the products, the latter was replaced with 100% methanol. Spectral data was collected from 220 nm to 500 nm, sampling rate 2/sec, 1.2 nm resolution. Data was analysed using Waters Millennium software.

Results: The loss of peak area at 300 nm of the prodrug was plotted against time, and a straight line fitted to the data. Loss of peak area was used to approximate the relative rates of loss of each catechol. The slope of the line-of-best-fit was then divided by the HRP concentration to give a corrected disappearance (see Table 3).

TABLE 3

Peroxidase-mediated activation of catechols

| catechol | Slope (HPLC Peak area @300 nm/min) | Hrp (ug/ml) | Slope/Hrp | Relative Activation (% Control) |
|---|---|---|---|---|
| ZSB-78 | −66759 | 0.01 | −6675900 | 0.006 |
| ZSB-80 | −43165 | 0.02 | −2158250 | 0.017 |
| ZSB-83 | −19203 | 0.01 | −1902300 | |
| ZSB-82 | −50792 | 0.04 | −1269800 | 0.029 |
| ZSB-74 | −36565 | 0.2 | −182825 | 0.203 |
| CA1 | −39799 | 0.4 | −99498 | 0.373 |
| ZSB-75 | −8713 | 0.4 | −21783 | 1.703 |
| ZSB-77 | −19783 | 1 | −19783 | 1.875 |
| ZSB-84 | −6770 | 0.4 | −16925 | |
| ZSB-71 | −4276 | 0.4 | −10690 | |
| ZSB-76 | −5502 | 1 | −5502 | 6.743 |
| Non-catechol Control | −742 | 2 | −371 | 100 |

Example 6

Enhanced Anti-Tumor Activity of CA1P Relative to CA4P

Evaluation of tumor xenografts treated with CA1P revealed that it not only destroyed centrally located tumor cells but also cells located at the periphery of the tumor. It is expected that in the highly oxygenated regions of the tumor, such as the tumor rim, that are resistant to tumor blood shutdown, CA1 is readily oxidized to its corresponding quinone, and is able to render a single agent response due to this second mechanism of action.

a) Tumor Growth Control in Murine Tumor Models.

The murine adenocarcinoma CaNT was grown subcutaneously on the back of 12- to 16-week old CBA/Gy fTO mice. Tumors were initiated by the injection of 0.05 ml of a crude tumor cell suspension prepared from a donor mouse. Animals were selected for treatment after 3 or 4 weeks, when tumors had reached a geometric mean diameter of 5 to 6.5 mm. CA1P and CA4P were dissolved in 0.9% saline at various concentrations and injected intraperitoneally into tumor bearing mice. Each treatment group consisted of between five and nine mice. A control treatment group was injected with 0.9% saline.

Figure 5:
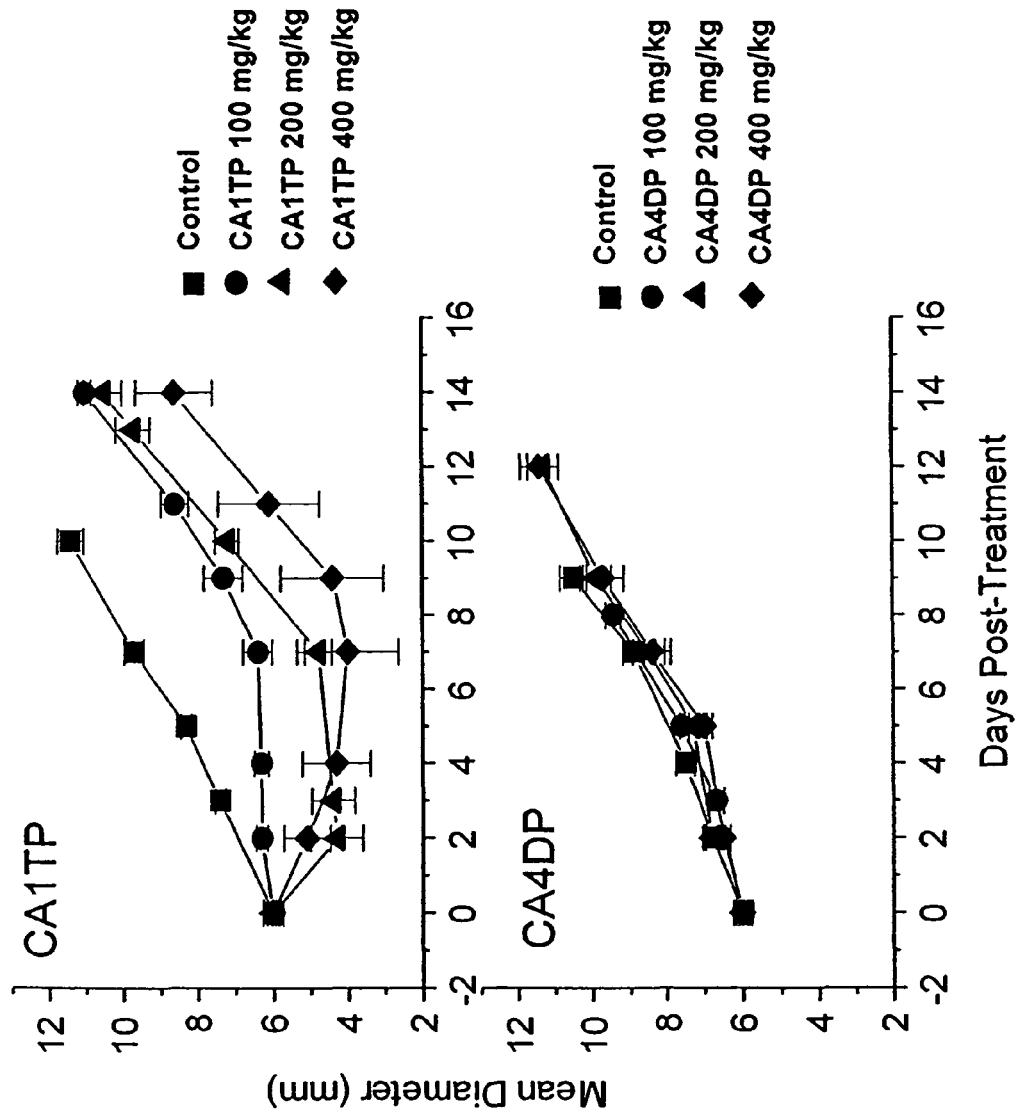
FIG. 5 illustrates the dose dependent effect of CA1P and CA4P on tumor growth control in a CaNT murine tumor model.

The effect of administering single doses of 100, 200, and 400 mg/kg CA1P or CA4P is illustrated in FIG. 5. At all of the doses evaluated, CA1P induced significant tumor growth delay, whereas even the highest dose of CA4P had no measurable effect on tumor growth. Thus, CA1P displays the significant and unexpected property of inducing significant antitumor effects when used as a single agent.

b) Tumor Microvessel Toxicity: Alteration of Tumor Blood Flow.

The following Experiments were performed to evaluate the effects of CA1P on tumor blood flow.

Experiment 1: Effect on Tumor Vessel Number

The effect of CA1P on tumor blood flow was evaluated by quantifying the number of functional tumor vessels in treated murine tumors. MHEC-5T tumors were established as in Example 4c. Tumor bearing mice were injected intraperitoneally with saline control or various dosages of CA1P or CA4P after the transplanted tumor reached a size of 300 mm³ (a size without development of necrosis). Twenty-four hours later they were injected with 0.25 ml of fluorescent Fluo-Sphere beads (0.1 µm beads conjugated with blue fluorescent tag (F-8789, Molecular Probes, Eugene, Oreg.) and diluted 1:6 in physiological saline) in the tail vein, and sacrificed after 3 minutes. Tumors were then excised for cryosections. Cryosections of 8 µm thickness were directly examined under a fluorescent microscope. Functional blood vessels were indicated by blue fluorescence from injected microbeads. For quantification, three sections from three tumors treated in each group were examined and in each section, more than 70% of the area was automatically recorded with a microscopic digital camera at ×10 magnification. A computer program named Stage Pro (Media Cybernetics, MD) was used to control the picture recording. Image analysis was performed with Image Plus software (Media Cybernetics, MD). The results were expressed as vessel area per mm² in percentage of the control.

Figure 6:
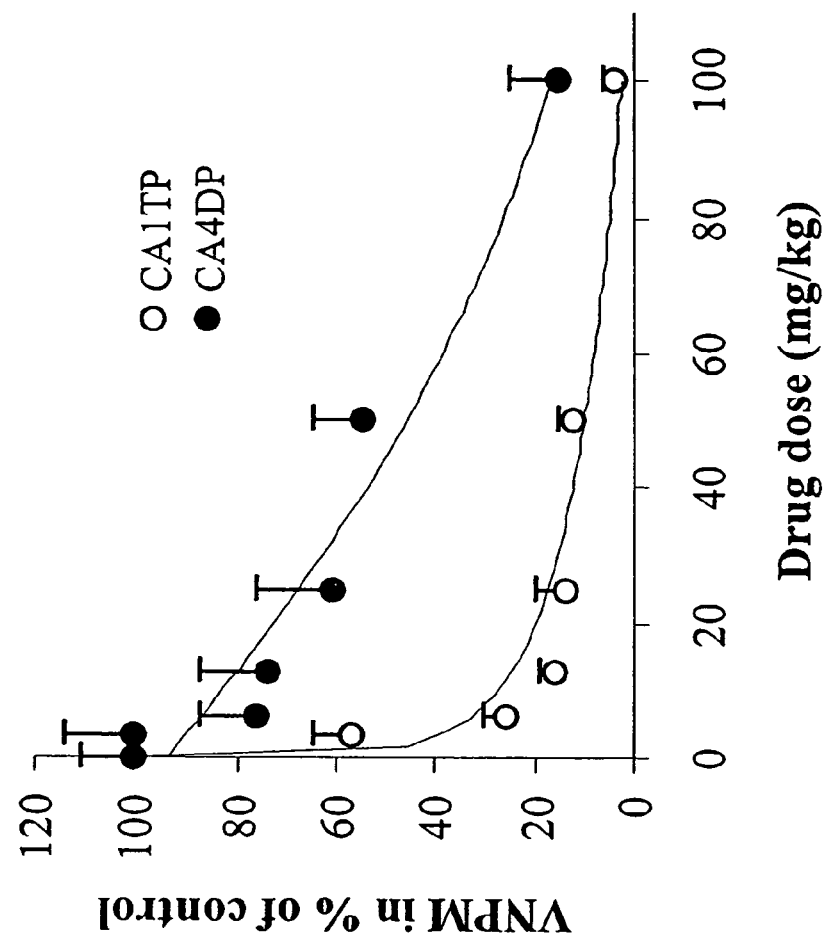
FIG. 6 illustrates the dosage dependent effect of CA1P and CA4P treatment on the number of functional tumor vessels in MHEC-5T tumor bearing mice.

By analysis of functional vessel number per mm² ("VNPM") as a percentage of control, a clear dose-dependent effect was observed in tumors from Oxi4503 treated mice (see FIG. 6). A single i.p. injection of CA1P at 3 mg/kg induced 50%, 6 mg/kg induced a 74%; and 50 mg/kg a 90% reduction in tumor blood flow 24 hr post-drug administration. CA1P exhibited a prominent vascular effect with an $ED_{50}$ of 3 mg/kg in contrast to an $ED_{50}$ of 43 mg/kg for CA4P. Moreover the analysis of the spatial distribution of blood vessel shutdown with Oxi4503 and CA4P showed a different pattern on the tumor periphery. Although treatment with both Oxi4503 and CA4P caused blood flow reduction in the central region of tumors, however in contrast to CA4P, Oxi4503 reduced the blood flow in the peripheral region as well. The tumor periphery is for the purposes of the current evaluation defined as a rim whose width equals 10% of the tumor diameter.

Experiment 2: Effect on Tumor Vascular Volume

The effect of CA1P on tumor blood flow was evaluated by quantification of the functional volume of tumor vessels in treated murine tumors using a procedure previously described in detail and incorporated by reference herein (Smith K A, Br. J. Cancer, 57:247-253, 1988). The murine adenocarcinoma CaNT was grown subcutaneously on the back of 12- to 16-week old CBA/Gy fTO mice. Tumors were initiated by the injection of 0.05 ml of a crude tumor cell suspension prepared from a donor mouse. Animals were selected for treatment after 3 or 4 weeks, when tumors had reached a geometric mean diameter of 5 to 6.5 mm. CA1P and CA4P were dissolved in 0.9% saline at various concentrations and injected intraperitoneally into tumor bearing mice. Each treatment group consisted of between five and nine mice. A control treatment group was injected with 0.9% saline. At 24 hours post-injection, each mouse was injected intravenously with a 10 mg/kg dose of the fluorescent DNA-binding dye Hoechst 333342 and sacrificed 1 minute later. Tumors were immediately excised and bisected. Frozen tumor sections were cut at three levels and viewed under UV excitation where the fluorescent staining of perivascular cells identified perfused vessels. Vascular volumes were quantified based on a random point scoring system previously described and incorporated by reference herein (Chalkley H W, J. Natl Cancer Institute, 4: 47-53, 1943). All estimates were based on counting 100 fields from sections cut at each of the 3 different levels and the calculated vascular volumes were expressed as a percentage of the mean value for control tumors.

Figure 7:
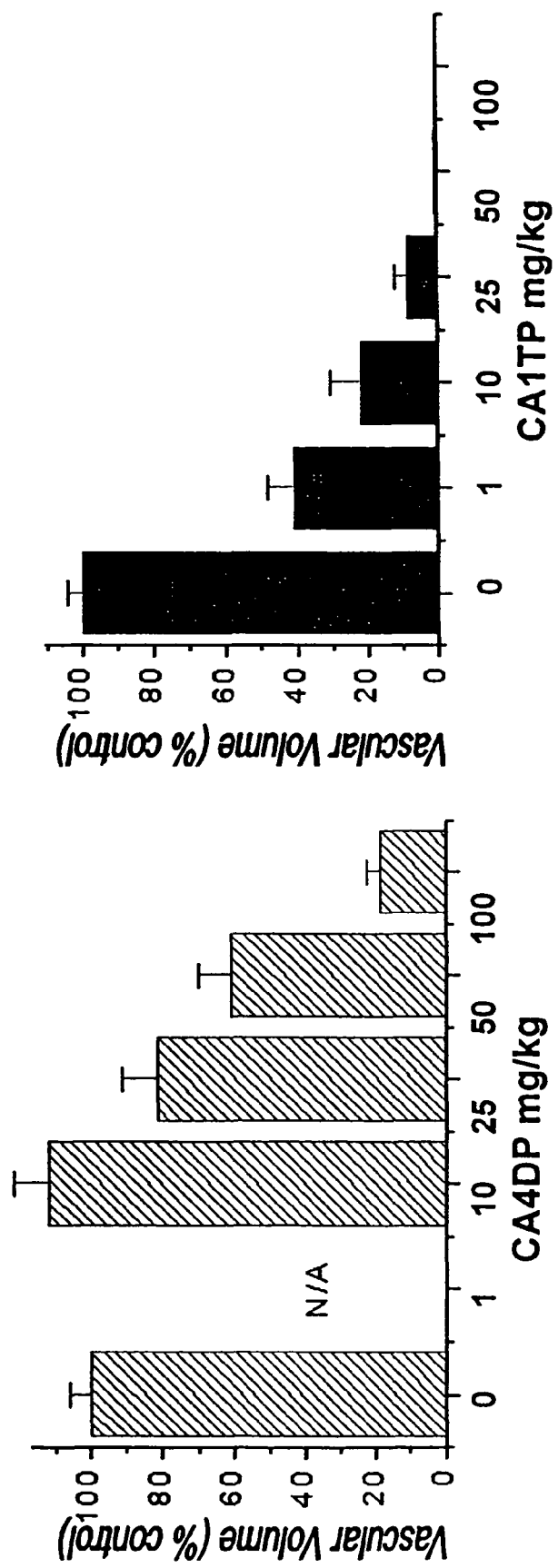
FIG. 7 illustrates the dosage dependent effect of CA1P and CA4P treatment on functional vascular volume of tumor vessels in CaNT tumor bearing mice.

As illustrated in FIG. 7, CA1P is effective at reducing the functional vascular volume of tumor vessels at each of the doses examined. Even at the lowest dose examined (1 mg/kg), CA1P is capable of reducing the percentage of functional vasculature in the tumor by over 50%. In contrast, CA4P displays no significant effect on vascular volume at doses below 50 mg/kg. A dose of 25 mg/kg of CA4P is required to produce an effect that is similar to that of 1 mg/kg of CA1P. Thus, CA1P possesses an unexpected and improved property of enhanced potency as an antivascular agent.

EQUIVALENTS

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A composition of the following formula (V):

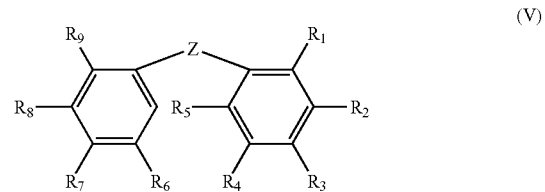

wherein
a. Z is an ethylene (—CH=CH—) bridge in the cis (Z) isomeric configuration;
b. $R_1$ and $R_2$ are OH or a prodrug form thereof;
c. $R_3$ is selected from the group consisting of
  i) a $C_1, C_2, C_3, C_4$ or $C_5$ branched or straight-chain lower alkoxy, cycloalkoxy, heterocycloalkoxy, aryloxy, or lower alkanoyloxy;
  ii) a halogen or trihaloalkyl;
  iii) a $C_1, C_2, C_3, C_4$ or $C_5$ branched or straight chain lower alkyl, allyl, allyloxy, vinyl, or vinyloxy;
  iv) a $C_1, C_2, C_3, C_4$ or $C_5$ primary, secondary, or tertiary alcohol; and
  v) oxo, lower alkanoyl, thio, sulfonyl, sulfonamide, nitro, nitrosyl, cyano, carboxy, carbamyl, aryl, or heterocycle;
d. $R_4$, $R_5$, and $R_9$ are hydrogen,
e. $R_6$ and $R_8$ are the same or different and selected from the group consisting of hydrogen and
  i) a $C_1, C_2, C_3, C_4$ or $C_5$ branched or straight-chain lower alkoxy, cycloalkoxy, heterocycloalkoxy, aryloxy, or lower alkanoyloxy;
  ii) a halogen or trihaloalkyl;
  iii) a $C_1, C_2, C_3, C_4$ or $C_5$ branched or straight chain lower alkyl, allyl, allyloxy, vinyl, or vinyloxy; or
  iv) a $C_1, C_2, C_3, C_4$ or $C_5$ primary, secondary, or tertiary alcohol; and
  v) nitro;
f. $R_7$, is selected from the group consisting of
  i) a $C_1, C_2, C_3, C_4$ or $C_5$ branched or straight-chain lower alkoxy, cycloalkoxy, heterocycloalkoxy, aryloxy, or lower alkanoyloxy;
  ii) a halogen or trihaloalkyl;
  iii) a $C_1, C_2, C_3, C_4$ or $C_5$ branched or straight chain lower alkyl, allyl, allyloxy, vinyl, or vinyloxy;
  iv) a $C_1, C_2, C_3, C_4$ or $C_5$ primary, secondary, or tertiary alcohol; and
  v) nitro;
provided that said compound is not combretastatin A1 or prodrug thereof.

2. The composition of claim 1, wherein $R_6$, $R_7$, and $R_8$ are not hydrogen.

3. The composition of claim 2, wherein $R_6$, $R_7$ and $R_8$ are the same.

4. The composition of claim 3, wherein $R_6$, $R_7$ and $R_8$ are methoxy.

5. The composition of claim 4, wherein $R_3$ is —$CH_3$, —$CH_2CH_3$, —$OCH_2CH_3$, —F, —Br, —$CF_3$, —$CBr_3$, —O—$CH_2$—CH=$CH_2$, —$CH_2$—CH=$CH_2$, —$NO_2$, -cyano, or -carboxy.

6. The composition of claim 3, wherein $R_6$, $R_7$, and $R_8$ are F.

7. The composition of claim 6, wherein $R_3$ is —$CH_3$, —$CH_2CH_3$, —$OCH_2CH_3$, —F, —Br, —$CF_3$, —$CBr_3$, —O—CH$_2$—CH=CH$_2$, —CH$_2$—CH=CH$_2$, —NO$_2$, -cyano, -carboxy, or -benzyl.

8. A composition selected from the group consisting of
- 3-Ethyl-6-[(Z)-2-(3,4,5-trimethoxyphenyl)vinyl]-1,2-dihydroxybenzene,
- 3-Methyl-6-[(Z)-2-(3,4,5-trimethoxyphenyl)vinyl]-1,2-dihydroxybenzene,
- 4-Bromo-6-[(Z)-2-(3,4,5-trimethoxyphenyl)vinyl]-1,2-dihydroxybenzene,
- 4-Phenyl-6-[(Z)-2-(3,4,5-trimethoxyphenyl)vinyl]-1,2-dihydroxybenzene,
- 3-Allyl-6-[(Z)-2-(3,4,5-trimethoxyphenyl)vinyl]-1,2-dihydroxybenzene,
- 4-Fluoro-6-[(Z)-2-(3,4,5-trimethoxyphenyl)vinyl]-1,2-dihydroxybenzene,
- 2,3,4-Trihydroxy-6-[(Z)-2(3,4,5-trimethoxyphenyl)vinyl]-benzene,
- 2,3-Dihydroxy-4-ethoxy-6-[(Z)-2-(3,4,5-trimethoxyphenyl)vinyl]-benzene,
- 2,3-Dihydroxy-4-allyloxy-6-[(Z)-2-(3,4,5-trimethoxyphenyl)vinyl]-benzene,
- 4-Nitro-6-[(Z)-2-(3,4,5-trimethoxyphenyl)vinyl]-2,3-dihydroxybenzene,
- 2',3' dihydroxy-3,5 dichloro-4,4'-dimethoxy-(Z)-stilbene,
- 2',3' dihydroxy-4'-methoxy-3,4,5-trifluoro-(Z)stilbene,
- 2,3-Dihydroxy-4-methoxy-[(Z)-2-(3,4,5-trimethoxyphenyl) Beta-lactam]-benzene,
- 2',3' diphosphate-3,4,5-trimethoxy-(Z)-stilbene, tetrasodium salt;
- 3',4' diphosphate-3,4,5-trimethoxy-(Z)-stilbene, tetrasodium salt;

and combinations thereof.

* * * * *